United States Patent
Takahashi et al.

(10) Patent No.: US 9,597,330 B2
(45) Date of Patent: Mar. 21, 2017

(54) DRUGS FOR TREATING RESPIRATORY DISEASES

(71) Applicant: DAIICHI SANKYO COMPANY, LIMITED, Tokyo (JP)

(72) Inventors: Sakiko Takahashi, Tokyo (JP); Yuki Domon, Tokyo (JP); Yutaka Kitano, Tokyo (JP); Tsuyoshi Shinozuka, Tokyo (JP)

(73) Assignee: Daiichi Sankyo Company, Limited (JP)

( * ) Notice: Subject to any disclaimer, the term of this patent is extended or adjusted under 35 U.S.C. 154(b) by 0 days.

(21) Appl. No.: 14/776,315

(22) PCT Filed: Mar. 13, 2014

(86) PCT No.: PCT/JP2014/056606
§ 371 (c)(1),
(2) Date: Sep. 14, 2015

(87) PCT Pub. No.: WO2014/142221
PCT Pub. Date: Sep. 18, 2014

(65) Prior Publication Data
US 2016/0038486 A1    Feb. 11, 2016

(30) Foreign Application Priority Data

Mar. 14, 2013  (JP) .................................. 2013-052278

(51) Int. Cl.
A61K 31/506  (2006.01)
A61K 31/433  (2006.01)
A61K 31/496  (2006.01)

(52) U.S. Cl.
CPC .......... *A61K 31/506* (2013.01); *A61K 31/433* (2013.01); *A61K 31/496* (2013.01)

(58) Field of Classification Search
CPC ... A61K 31/506; A61K 31/433; A61K 31/496
See application file for complete search history.

(56) References Cited

U.S. PATENT DOCUMENTS 8,889,741 B2 * 11/2014 Shinozuka ........... C07D 403/12
514/256
2014/0045862 A1  2/2014 Shinozuka et al.
2015/0018551 A1  1/2015 Shinozuka et al.

FOREIGN PATENT DOCUMENTS

| JP | 2010-533652 A | 10/2010 |
|---|---|---|
| WO | WO 2006/038594 A1 | 4/2006 |
| WO | WO 2009/012242 A2 | 1/2009 |
| WO | WO 2010/079443 A1 | 7/2010 |
| WO | WO 2011/088201 A1 | 7/2011 |
| WO | WO 2012/004714 A2 | 1/2012 |
| WO | WO 2013/006596 A1 | 1/2013 |
| WO | WO 2013/064983 A1 | 5/2013 |
| WO | WO 2013/118854 A1 | 8/2013 |

OTHER PUBLICATIONS

Cox et al., "An *SCN9A* channelopathy causes congenital inability to experience pain," *Nature*, (2006), 444: pp. 894-898.

Frampton et al., "Pregabalin in the Treatment of Painful Diabetic Peripheral Neuropathy," *Drugs*, (2004), 64(24): pp. 2813-2820.

Kamei et al., "Possible involvement of tetrodotoxin-resistant sodium channels in cough reflex," *European Journal of Pharmacology*, (2011), 652:117-120.

Mazzone et al., "Sensory Neural Targets for the Treatment of Cough," *Clinical and Experimental Pharmacology and Physiology*, (2007), 34:955-962.

Nassar et al., "Nociceptor-specific gene deletion reveals a major role for $Na_v1.7$ (PN1) in acute and inflammatory pain," *Proc. Natl. Acad. Sci.*, (2004), 101(34): pp. 12706-12711.

English translation of International Search Report issued in PCT Application No. PCT/JP2013/052985 on Apr. 23, 2013, 4 pages.

English translation of International Search Report issued in PCT Application No. PCT/JP2014/056606 on Jun. 17, 2014, 2 pages.

* cited by examiner

Primary Examiner — D M Seaman
(74) Attorney, Agent, or Firm — Dorsey & Whitney LLP

(57) ABSTRACT

It is intended to provide a therapeutic agent and/or a preventive agent for a respiratory disease or a therapeutic agent and/or a preventive agent for a sodium channel associated disease. The present invention provides a pharmaceutical comprising a compound represented by the following formula (I) or a pharmacologically acceptable salt thereof as an active ingredient:

[Formula 1]

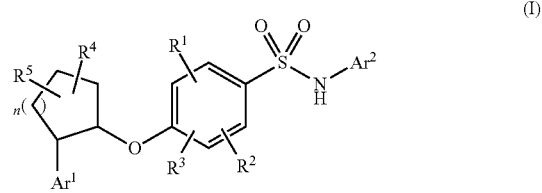

(I)

$Ar^1$ and $Ar^2$: a heteroaryl group or an aryl group; $R^1$, $R^2$ and $R^3$: a hydrogen atom, a halogen atom, a C1-C6 alkyl group, a halogenated C1-C6 alkyl group, a hydroxy C1-C6 alkyl group, a C1-C6 alkoxy C1-C6 alkyl group or a C3-C7 cycloalkyl group or a cyano group; $R^4$ and $R^5$: a hydrogen atom, a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group or a C1-C6 alkoxy group;

n: an integer of 1 to 3; and the heteroaryl or aryl group optionally has one or two groups independently selected from a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group, a carboxyl group, a cyano group, an amino group, a C1-C3 alkylamino group and a di-C1-C3 alkylamino group, and when the heteroaryl or aryl group has two such groups, the two groups are the same as or different from each other.

15 Claims, No Drawings

DRUGS FOR TREATING RESPIRATORY DISEASES

This application is a national stage application under 35 U.S.C. §371 of International Application No. PCT/JP2014/056606, filed Mar. 13, 2014, entitled "Drug for Respiratory Diseases," which claims priority to Japanese Patent Application No. 2013-052278, filed Mar. 14, 2013.

BACKGROUND OF THE INVENTION

Field of the Invention.

The present invention relates to a drug for treating and/or preventing a respiratory disease, particularly, cough, comprising a compound represented by formula (I) described later, a salt, or a hydrate thereof. The present invention further relates to a method for treating and/or preventing a respiratory disease, particularly, cough, comprising administering the compound described above or the like.

Description of the Related Art.

Cough is a common defensive reflex action in the respiratory tract for healthy subject, however, persistent cough associated with various diseases greatly reduces patients' quality of life.

Antitussives are classified into central antitussives, which exhibit antitussive activities by blocking the cough center, and peripheral antitussives, which block stimulation of peripheral cough receptors. Central antitussives, such as codeine phosphate and dextromethorphan, cause adverse drug reactions including respiratory depression, sleepiness, constipation, and the like and also present problems such as resistance and dependence due to repeated use. On the other hand, the peripheral antitussives, such as methylephedrine, often have insufficient antitussive activities. For such reasons, there has been a demand for the development of safe and more effective antitussives.

Voltage-gated sodium channels (Navs) are ion channels each including an α subunit having four domains and auxiliary acting β subunits, at least nine subtypes thereof having been reported so far, and these subtypes respectively have different expression distributions and physiological actions so as to regulate biological functions.

The sodium channels are an intrinsic part of neural activities, and drugs such as lidocaine and mexiletine are known as inhibitors for sodium channels. As for cough, the respiratory tract is considered to be controlled by various neural activities. There are many preclinical and clinical data showing that these sodium channel inhibitors are effective for the suppression of cough (Patent Literatures 1 and 2 and Non-Patent Literatures 1 and 2). Such drugs have, however, low selectivity for the Nav subtypes. Since sodium channels of the different subtypes are expressed in muscles, cardiac muscle cells and the central nervous system as shown in Table 1, the problem arises of adverse drug reactions caused when such drugs are systemically administered.

TABLE 1

| Subtype | Main expression site |
| --- | --- |
| Nav1.1 | Central nervous system |
| Nav1.2 | Central nervous system |
| Nav1.3 | Central nervous system |
| Nav1.4 | Skeletal muscle |
| Nav1.5 | Cardiac muscle cells |
| Nav1.6 | Sensory/motor nervous system |
| Nav1.7 | Sensory nervous system |
| Nav1.8 | Sensory nervous system |
| Nav1.9 | Sensory nervous system |

Patent Literature 1 relates to a Nav 1.7 modulator and states that the Nav 1.7 modulator is useful for various respiratory diseases. This patent literature specifically describes a compound represented by formula (A) below (for example, Example 6), which is described in the claims as falling within a structure represented by formula (B) below. A feature of the compound described in said patent literature is that the compound is a pyridine derivative substituted at the 2-position by a piperidine ring or a pyrrolidine ring. By contrast, the compound used in the present invention is very different therefrom, for example, in that a cycloalkane is connected to an aromatic ring through an oxygen atom. Patent Literature 1 neither describes nor suggests the structure of the compound used in the present invention.

[Formula 1]

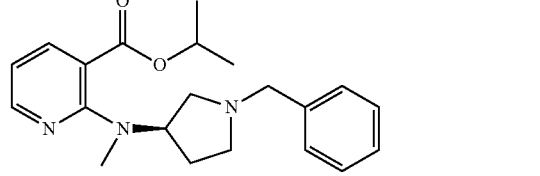

(A)

[Formula 2]

(B)

Patent Literature 2 below relates to a Nav 1.7 modulator and states that the Nav 1.7 modulator is useful for various respiratory diseases. This patent literature specifically describes a compound represented by formula (C) below (for example, Example 474), which is described in the claims as falling within a structure represented by formula (D) below. A feature of the compound described in said patent literature is that the compound is a pyridine derivative substituted at the 2-position by a piperazine ring. By contrast, the compound used in the present invention is very different therefrom, for example, in that a cycloalkane is connected to an aromatic ring through an oxygen atom. Patent Literature 2 neither describes nor suggests the structure of the compound used in the present invention.

[Formula 3]

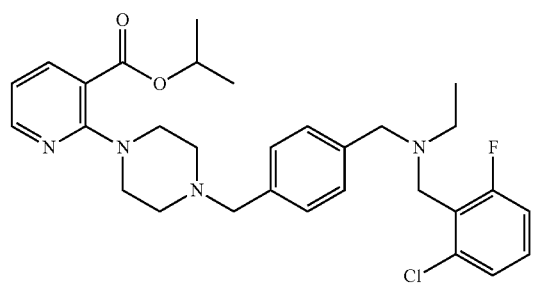

(C)

[Formula 4]

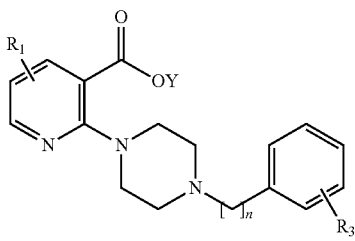

(D)

Patent Literature 3 below relates to a Nav 1.7 modulator and specifically describes, for example, a compound represented by formula (E) below (for example, Example 811). Features of the compound described in this patent literature are that two aromatic rings are connected through an oxygen atom, and further, N-substituted sulfonamide is connected to one of the aromatic rings (phenyl group). The compound used in the present invention differs therefrom in that a cycloalkane is connected to an aromatic ring through an oxygen atom. Patent Literature 3 neither describes nor suggests the structure of the compound used in the present invention.

[Formula 5]

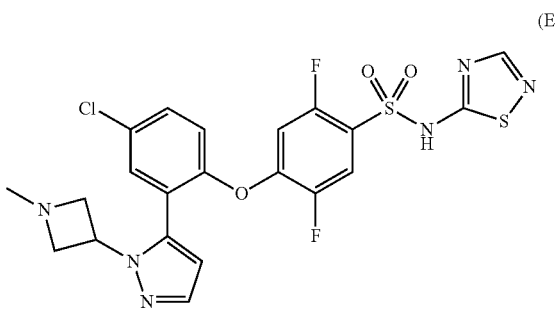

(E)

The compound disclosed in said Patent Literature 3 is described in the claims as falling within a structure represented by formula (F) below. The moiety B in this structure is defined as "phenyl or Het², wherein Het² is defined as a 5- or 6-membered aromatic heterocyclic group containing (a) one to four nitrogen atoms, (b) one oxygen atom or one sulfur atom, or (c) one oxygen atom or one sulfur atom and one or two nitrogen atoms". Thus, the moiety B is an aromatic substituent, and the patent reference does not disclose that this moiety is a saturated substituent. Specifically, said patent literature does not disclose that a cycloalkane can be introduced as the corresponding partial structure, as in the compound of formula (I) used in the present application. The patent literature does not disclose that the Nav 1.7 modulator is effective for respiratory diseases.

[Formula 6]

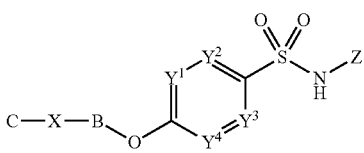

(F)

Patent Literature 4 below relates to an N-type calcium channel inhibitor and specifically describes, for example, a compound represented by formula (G) below (for example, Example 5(11)). The compound described in said patent reference has a structure in which an aromatic ring and a saturated heterocyclic ring are connected through a polymethylene(oxy) chain. An N-substituted sulfonamide is bonded to an aromatic ring (phenyl group), and two substituents are further introduced at the nitrogen atom of this sulfonamide. Specifically, a feature of this compound is that the nitrogen atom of the sulfonamide is di-substituted. The compound of the present invention differs therefrom in that: the saturated ring is not a heterocyclic ring; a cycloalkane and an aromatic ring are connected through an oxygen atom and not through a polymethylene chain; and the sulfonamide moiety is mono-substituted at its nitrogen atom. Said Patent Literature 2 neither describes nor suggests at all the structure of the compound used in the present invention. The patent literature does not disclose that the Nav 1.7 modulator is effective for respiratory diseases.

[Formula 7]

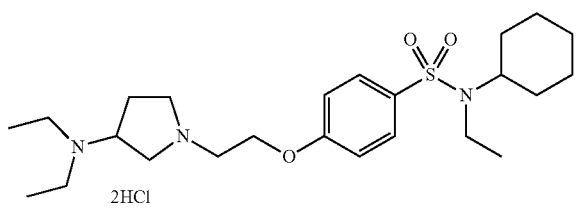

(G)

Neither does the compound used in the present invention fall within a structure represented by formula (H) below described in the claims of Patent Literature 4, nor is the structure of the compound used in the present invention suggested by the description related to this structure.

[Formula 8]

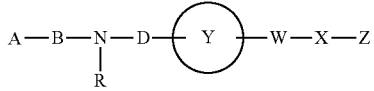

(H)

PRIOR ART LITERATURE

Patent Literature

[Patent Literature 1] International Publication No. WO 2011/088201
[Patent Literature 2] International Publication No. WO 2013/006596
[Patent Literature 3] International Publication No. WO 2010/079443
[Patent Literature 4] International Publication No. WO 2006/038594

Non-Patent Literature

[Non-Patent Literature 1] Kamei J. et al., European Journal of Pharmacology, 652, 117-120, 2011.

[Non-Patent Literature 2] Mazzone S. B., Clinical and Experimental Pharmacology and Physiology, 34, 955-962, 2007.

SUMMARY OF THE INVENTION

Problem to be Solved by the Invention

An object of the present invention is to provide a highly selective drug for a respiratory disease and a sodium channel inhibitor that has high treatment efficacy on respiratory diseases by administering a compound represented by formula (I) described later, a salt, or a hydrate thereof having an excellent selectivity for sodium channel inhibitory activities, and is further directed to reducing adverse drug reaction caused by systemic administration, in response to, for example, low levels of satisfaction with conventional therapeutic agents for respiratory diseases and the low activities and selectivity of conventional sodium channel inhibitory agents.

Means to Solve the Problem

The present inventors have earnestly conducted studies and consequently completed the present invention by finding that a compound represented by formula (I) below having a structure in which a phenyl group to which an N-aromatic substituent-substituted sulfonamide group is connected, and to which a cyclic alkyl group having an aromatic group as a substituent is connected through an oxygen atom to the para position with respect to the sulfonamide group, a salt, or a hydrate thereof exhibits excellent antitussive activities and serves as an excellent drug for a respiratory disease.

Specifically, the present invention relates to:

(1) A drug for a respiratory disease comprising a compound represented by following formula (I), a pharmacologically acceptable salt, or a hydrate thereof as an active ingredient:

[Formula 9]

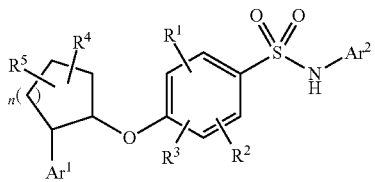

(I)

wherein Ar¹ and Ar², each independently represents a heteroaryl group or an aryl group, R¹, R² and R³, each independently represents a hydrogen atom, a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group or a cyano group, R⁴ and R⁵, each independently represents a hydrogen atom, a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group or a C1-C6 alkoxy group, and n represents an integer of 1 to 3, and wherein the heteroaryl or aryl group optionally has one or two substituents independently selected from a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group, a carboxy group, a cyano group, an amino group, a C1-C3 alkylamino group and a di-C1-C3 alkylamino group, and when the heteroaryl or aryl group has two substituents, the two substituents may be the same or different from each other.

The present invention further relates to the following:

(2) A drug for a respiratory disease according to (1), wherein in formula (I),

Ar¹ and Ar², each independently represents a heteroaryl group,

R¹, R² and R³, each independently represents a hydrogen atom, a halogen atom, a C1-C6 alkyl group, a halogenated C1-C6 alkyl group or a C3-C7 cycloalkyl group, R⁴ and R⁵, each independently represents a hydrogen atom, a halogen atom, a C1-C6 alkyl group or a halogenated C1-C6 alkyl group, and the substituent on the heteroaryl group is one or two substituents selected from the group consisting of a halogen atom, a C1-C6 alkyl group, a halogenated C1-C6 alkyl group, a hydroxyl group, a hydroxy C1-C6 alkyl group, a C3-C7 cycloalkyl group, an amino group, a C1-C3 alkylamino group and a di-C1-C3 alkylamino group.

(3) A drug for a respiratory disease according to (1) or (2), wherein the heteroaryl group is a 5- or 6-membered nitrogen-containing aromatic heterocyclic group.

(4) A drug for a respiratory disease according to any one of (1) to (3), wherein Ar¹ is a pyridyl, pyridazinyl, pyrimidinyl, pyrazolyl or imidazolyl group, optionally having substituent(s).

(5) A drug for a respiratory disease according to any one of (1) to (4), wherein Ar¹ is a pyridyl, pyridazinyl, pyrimidinyl, pyrazolyl or imidazolyl group, optionally having one or two substituents selected from the group consisting of a chlorine atom, a fluorine atom, a methyl group, an ethyl group, a trifluoromethyl group, an amino group, a methylamino group and a dimethylamino group.

(6) A drug for a respiratory disease according to any of (1) to (5), wherein Ar² is a thiadiazolyl, thiazolyl, pyrimidinyl, isoxazolyl, oxazolyl or isothiazolyl group, optionally having substituent(s).

(7) A drug for a respiratory disease according to any one of (1) to (6), wherein Ar² is a thiadiazolyl, thiazolyl p, pyrimidinyl, isoxazolyl, oxazolyl or isothiazolyl group, optionally having a chlorine atom, a fluorine atom or a methyl group as substituent(s).

(8) A drug for a respiratory disease according to any of (1) to (7), wherein R¹, R² and R³, each independently represents a hydrogen atom, a chlorine atom, a fluorine atom, a methyl group, an ethyl group, a trifluoromethyl group or a cyano group.

(9) A drug for a respiratory disease according to any one of (1) to (8), wherein R⁴ and R⁵, each independently represents a hydrogen atom, a fluoro group or a methyl group.

(10) A drug for a respiratory disease according to (1), wherein the compound represented by formula (I) is 2-fluoro-4-{[(1S*,2R*)-2-(1-methyl-1H-pyrazol-5-yl)cyclopentyl]oxy}-N-(pyrimidin-4-yl)benzenesulfonamide; 4-{[(1S*,2R*)-2-(1-ethyl-1H-pyrazol-5-yl)cyclopentyl]oxy}-2,3-difluoro-N-(pyrimidin-4-yl)benzenesulfonamide; 5-chloro-2-fluoro-4-{[(1S*,2R*)-2-(1-methyl-1H-pyrazol-5-yl)cyclohexyl]oxy}-N-(pyrimidin-4-yl)benzenesulfonamide; 2,6-difluoro-4-{[(1S*,2R*)-2-(1H-pyrazol-4-yl)cyclohexyl]oxy}-N-(pyrimidin-4-yl)benzenesulfonamide; 4-{[(1S,2R)-2-(1-ethyl-1H-pyrazol-5-yl)cyclopentyl]oxy}-2,3-difluoro-N-(pyrimidin-4-yl)benzenesulfonamide; 5-chloro-2-fluoro-4-{[(1S,2R)-2-(1-methyl-1H-pyrazol-5-yl)cyclohexyl]oxy}-N-(pyrimidin-4-yl)benzenesulfonamide; 2-fluoro-4-{[(1S,2R)-2-(1-methyl-1H-pyrazol-5-yl)cyclopentyl]oxy}-N-(pyrimidin-4-yl)benzenesulfonamide; 4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide; 4-{[(1S,2R)-5,5-difluoro-2-(1H-pyrazol-4-yl)cyclohexyl]oxy}-2-fluoro-5-methyl-N-(pyrimidin-4-yl)benzenesulfonamide; or 2,6-difluoro-4-{[(1S,2R)-2-(1H-pyrazol-4-yl)cyclohexyl]oxy}-N-(pyrimidin-4-yl)benzenesulfonamide.

(11) A drug for a respiratory disease according to (1), wherein the compound represented by formula (I) is 2-fluoro-4-{[(1S*,2R*)-2-(1-methyl-1H-pyrazol-5-yl)cyclopentyl]oxy}-N-(pyrimidin-4-yl)benzenesulfonamide.

(12) A drug for a respiratory disease according to (1), wherein the compound represented by formula (I) is 4-{[(1S*,2R*)-2-(1-ethyl-1H-pyrazol-5-yl)cyclopentyl]oxy}-2,3-difluoro-N-(pyrimidin-4-yl)benzenesulfonamide.

(13) A drug for a respiratory disease according to (1), wherein the compound represented by formula (I) is 5-chloro-2-fluoro-4-{[(1S*,2R*)-2-(1-methyl-1H-pyrazol-5-yl)cyclohexyl]oxy}-N-(pyrimidin-4-yl)benzenesulfonamide.

(14) A drug for a respiratory disease according to (1), wherein the compound represented by formula (I) is 2,6-difluoro-4-{[(1S*,2R*)-2-(1H-pyrazol-4-yl)cyclohexyl]oxy}-N-(pyrimidin-4-yl)benzenesulfonamide.

(15) A drug for a respiratory disease according to (1), wherein the compound represented by formula (I) is 4-{[(1S,2R)-2-(1-ethyl-1H-pyrazol-5-yl)cyclopentyl]oxy}-2,3-difluoro-N-(pyrimidin-4-yl)benzenesulfonamide.

(16) A drug for a respiratory disease according to (1), wherein the compound represented by formula (I) is 5-chloro-2-fluoro-4-{[(1S,2R)-2-(1-methyl-1H-pyrazol-5-yl)cyclohexyl]oxy}-N-(pyrimidin-4-yl)benzenesulfonamide.

(17) A drug for a respiratory disease according to (1), wherein the compound represented by formula (I) is 2-fluoro-4-{[(1S,2R)-2-(1-methyl-1H-pyrazol-5-yl)cyclopentyl]oxy}-N-(pyrimidin-4-yl)benzenesulfonamide.

(18) A drug for a respiratory disease according to (1), wherein the compound represented by formula (I) is 4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide.

(19) A drug for a respiratory disease according to (1), wherein the compound represented by formula (I) is 4-{[(1S,2R)-5,5-difluoro-2-(1H-pyrazol-4-yl)cyclohexyl]oxy}-2-fluoro-5-methyl-N-(pyrimidin-4-yl)benzenesulfonamide.

(20) A drug for a respiratory disease according to (1), wherein the compound represented by formula (I) is 2,6-difluoro-4-{[(1S,2R)-2-(1H-pyrazol-4-yl)cyclohexyl]oxy}-N-(pyrimidin-4-yl)benzenesulfonamide.

(21) The drug for a respiratory disease according to (1) to (20), wherein the respiratory disease is a disease selected from or a disease showing a symptom selected from the group consisting of: asthma; cystic fibrosis; bronchitis; chronic bronchitis; bronchial asthma; bronchiectasis; chronic obstructive pulmonary disease (COPD); cough; acute respiratory distress syndrome (ARDS); pulmonary tuberculosis; interstitial pneumonia; pleuritis; pneumonia; emphysema; pneumoconiosis; diffuse panbronchiolitis; rheumatism; silicosis; spontaneous pneumothorax; cold syndrome; pulmonary embolism; pulmonary infarction; and dry cough.

(22) The drug for a respiratory disease according to (1) to (20) which is an antitussive.

(23) The drug for a respiratory disease according to (22) intended for administration to a mammal.

(24) The drug for a respiratory disease according to (23), wherein the mammal is a human.

(25) A pharmaceutical composition for treating and/or preventing a respiratory disease, comprising a pharmacologically effective dose of a compound of formula (I), a pharmacologically acceptable salt, or a hydrate thereof according to (1), and a pharmaceutically acceptable carrier.

(26) The pharmaceutical composition according to (25), wherein the respiratory disease is a disease selected from or a disease manifesting a symptom selected from the group consisting of: asthma; cystic fibrosis; bronchitis; chronic bronchitis; bronchial asthma; bronchiectasis; chronic obstructive pulmonary disease (COPD); cough; acute respiratory distress syndrome (ARDS); pulmonary tuberculosis; interstitial pneumonia; pleuritis; pneumonia; emphysema; pneumoconiosis; diffuse panbronchiolitis; rheumatism; silicosis; spontaneous pneumothorax; cold syndrome; pulmonary embolism; pulmonary infarction; and dry cough.

(27) The pharmaceutical composition according to (25) or (26), which is administered to a mammal.

(28) The pharmaceutical composition according to (27), wherein the mammal is a human.

(29) A method for treating and/or preventing a respiratory disease, comprising administering a compound of formula (I), a pharmacologically acceptable salt, or a hydrate thereof according to (1).

(30) The method for treating and/or preventing a respiratory disease according to (29) which is a method for treating and/or preventing a disease or symptom selected from the following group:

asthma; cystic fibrosis; bronchitis; chronic bronchitis; bronchial asthma; bronchiectasis; chronic obstructive pulmonary disease (COPD); cough; acute respiratory distress syndrome (ARDS); pulmonary tuberculosis; interstitial pneumonia; pleuritis; pneumonia; emphysema; pneumoconiosis; diffuse panbronchiolitis; rheumatism; silicosis; spontaneous pneumothorax; cold syndrome; pulmonary embolism; pulmonary infarction; and dry cough.

(31) The treatment and/or prevention method according to (29) or (30) which is a treatment and/or prevention method for a mammal.

(32) The treatment and/or prevention method according to (31), wherein the mammal is a human.

(33) An antitussive for various respiratory diseases, comprising administering a compound of formula (I), a pharmacologically acceptable salt, or a hydrate thereof according to (1).

(34) An antitussive intended for application to bronchial asthma, asthmatic bronchitis, acute bronchitis, chronic bronchitis, cold, bronchiectasis, pneumonia, pulmonary tuberculosis, upper respiratory inflammation, laryngopharyngitis, nasal catarrh, bronchitis, asthmatic bronchitis, or cough associated with bronchial asthma, comprising administering a compound of formula (I), a pharmacologically acceptable salt, or a hydrate thereof according to (1).

(35) A method for treating and/or preventing bronchial asthma, asthmatic bronchitis, acute bronchitis, chronic bronchitis, cold, bronchiectasis, pneumonia, pulmonary tuberculosis, upper respiratory inflammation, laryngopharyngitis, nasal catarrh, bronchitis, asthmatic bronchitis, or cough associated with bronchial asthma, comprising administering a compound of formula (I), a pharmacologically acceptable salt, or a hydrate thereof according to (1).

The compound of formula (I) serving as an active ingredient used in (25) to (35) can be a compound having a more specific structure of the compound described in (2) to (20) above.

Advantageous Effects of Invention

The compound represented by formula (I), a pharmacologically acceptable salt thereof, or a hydrate thereof used in the present invention has excellent voltage-gated sodium channel 1.7 (Nav 1.7) inhibitory activities and has excellent subtype selectivity, and hence has excellent antitussive activities in warm-blooded animals (preferably mammals including humans). Accordingly, the drug of the present invention comprising the compound serves as an excellent drug for a respiratory disease. In addition, the compound shows excellent sodium channel inhibiting activities and is thus excellent as a sodium channel inhibitor.

DETAILED DESCRIPTION OF THE PREFERRED EMBODIMENTS

The present invention will now be described in detail below. First, the compound represented by formula (I) (hereinafter, referred to as compound (I)) used in the present invention will be described. This compound (I) has the following structure:

[Formula 10]

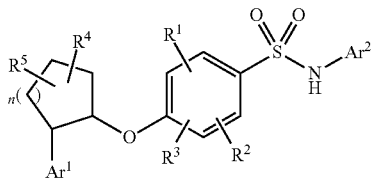

(I)

This structure and each substituent will be described.

In the present specification, a "halogen atom" refers to a fluorine atom, a chlorine atom, a bromine atom or an iodine atom.

In the present specification, a "C1-C6 alkyl group" refers to a linear or branched alkyl group having 1 to 6 carbon atoms. Examples thereof can include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group and a 2-ethylbutyl group.

In the present specification, a "C1-C3 alkyl group" refers to a linear or branched alkyl group having 1 to 3 carbon atoms, and examples thereof can include a methyl group, an ethyl group, a propyl group and an isopropyl group.

In the present specification, a "halogenated C1-C6 alkyl group" refers to a group obtained by substituting a "C1-C6 alkyl group" defined above with a "halogen atom" defined above. The number of halogen atoms as substituents is not particularly limited but the substitution may be from mono-substitution to per-substitution. The substitution position is not particularly limited but mono-substitution is preferably at the terminal carbon atom of the alkyl group. Examples of the halogenated C1-C6 alkyl group can include a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group, a 2-fluoroethyl group, a 2-iodoethyl group, a 3-chloropropyl group, a 4-fluorobutyl group and a 6-iodohexyl group.

In the present specification, a "hydroxy C1-C6 alkyl group" refers to a group obtained by substituting a "C1-C6 alkyl group" defined above with a hydroxy group. The substitution position of the hydroxy group is not particularly limited but the terminal carbon atom of the alkyl group is more preferably substituted. Examples of the hydroxy C1-C6 alkyl group can include a hydroxymethyl group, a 2-hydroxyethyl group, a 3-hydroxypropyl group, a 4-hydroxybutyl group, a 5-hydroxypentyl group, a 6-hydroxyhexyl group, a 1-hydroxyethyl group, a 1-hydroxypropyl group and a 2-hydroxypropyl group.

In the present specification, a "C1-C6 alkoxy group" refers to a group formed by bonding the terminal of a "C1-C6 alkyl group" defined above to an oxygen atom, and examples of the C1-C6 alkoxy group can include a methoxy group, an ethoxy group, a propoxy group, an isopropoxy group, a butoxy group, an isobutoxy group, a sec-butoxy group, a tert-butoxy group, a pentoxy group, an isopentoxy group, a 2-methylbutoxy group, a neopentoxy group, a hexyloxy group, a 4-methylpentoxy group, a 3-methylpentoxy group and a 2-methylpentoxy group.

In the present specification, a "C1-C6 alkoxy C1-C6 alkyl group" refers to a group obtained by substituting a "C1-C6 alkyl group" defined above with a "C1-C6 alkoxy group" defined above. The substitution position of the alkoxy group is not particularly limited but the terminal carbon atom of the alkyl group is preferably substituted. Examples of the C1-C6 alkoxy C1-C6 alkyl group can include a methoxymethyl group, an ethoxymethyl group, a propoxymethyl group, a butoxymethyl group, a 3-methoxypropyl group, a 3-ethoxypropyl group, a 4-methoxybutyl group, a 5-methoxypentyl group and a 6-methoxyhexyl group.

In the present specification, a "C3-C7 cycloalkyl group" refers to a saturated cyclic hydrocarbon group having 3 to 7 carbon atoms, and examples thereof can include a cyclopropyl group, a cyclobutyl group, a cyclopentyl group, a cyclohexyl group and a cycloheptyl group.

In the present specification, a "C1-C3 alkylamino group" refers to an amino group in which one "C1-C3 alkyl group" defined above is bonded to its nitrogen atom. Examples of the C1-C3 alkylamino group can include a methylamino group, an ethylamino group, a propylamino group and an isopropylamino group.

In the present specification, a "di-C1-C3 alkylamino group" refers to an amino group in which two "C1-C3 alkyl groups" defined above are bonded to its nitrogen atom. The two alkyl groups may be the same or different from each other. Examples of the di-C1-C3 alkylamino group can include a dimethylamino group, an ethylmethylamino group, a diethylamino group, a methylpropylamino group, an ethylpropylamino group, a dipropylamino group, an isopropylmethylamino group, an ethylisopropylamino group and a diisopropylamino group.

In the present specification, an "aryl group" refers to an aromatic hydrocarbon substituent and examples thereof can include a phenyl group and a naphthyl group, and the aryl group may be bonded at any position.

In the present specification, a "heteroaryl group" refers to a 5- or 6-membered aromatic heterocyclic substituent having 1 to 4 heteroatoms independently selected from the group consisting of a nitrogen atom, an oxygen atom and a sulfur atom. Examples of the heteroaryl group can include a pyridyl group, a pyrimidinyl group, a pyridazinyl group, a pyrazinyl group, a triazolyl group, a pyrazolyl group, an imidazolyl group, a tetrazolyl group, an isoxazolyl group, an oxazolyl group, an isothiazolyl group, a triazolyl group, a thiadiazolyl group, an oxadiazolyl group, a thiophenyl group and a furanyl group. Such an aromatic heterocyclic group may be bonded in any position (it is noted that the above-described names of the groups are mentioned merely as generic designations of substituents but do not specify a bonding position).

The compound used in the present invention has a structure represented by formula (I). Specifically, an N-monoaromatic substituent-substituted sulfonamide group is bonded to a phenyl group (the aromatic group on the nitrogen atom of this sulfonamide group is referred to as $Ar^2$); a cycloalkyl group is connected through an oxygen atom to the para position with respect to the position at which the sulfonamide group is bonded; and an aromatic group (referred to as $Ar^1$) is bonded to the carbon atom adjacent to the carbon atom where the cycloalkyl group is bonded to the oxygen atom.

In the compound (I), the two aromatic groups represented by $Ar^1$ and $Ar^2$ may each independently represent an aryl group (aromatic hydrocarbon group) or a heteroaryl group (aromatic heterocyclic group). Each of these aromatic groups may further have substituent(s). Also, the phenyl group to which the sulfonamide is connected may have from one to three substituents. The cycloalkyl group connected through the oxygen atom to the phenyl group to which sulfonamide is connected can be any from a 5- to a 7-membered ring in size. This ring may have 1 or 2 substituents, and when the ring has two such groups, the two groups may be the same or different from each other.

The aromatic group $Ar^1$ may be an aryl group but more preferably is a heteroaryl group. The heteroaryl group can be any monocyclic 5- or 6-membered ring containing 1 to 4 heteroatoms. The heteroatom(s) are preferably nitrogen atom(s).

The 5-membered heteroaryl group can be selected from those exemplified above but is preferably a group containing only nitrogen atom(s) as heteroatom(s). Preferable examples thereof can include a pyrazolyl group and an imidazolyl group. A pyrazolyl group is more preferred.

The connecting position of such a 5-membered heteroaryl group to the cyclic alkyl group is not particularly limited. In the case of a pyrazolyl group or an imidazolyl group, examples can include pyrazol-1-yl, pyrazol-3-yl, pyrazol-4-yl, imidazol-1-yl and imidazol-4-yl. Among them, pyrazol-3-yl, pyrazol-4-yl, imidazol-4-yl or the like is preferred.

The 6-membered heteroaryl group preferably contains only nitrogen atom(s) as heteroatom(s), as in the 5-membered ring. A pyridyl group or a pyridazinyl group is preferred. The connecting position is not limited but is preferably pyridin-4-yl, pyridin-3-yl or pyridazin-4-yl.

$Ar^1$ may have substituent(s) and these may be 1 or 2 substituents independently selected from the group consisting of a halogen atom, a C1-C6 alkyl group, a halogenated C1-C6 alkyl group, a hydroxyl group, a hydroxy C1-C6 alkyl group, a C3-C7 cycloalkyl group, an amino group, a C1-C3 alkylamino group and a di-C1-C3 alkylamino group. Among these, a halogen atom, a C1-C6 alkyl group, a halogenated C1-C6 alkyl group, an amino group, a C1-C3 alkylamino group or a di-C1-C3 alkylamino group is more preferred. Examples of such substituents can include a chlorine atom, a fluorine atom, a methyl group, an ethyl group, a trifluoromethyl group, an amino group, a methylamino group and a dimethylamino group. The substituent(s) of $Ar^1$ is preferably an amino group or an alkyl group. The alkyl group is preferably a methyl group or an ethyl group. The alkyl group may substitute either on a nitrogen atom or a carbon atom.

Examples of $Ar^1$ can include a phenyl group, a 1H-pyrazol-4-yl group, a 1-methyl-1H-pyrazol-5-yl group, a 1-ethyl-1H-pyrazol-5-yl group, a 3-amino-1H-pyrazol-4-yl group, a 1H-imidazol-1-yl group, a 1-methyl-1H-imidazol-5-yl group, a pyridin-3-yl group, a 2-aminopyridin-3-yl group, a 2-methylpyridin-3-yl group and a 2-pyridazin-4-yl group. Among these, a phenyl group, a 1-methyl-1H-pyrazol-5-yl group, a 1-ethyl-1H-pyrazol-5-yl group, a 1H-pyrazol-4-yl group or a 3-amino-1H-pyrazol-4-yl group is preferred.

Likewise, the aromatic group $Ar^2$ is more preferably a heteroaryl group. The heteroaryl group can be any 5- or 6-membered ring containing two or more heteroatoms. Examples of the 5-membered heteroaryl group can include an imidazolyl group, a triazolyl group, an isoxazolyl group, an oxazolyl group, an isothiazolyl group, a triazolyl group, a thiadiazolyl group and an oxadiazolyl group. Examples of the 6-membered heteroaryl group can include a pyridyl group, a pyrimidinyl group, a pyridazinyl group and a pyrazinyl group. Among these, a thiadiazolyl group, a thiazolyl group or a pyrimidinyl group is more preferred.

$Ar^2$ may have substituent(s) and may have 1 or 2 substituents independently selected from the group consisting of a halogen atom, a C1-C6 alkyl group, a halogenated C1-C6 alkyl group, a hydroxyl group, a hydroxy C1-C6 alkyl group, a C3-C7 cycloalkyl group, an amino group, a C1-C3 alkylamino group and a di-C1-C3 alkylamino group. Among these, a halogen atom or a C1-C6 alkyl group is preferred. Such a substituent is a chlorine atom, a fluorine atom or a methyl group.

Examples of $Ar^2$ can include a 1,2,4-thiadiazol-5-yl group, a 1,3-thiazol-4-yl group, a pyrimidin-4-yl group, a 6-fluoropyrimidin-4-yl group and a 2-fluoropyrimidin-4-yl group. Among them, a pyrimidin-4-yl group is more preferred.

The phenyl group constituting the benzenesulfonamide may have from 1 to 3 substituents. Examples of such substituents can include a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group and a cyano group. Among these, a halogen atom, a C1-C6 alkyl group or a halogenated C1-C6 alkyl group is preferred. One to three groups independently selected from a chlorine atom, a fluorine atom, a methyl group, an ethyl group, a trifluoromethyl group and a cyano group are more preferred. When the phenyl group has two or more such groups, the two or more groups may be the same or different from each other.

Examples of the optionally substituted phenyl group constituting the benzenesulfonamide can include a 3-methylphenyl group, a 3-chlorophenyl group, a 3-fluorophenyl group, a 2,3-difluorophenyl group, a 2,5-difluorophenyl group, a 2,6-difluorophenyl group, a 2-chloro-5-fluorophenyl group, a 5-chloro-2-fluorophenyl group, a 3-trifluoromethylphenyl group, a 2-fluoro-3-methylphenyl group, a 2-fluoro-5-methylphenyl group, a 5-ethyl-2-fluorophenyl group, a 3-cyanophenyl group and a 5-cyano-2-fluorophenyl group. Among these, a 2-fluorophenyl group, a 2,5-difluorophenyl group, a 5-chloro-2-fluorophenyl group or a 2-fluoro-3-methylphenyl group is preferred (here, the position number is indicated with the position bonded to the sulfonamide group as 1).

The cycloalkyl moiety can be any that from 5- to 7-membered cyclic alkyl but is preferably 5- or 6-membered cyclic alkyl.

This cycloalkyl group may have 1 or 2 substituents independently selected from the group consisting of a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group and a C1-C6 alkoxy group. Among these, a halogen atom, a C1-C6 alkyl group or a halogenated C1-C6 alkyl group is preferred. A fluorine atom or a methyl group is more preferred.

In the compound (I) used in the present invention, the aromatic group $Ar^1$ on the cycloalkyl group and the phenyloxy moiety having the sulfonamide group substitute on adjacent carbon atoms to form the following four isomers having a diastereomeric relationship, all of which are included in the present invention. Among these, the more preferred conformation is that of (1b).

[Formula 11]

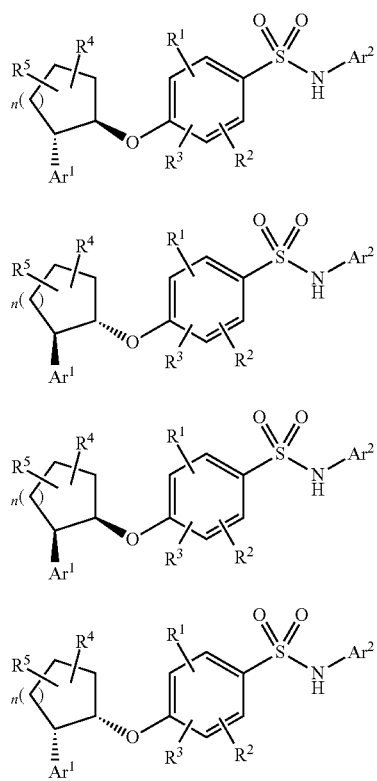

The compound represented by formula (I) used in the present invention may be in the form of a pharmacologically acceptable salt if desired. A pharmacologically acceptable salt means a salt that is not greatly toxic but may be used as a drug. This compound (I) may be changed into the form of a salt by causing a reaction between the compound and an acid if it has a basic group.

Examples of salts based on a basic substituent and a basic heteroaryl group include halogenated hydroacid salts such as hydrofluoride, hydrochloride, hydrobromide and hydroiodide; inorganic acid salts such as hydrochloride, nitrate, perchlorate, sulfate and phosphate; lower alkane sulfonates such as methanesulfonate, trifluoromethanesulfonate and ethanesulfonate; aryl sulfonates such as benzenesulfonate and p-toluenesulfonate; organic acid salts such as acetate, malate, fumarate, succinate, citrate, ascorbate, tartrate, oxalate and maleate; and amino acid salts such as glycine salt, lysine salt, arginine salt, ornithine salt, glutamate and aspartate. Among these, preferably, inorganic acid salts or aryl sulfonates are used, and more preferably, hydrochloride, benzenesulfonate or p-toluenesulfonate is used.

Examples of salts based on an acidic substituent include alkali metal salts such as sodium salt, potassium salt and lithium salt; alkali earth metal salts such as calcium salt and magnesium salt; metal salts such as aluminum salt and iron salt; inorganic salts such as ammonium salt; amine salts of organic salts such as t-octyl amine salt, dibenzylamine salt, morpholine salt, glucosamine salt, phenylglycine alkyl ester salt, ethylenediamine salt, N-methylglucamine salt, guanidine salt, diethylamine salt, triethylamine salt, dicyclohexylamine salt, N,N'-dibenzylethylenediamine salt, chloroprocaine salt, procaine salt, diethanolamine salt, N-benzylphenethylamine salt, piperazine salt, tetramethylammonium salt, tris(hydroxymethyl)aminomethane salt; and amino acid salts such as glycine salt, lysine salt, arginine salt, ornithine salt, glutamate and aspartate.

When the compound (I) is allowed to stand in air or recrystallized, it may absorb moisture to have absorbed water, so as to be changed into a hydrate, and such hydrates are also included in the salts of the present invention.

The compound (I) or a salt thereof sometimes absorbs a solvent of a given type so as to be changed into a solvate, and such a solvate is also included in the salt of the present invention.

The compound (I) has asymmetric carbon atoms in its molecule and thus includes optical isomers. These isomers and mixtures of these isomers are all represented by a single formula, i.e., formula (I). Accordingly, single optical isomers of the compound represented by formula (I) and mixtures of these optical isomers in any ratio are all included in the scope of the present invention.

An optical isomer as described above can be obtained by synthesizing the compound according to the present invention by using optically active starting compound or using the approach of asymmetric synthesis or asymmetric induction. Alternatively, an optical isomer can be obtained by isolation from the synthesized compound according to the present invention by using a general optical resolution method or, for example, a separation method using an optically active carrier.

The compound (I) may also contain, in a non-natural ratio, atomic isotope(s) of one or more of the atoms constituting this compound. Examples of atomic isotope(s) include deuterium ($^2H$), tritium ($^3H$), iodine-125 ($^{125}I$) and carbon-14 ($^{14}C$). Moreover, the compound may be radiolabeled with a radioisotope such as tritium ($^3H$), iodine-125 ($^{125}I$) or carbon-14 ($^{14}C$) Such a radiolabeled compound is useful as therapeutic or preventive agents, research reagents, for example, assay reagents, and diagnostic agents, for example, in vivo image diagnostic agents. All isotopic variants of the present compound are included in the scope of the present invention regardless of whether or not they are radioactive.

The compound represented by formula (I) or a pharmacologically acceptable salt thereof used in the present invention has excellent voltage-gated sodium channel 1.7 (Nav 1.7) inhibitory activities and has excellent subtype selectivity, and hence serves as an excellent drug for a respiratory disease in warm-blooded animals (preferably mammals including humans).

Accordingly, the present compound and a pharmacologically acceptable salt thereof have excellent treatment efficacy and/or preventive efficacy for the following diseases or symptoms:

asthma; cystic fibrosis; bronchitis; chronic bronchitis; bronchial asthma; bronchiectasis; chronic obstructive pulmonary disease (COPD); cough; acute respiratory distress syndrome (ARDS); pulmonary tuberculosis; interstitial pneumonia; pleuritis; pneumonia; emphysema; pneumoconiosis; diffuse panbronchiolitis; rheumatism; silicosis; spontaneous pneumothorax; cold syndrome; pulmonary embolism; pulmonary infarction; and dry cough.

The compound of formula (I) or a pharmacologically acceptable salt thereof used in the present invention can be an excellent antitussive for various respiratory diseases and serves as an excellent antitussive by application to, for example, bronchial asthma, asthmatic bronchitis, acute bronchitis, chronic bronchitis, cold, bronchiectasis, pneumonia, pulmonary tuberculosis, upper respiratory inflammation, laryngopharyngitis, nasal catarrh, bronchitis, asthmatic bronchitis, or cough associated with bronchial asthma. The compound can further provide an excellent method for treating and/or preventing bronchial asthma, asthmatic bronchitis, acute bronchitis, chronic bronchitis, cold, bronchiectasis, pneumonia, pulmonary tuberculosis, upper respiratory inflammation, laryngopharyngitis, nasal catarrh, bronchitis, asthmatic bronchitis, or cough associated with bronchial asthma.

The present compound shows excellent sodium channel inhibitory activities and can thus be expected to further show excellent treatment efficacy and/or preventive efficacy for dysuria, multiple sclerosis, interstitial cystitis, cystalgia syndrome, irritable colon syndrome, dysuric multiple sclerosis, arrhythmia, myotonia, numbness, brain infarction and the like.

The compound or a pharmacologically acceptable salt thereof used in the present invention can be administered in various forms. Examples of routes of administration include oral administration using tablets, capsules, granules, emulsions, pills, powders, syrups (solutions) and the like, and parenteral administration using injections (intravenous, intramuscular, subcutaneous or intraperitoneal administration), drip infusions, suppositories (rectal administration) and the like. These various formulations can be prepared as drug products according to usually employed methods by appropriately selecting and using aids generally used in the field of pharmaceutical formulation, such as excipients, binders, disintegrants, lubricants, flavoring agents, dissolving aids, suspending agents and coating agents, to be added to an active ingredient.

When used as a tablet, examples of a usable carrier include excipients such as lactose, saccharose, sodium chloride, glucose, urea, starch, calcium carbonate, kaolin, crystalline cellulose and silicic acid; binders such as water, ethanol, propanol, simple syrup, a glucose solution, a starch solution, a gelatin solution, carboxymethylcellulose, shellac, methylcellulose, potassium phosphate and polyvinylpyrrolidone; disintegrants such as dry starch, sodium alginate, powdered agar, powdered laminaran, sodium hydrogencarbonate, calcium carbonate, polyoxyethylene sorbitan fatty acid ester, sodium lauryl sulfate, stearic monoglyceride, starch and lactose; disintegration inhibitors such as saccharose, stearin, cocoa butter and hydrogenated oil; absorption enhancers such as quaternary ammonium salt and sodium lauryl sulfate; humectants such as glycerine and starch; adsorbents such as starch, lactose, kaolin, bentonite and colloidal silicic acid; and lubricants such as purified talc, stearate, powdered boric acid and polyethylene glycol. Furthermore, tablets having general coating, for example, sugar-coated tablets, gelatin-coated tablets, enteric-coated tablets, film-coated tablets, double-layer tablets and multilayered tablets can be prepared as required.

When used as a pill, examples of a usable carrier include excipients such as glucose, lactose, cocoa butter, starch, hydrogenated vegetable oil, kaolin and talc; binders such as powdered gum arabic, powdered tragacanth, gelatin and ethanol; and disintegrants such as laminaran and agar.

When used as a suppository, a wide range of carriers conventionally known in this field can be used, and examples include polyethylene glycol, cocoa butter, higher alcohols, higher alcohol esters, gelatin and semisynthetic glycerides.

When used as an injection, the formulations can be prepared as a solution, an emulsion or a suspension. These solution, emulsion and suspension are preferably sterilized and isotonic with blood. The solvent used for producing these solutions, emulsions and suspensions is not particularly limited so long as it can be used as a diluent for medical use, and examples of the solvent include water, ethanol, propylene glycol, ethoxylated isostearyl alcohol, polyoxylated isostearyl alcohol and polyoxy ethylene sorbitan fatty acid esters. In this case, a sufficient amount of sodium chloride, glucose or glycerine may be included in the formulation to prepare an isotonic solution, and general dissolving aids, buffers, soothing agents and the like may also be included.

Furthermore, coloring agents, preservatives, perfumes, flavoring agents, sweeteners and the like can be added to the above-mentioned formulations if necessary. Moreover, other pharmaceuticals can also be added.

The amount of active ingredient compound contained in the formulations is not particularly limited but is widely and appropriately selected, and is generally 0.5 to 70% by weight and preferably 1 to 30% by weight of the whole composition.

The dose varies depending on the symptoms, age and the like of a patient (a warm-blooded animal, in particular, a human). In the case of oral administration, a daily dosage for an adult is from a lower limit of 0.1 mg (preferably 1 mg and more preferably 10 mg) to an upper limit of 2000 mg (preferably 100 mg), which is administered dividedly as 1 to 6 doses depending upon the symptoms.

The compound represented by formula (I) used in the present invention can be produced in accordance with methods A to C described below. The compound represented by formula (V) can be produced in accordance with methods D to H.

Solvents used in the reactions of the respective steps of methods A to K below are not particularly limited as long as they do not inhibit the reactions but dissolve to some extent compounds involved in the reactions. The solvents are selected from, for example, the group consisting of the following solvents. Alternatively, the solvents may be mixtures thereof. The group of usable solvents consists of hydrocarbons such as pentane, hexane, octane, petroleum ether, ligroin and cyclohexane; amides such as formamide, N,N-dimethylformamide, N,N-dimethylacetamide, N-methyl-2-pyrrolidone, N-methyl-2-pyrrolidinone and hexamethylphosphoric triamide; ethers such as diethyl ether, diisopropyl ether, tetrahydrofuran, dioxane, dimethoxyethane and diethylene glycol dimethyl ether; alcohols such as methanol, ethanol, n-propanol, isopropanol, n-butanol, 2-butanol, 2-methyl-1-propanol, t-butanol, isoamyl alcohol, diethylene glycol, glycerin, octanol, cyclohexanol and methyl cellosolve; sulfoxides such as dimethyl sulfoxide; sulfones such as sulfolane; nitriles such as acetonitrile, propionitrile, butyronitrile and isobutyronitrile; esters such as ethyl formate, ethyl acetate, propyl acetate, butyl acetate and diethyl carbonate; ketones such as acetone, methyl ethyl ketone, 4-methyl-2-pentanone, methyl isobutyl ketone, isophorone and cyclohexanone; nitro compounds such as nitro ethane and nitro benzene; halogenated hydrocarbons such as dichloromethane, 1,2-dichloroethane, chlorobenzene, dichlorobenzene, chloroform and carbon tetrachloride; aromatic hydrocarbons such as benzene, toluene and xylene; carboxylic acids such as acetic acid, formic acid, propionic acid, butyric acid and trifluoroacetic acid; and water.

Examples of bases used in the reactions described below include alkali metal carbonates such as sodium carbonate, potassium carbonate, lithium carbonate and cesium carbonate; alkali metal hydrogencarbonates such as sodium hydrogencarbonate, potassium hydrogencarbonate and lithium hydrogencarbonate; alkali metal hydrides such as lithium hydride, sodium hydride and potassium hydride; alkali metal hydroxides such as sodium hydroxide, potassium hydroxide, barium hydroxide and lithium hydroxide; inorganic bases of alkali metal fluorides such as sodium fluoride and potassium fluoride; alkali metal alkoxides such as sodium methoxide, sodium ethoxide, sodium-t-butoxide, potassium methoxide, potassium ethoxide, potassium-t-butoxide and lithium methoxide; alkali metal trialkyl siloxides such as sodium trimethylsiloxide, potassium trimethylsiloxide and lithium trimethylsiloxide; mercaptan alkali metals such as methyl mercaptan sodium and ethyl mercaptan sodium; organic bases such as N-methyl morpholine, triethylamine, tripropylamine, tributylamine, diisopropylethylamine, dicyclohexylamine, N-methylpiperidine, pyridine, 4-pyrrolidinopyridine, picoline, 4-(N,N-dimethylamino)pyridine, 2,6-di (t-butyl)-4-methylpyridine, quinoline, N,N-dimethylaniline, N,N-diethylaniline, 1,5-diazabicyclo[4.3.0]nona-5-ene (DBN), 1,4-diazabicyclo[2.2.2]octane (DABCO) and 1,8-diazabicyclo[5.4.0]undeca-7-ene (DBU); and organometallic bases such as butyl lithium, lithium diisopropylamide and lithium bis(trimethylsilyl)amide.

Examples of acids used in the reactions described below include: inorganic acids such as hydrochloric acid, sulfuric acid, nitric acid, perchloric acid, hypochlorous acid, phosphoric acid, boric acid, hydrofluoric acid, tetrafluoroboric acid and fluorosulfonic acid; organic acids such as formic acid, acetic acid, oxalic acid, citric acid, gluconic acid, lactic acid, tartaric acid, benzoic acid, methanesulfonic acid, benzenesulfonic acid, p-toluenesulfonic acid and trifluoromethanesulfonic acid; and Lewis acids such as boron trifluoride, a boron trifluoride-diethyl ether complex, a boron trifluoride-dimethyl sulfide complex, a boron trifluoride-pyridine complex, a boron trifluoride-tetrahydrofuran complex, boron trichloride, boron triiodide, trimethylaluminum, triethylaluminum and titanium tetrachloride.

Examples of palladium catalysts used in the reactions described below include divalent or zero-valent palladium catalysts such as tetrakis (triphenylphosphine) palladium (0), palladium-activated carbon, palladium hydroxide-activated carbon, palladium (II) acetate, palladium (II) trifluoroacetate, palladium black, palladium (II) bromide, palladium (II) chloride, palladium (II) iodide, palladium (II) cyanide, palladium (II) nitrate, palladium (II) oxide, palladium (II) sulfate, dichlorobis(acetonitrile) palladium (II), dichlorobis(benzonitrile) palladium (II), dichloro(1,5-cyclooctadiene) palladium (II), acetylacetone palladium (II), palladium (II) sulfide, [1,1'-bis(diphenylphosphino)ferrocene]palladium (II) dichloride, [1,2-bis(diphenylphosphino) ethane]palladium (II), dichloride tris(dibenzylidene-acetone)dipalladium (0), tetrakis(acetonitrile) palladium (II) tetrafluoroborate and an aryl chloride-palladium dimer.

Examples of copper catalysts used in the reactions described below include zero-valent, monovalent or divalent copper catalysts and complexes thereof, such as copper, copper (I) chloride, copper (I) bromide, copper (I) iodide, copper (I) trifluoromethanesulfonate, a copper (I) bromide-dimethyl sulfide complex, copper (II) bromide, copper (II) acetate, copper (II) sulfate and copper (II) acetate.

Examples of ligands of the copper catalyst used in the reactions described below include diamine ligands, such as N,N'-dimethylethylenediamine, trans-N,N'-dimethylcyclohexane-1,2-diamine, 2-(diphenylphosphino)-2'-(N,N-dimethylamino)biphenyl, 1,10-phenanthroline and N,N'-dimethyl-1,2-cyclohexanediamine.

Examples of dehydrogenation or halogen metal exchange reagents used in the reactions described below include: alkyl alkali metals such as methyl lithium, ethyl lithium, isopropyl lithium, n-butyl lithium, sec-butyl lithium and tert-butyl lithium; alkyl magnesium halides such as methyl magnesium chloride, methyl magnesium bromide, ethyl magnesium chloride, ethyl magnesium bromide, isopropyl magnesium chloride and isopropyl magnesium bromide; and organic metal bases such as lithium diisopropylamide, lithium tetramethylpiperidine and lithium bis(trimethylsilyl) amide.

Examples of hydroboration reagents used in the reactions described below include: borane complexes such as a borane-tetrahydrofuran complex, a borane-dimethyl sulfide complex, a borane-dimethylamine complex and a borane-morpholine complex; and dialkyl borane such as isopinocampheylborane, disiamylborane and 9-borabicyclo[3,3,1]nonane.

Examples of oxidation reagents used in the reactions described below include hydrogen peroxide water and sodium perborate tetrahydrate.

Examples of epoxidation reagents used in the reaction of step F1 described below include: peracids such as 3-chloroperbenzoic acid, perbenzoic acid and peracetic acid; peroxides such as t-butyl hydroperoxide (TBHP) and hydrogen peroxide; and potassium peroxymonosulfate.

Examples of reducing agents used in the reactions described below include: alkali metal borohydrides such as sodium borohydride, lithium borohydride, sodium cyanoborohydride and sodium triacetoxyborohydride; borane complexes such as a borane-tetrahydrofuran complex and a borane-dimethyl sulfide complex; aluminum hydride compounds such as diisobutyl aluminum hydride, lithium aluminum hydride and lithium ethoxide aluminium hydride; and alkali metals such as sodium tellurium hydride, diisobutyl aluminum hydride and sodium bis(methoxyethoxy) aluminum hydride.

In the reactions conducted in each step of methods A to I, the reaction temperature is varied depending on the solvent, starting material, reagent and the like, and the reaction time is varied depending on the solvent, starting material, reagent, reaction temperature and the like.

In the reactions conducted in each step of methods A to I, after completing the reaction, the target compound is collected from the reaction mixture according to a method generally employed in this technical field. For example, the reaction mixture is appropriately neutralized, and if there is an insoluble material, it is removed by filtration. Thereafter, water and a water-nonmiscible organic solvent such as ethyl acetate are added to the resultant, so as to separate an organic layer containing the target compound. The organic layer is washed with water or the like, dried over anhydrous magnesium sulfate, anhydrous sodium sulfate, anhydrous sodium hydrogencarbonate or the like, and filtered, and the solvent is evaporated, so as to yield the target compound.

The thus obtained target compound may, if necessary, be separated and purified by a method generally employed in this technical field, for example, by an appropriate combination of methods usually employed for separation/purification of an organic compound, such as recrystallization and reprecipitation, followed by elution with an appropriate eluent by using chromatography. If the target compound is insoluble in a solvent, it may be purified by washing a solid crude product with a solvent. Alternatively, the target compound of each step may be used as it is, in a following reaction without purification.

Next, the reactions conducted in respective steps of methods A to K will be described.

Method A is a method for producing the compound represented by formula (I).

[Method A]

[Formula 12]

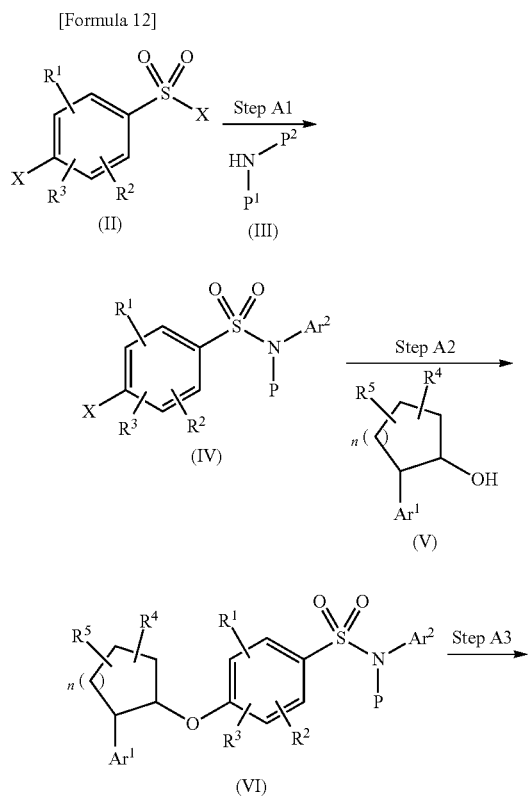

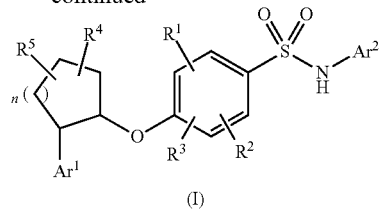

In the present specification, $Ar^1$, $Ar^2$, $R^1$, $R^2$, $R^3$, $R^4$, $R^5$ and n represent the same as defined above, P, $P^1$, $P^2$, $P^3$ and $P^4$, each represents a protecting group, X represents a halogen atom, Y represents a substituent that can work as a nucleophile or an electrophile in a cross-coupling reaction caused by a transition-metal catalyst, such as a halogen atom, a substituent including a boron atom, or a substituent including a tin atom.

P, $P^1$ or $P^2$ is not particularly limited as long as it is a protecting group generally used for an amino group. Examples thereof include a formyl group, a phenylcarbonyl group, a methoxycarbonyl group, an ethoxycarbonyl group, a t-butoxycarbonyl group, a phenyloxycarbonyl group, a 9-fluorenylmethyloxycarbonyl group, an adamantyloxycarbonyl group, a benzyloxycarbonyl group, a benzylcarbonyl group, a benzyl group, a 2,4-dimethoxybenzyl group, a benzhydryl group, a trityl group and a phthaloyl group.

$P^3$ and $P^4$ are not particularly limited as long as they can form an acetal generally used as a protecting group for a carbonyl group, and are, for example, methyl or ethyl groups, or $P^3$ and $P^4$ may form a cyclic structure to constitute a 1,3-dioxane or 1,3-dioxolane ring.

Y is not particularly limited as long as it is used as a substituent that can work as a nucleophile or an electrophile in a cross-coupling reaction caused by a transition-metal catalyst. Examples thereof include an iodo group, a bromo group, a chloro group, a boronyl group and a tributylstannyl group.

Step A1

This step is the step of producing a compound represented by formula (IV).

This step is conducted by causing a reaction, in a solvent and in the presence of a base, between a compound represented by formula (II) and a compound represented by formula (III).

The compound represented by formula (II) and the compound represented by formula (III) used in this step are known compounds or may be easily produced from known compounds used as starting materials by known methods or methods similar to known methods.

The solvent used in this step is preferably any one of ethers, nitriles or halogenated hydrocarbons, and more preferably, tetrahydrofuran, acetonitrile or dichloromethane.

The base used in this step is preferably any one of alkali metal carbonates or organic bases, and more preferably, potassium carbonate, pyridine, 4-(N,N-dimethylamino)pyridine, 1,4-diazabicyclo[2.2.2]octane (DABCO), LiHMDS or 1,8-diazabicyclo[5.4.0]undec-7-ene (DBU).

The reaction temperature to be employed in this step is generally 0° C. to 100° C. and preferably 0° C. to room temperature.

The reaction time of this reaction is from 0.5 hours to 48 hours, and the reaction is generally completed in approximately 1 hour to approximately 24 hours.

Step A2

This step is the step of producing a compound represented by formula (VI).

This step is conducted by causing a reaction, in a solvent and in the presence of a base, between the compound represented by formula (IV) and a compound represented by formula (V).

The solvent used in this step is preferably any one of ethers or amides, and more preferably, tetrahydrofuran or N,N-dimethylformamide.

The base used in this step is preferably any one of alkali metal alkoxides, alkali metal hydrides or alkali metal hydroxides, and more preferably, sodium t-butoxide, potassium t-butoxide, sodium methoxide, potassium methoxide, sodium hydride, potassium hydride, sodium hydroxide or potassium hydroxide.

The reaction temperature to be employed in this step is generally 0° C. to 200° C. and preferably 0° C. to room temperature.

The reaction time of this reaction is from 0.5 hours to 48 hours, and the reaction is generally completed in approximately 1 hour to approximately 24 hours.

Step A3

This step is the step of producing the compound represented by formula (I).

This step is conducted by causing a reaction, in a solvent and, if desired, in the presence of a scavenger, between an acid and the compound represented by formula (VI).

The solvent used in this step is preferably any one of ethers or halogenated hydrocarbons, and more preferably, tetrahydrofuran, 1,4-dioxane or dichloromethane.

The scavenger used in this step is preferably trialkylsilane or aryl ether, and more preferably, triethylsilane or anisole.

The acid used in this step is preferably an organic acid or an inorganic acid, and more preferably, trichloroacetic acid, trifluoroacetic acid, acetic acid, sulfuric acid or hydrochloric acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Also, this step is conducted by deprotecting the compound represented by formula (VI) in a solvent and in the presence of a palladium catalyst under a hydrogen atmosphere.

The solvent used in this case is preferably any one of ethers or alcohols, and more preferably, tetrahydrofuran, methanol or ethanol.

The catalyst is preferably a zero-valent palladium catalyst, and more preferably, palladium-activated carbon or palladium hydroxide-activated carbon.

The reaction temperature is generally −20° C. to 120° C. and preferably 0° C. to 80° C.

The reaction time of this reaction is from 1 hour to 48 hours, and the reaction is generally completed in approximately 2 hours to approximately 24 hours.

A compound represented by formula (Ia) or (Ib) is an optical isomer of the compound represented by formula (I) and is produced by combining method A with method B described below.

Method B is a method for producing optical isomers (VIa) and (VIb) of the compound (VI) by optical resolution after step A2 in method A. The compound represented by formula (Ia) or (Ib) is produced through step A3 from the optical isomer (VIa) or (VIb).

[Method B]

[Formula 13]

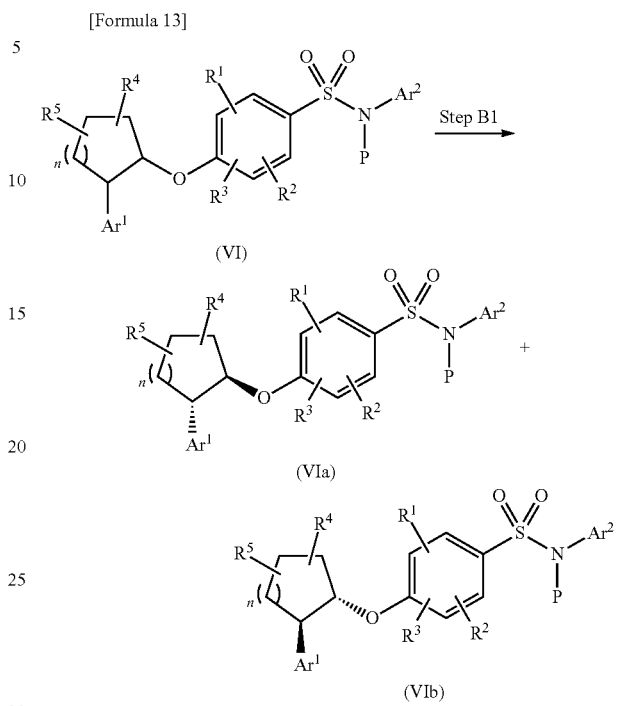

In the above formulas, $Ar^1$, $Ar^2$, $R^1$, $R^2$, $R^3$, $R^4$, $R^5$, P and n represent the same as defined above.

Step B1

This step is the step of producing the compounds represented by formulas (VIa) and (VIb). This step is conducted by optically resolving the compound represented by formula (VI) into the compounds represented by (VIa) and (VIb) by using a chiral column.

The solvent used in this step is preferably any one of hydrocarbons, alcohols or mixed solvents thereof, and more preferably, a mixed solvent of hexane and isopropanol or a mixed solvent of hexane and ethanol.

The column used in the optical resolution is not particularly limited as long as it is a chiral column capable of optical resolution. CHIRALPAK (registered trademark) AD-H or CHIRALPAK (registered trademark) IC manufactured by Daicel Corp. is preferred.

The temperature to be employed in this step is generally 0° C. to 40° C. and preferably 0° C. to room temperature.

Method C is another method for producing the compound represented by formula (I).

[Method C]

[Formula 14]

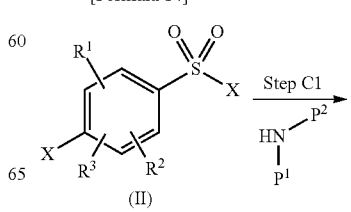

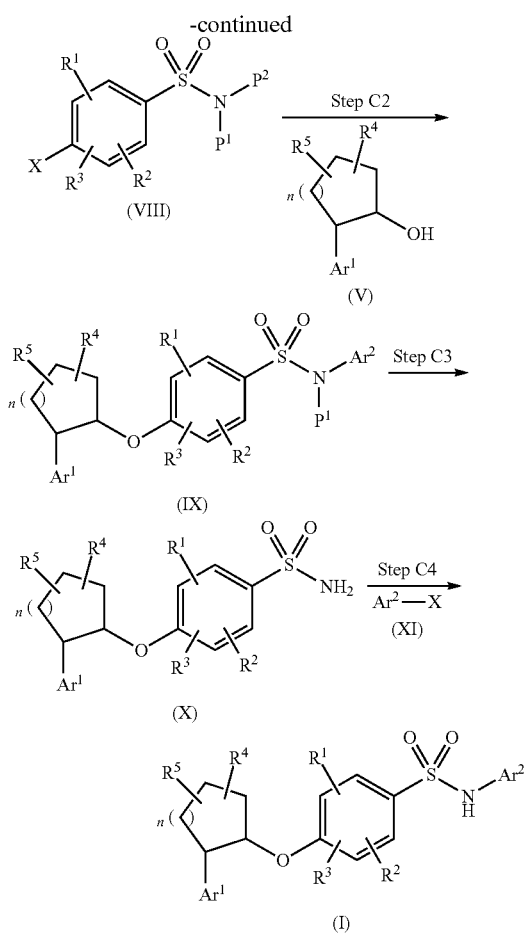

In the above formulas, $Ar^1$, $Ar^2$, $R^1$, $R^2$, $R^3$, $R^4$, $R^5$, $P^1$, $P^2$, X and n represent the same as defined above.

Step C1

This step is the step of producing a compound represented by formula (VIII).

This step is conducted by causing a reaction, in a solvent and in the presence of a base, between a compound represented by formula (II) and a compound represented by formula (VII).

The compound represented by formula (II) and the compound represented by formula (VII) used in this step are known compounds or may be easily produced from known compounds used as starting materials by known methods or methods similar to known methods.

The solvent used in this step is preferably any one of ethers, nitriles or halogenated hydrocarbons, and more preferably, tetrahydrofuran, acetonitrile or dichloromethane.

The base used in this step is preferably any one of alkali metal carbonates or organic bases, and more preferably, potassium carbonate, pyridine, 4-(N,N-dimethylamino)pyridine, 1,4-diazabicyclo[2.2.2]octane (DABCO), LiHMDS or 1,8-diazabicyclo[5.4.0]undec-7-ene (DBU).

The reaction temperature to be employed in this step is generally 0° C. to 100° C. and preferably 0° C. to room temperature.

The reaction time of this reaction is from 0.5 hours to 48 hours, and the reaction is generally completed in approximately 1 hour to approximately 24 hours.

Step C2

This step is the step of producing a compound represented by formula (IX).

This step is conducted by causing a reaction, in a solvent and in the presence of a base, between the compound represented by formula (V) and the compound represented by formula (VIII).

The solvent used in this step is preferably any one of ethers or amides, and more preferably, tetrahydrofuran or N,N-dimethylformamide.

The base used in this step is preferably any one of alkali metal alkoxides, alkali metal hydrides or alkali metal hydroxides, and more preferably, sodium t-butoxide, potassium t-butoxide, sodium methoxide, potassium methoxide, sodium hydride, potassium hydride, sodium hydroxide or potassium hydroxide.

The reaction temperature to be employed in this step is generally 0° C. to 200° C. and preferably 0° C. to room temperature.

The reaction time of this reaction is from 0.5 hours to 48 hours, and the reaction is generally completed in approximately 1 hour to approximately 24 hours.

Step C3

This step is the step of producing a compound represented by formula (X).

This step is conducted by causing a reaction, in a solvent and, if desired, in the presence of a scavenger, between an acid and the compound represented by formula (IX).

The solvent used in this step is preferably any one of ethers or halogenated hydrocarbons, and more preferably, tetrahydrofuran, 1,4-dioxane or dichloromethane.

The scavenger used in this step is preferably trialkylsilane or aryl ether, and more preferably, triethylsilane or anisole.

The acid used in this step is preferably an organic acid or an inorganic acid, and more preferably, trichloroacetic acid, trifluoroacetic acid, acetic acid, sulfuric acid or hydrochloric acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Alternatively, this step is also conducted by deprotecting the compound represented by formula (IX) in a solvent and in the presence of a palladium catalyst under a hydrogen atmosphere.

The solvent used in this case is preferably any one of ethers or alcohols, and more preferably, tetrahydrofuran, methanol or ethanol.

The catalyst used is preferably a zero-valent palladium catalyst, and more preferably, palladium-activated carbon or palladium hydroxide-activated carbon.

The reaction temperature is generally −20° C. to 120° C. and preferably 0° C. to 80° C.

The reaction time is generally 1 hour to 48 hours and preferably 2 hours to 24 hours.

Step C4

This step is the step of producing the compound represented by formula (I).

This step is conducted by causing a reaction, in a solvent and in the presence of a base, between the compound represented by formula (X) and a compound represented by formula (XI). This step may be conducted in the presence of a copper catalyst and a ligand thereof.

The compound represented by formula (XI) used in this step is a known compound or may be easily produced from known compounds used as starting materials by known methods or methods similar to known methods.

The solvent used in this step is preferably any one of ethers, amides or halogenated hydrocarbons, and more preferably, tetrahydrofuran, N,N-dimethylformamide or dichloromethane.

The base used in this step is preferably any one of organic bases or alkali metal carbonates, and more preferably, triethylamine, cesium carbonate or potassium carbonate.

The copper catalyst used in this step is preferably copper (I) chloride, copper (I) bromide, copper (I) iodide or copper (I) trifluoromethanesulfonate.

The ligand used in this step is preferably N,N'-dimethylethylenediamine, trans-N,N'-dimethylcyclohexane-1,2-diamine or N,N'-dimethyl-1,2-cyclohexanediamine.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

The compound represented by formula (V) can be produced in accordance with methods D to H.

Method D is a method for producing the compound represented by formula (V).

[Method D]

[Formula 15]

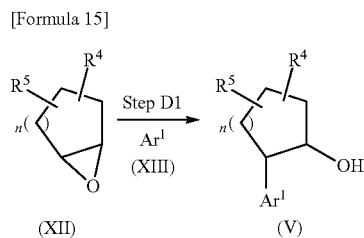

In the above formulas, $Ar^1$, $R^4$, $R^5$ and n represent the same as defined above.

Step D1

This step is the step of producing the compound represented by formula (V).

This step is conducted by converting a compound represented by formula (XIII) to a metal salt by deprotonation or halogen metal exchange in a solvent and then reacting the metal salt with a compound represented by formula (XII).

The compound represented by formula (XII) and the compound represented by formula (XIII) used in this step are known compounds or may be easily produced from known compounds used as starting materials by known methods or methods similar to known methods.

The solvent used in this step is preferably any one of ethers, hydrocarbons or halogenated hydrocarbons, and more preferably, tetrahydrofuran, toluene or dichloromethane.

The deprotonation or halogen metal exchange reagent used in this step is preferably alkyl magnesium halide or alkyl alkali metal, and more preferably, n-butyl lithium, sec-butyl lithium or isopropyl magnesium chloride.

The reaction temperature to be employed in this step is generally −100° C. to 100° C. and preferably −80° C. to room temperature.

The reaction time of this reaction is from 0.5 hours to 48 hours, and the reaction is generally completed in approximately 1 hour to approximately 24 hours.

Method E is another method for producing the compound represented by formula (V).

[Method E]

[Formula 16]

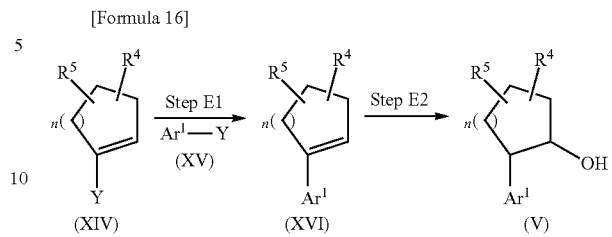

In the above formulas, $Ar^1$, $R^4$, $R^5$, Y and n represent the same as defined above.

Step E1

This step is the step of producing a compound represented by formula (XVI).

This step is conducted by causing a reaction, in a solvent and in the presence of a catalyst, between a compound represented by formula (XIV) and a compound represented by formula (XV).

The compounds represented by formulas (XIV) and (XV) used in this step are known compounds or may be easily produced from known compounds used as starting materials by known methods or methods similar to known methods.

The solvent used in this step is preferably any one of ethers, amides, water or mixed solvents thereof, and more preferably, a mixed solvent of 1,4-dioxane and water, tetrahydrofuran or N,N-dimethylformamide.

The catalyst used in this step is preferably a zero-valent palladium catalyst or a divalent palladium catalyst, and more preferably, tetrakis(triphenylphosphine)palladium (0), [1,1'-bis(diphenylphosphino)ferrocene]palladium (II) dichloride or [1,2-bis(diphenylphosphino)ethane]palladium (II) dichloride.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Step E2

This step is the step of producing the compound represented by formula (V).

This step is conducted by hydroborating the compound represented by formula (XVI) in a solvent, followed by oxidation.

The solvent used in this step is preferably any one of ethers, and more preferably, 1,4-dioxane or tetrahydrofuran.

The hydroboration agent used in this step is preferably a borane-tetrahydrofuran complex or a borane-dimethyl sulfide complex.

The oxidizing agent used in this step is preferably hydrogen peroxide or sodium perborate tetrahydrate.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Method F is another method for producing the compound represented by formula (V).

[Method F]

[Formula 17]

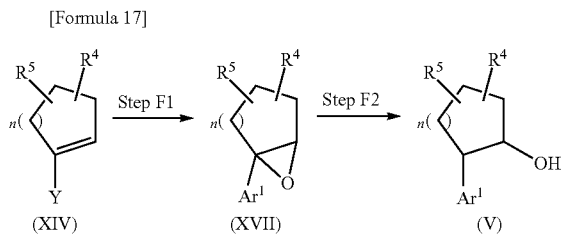

In the above formulas, $Ar^1$, $R^4$, $R^5$ and n represent the same as defined above.

Step F1

This step is the step of producing a compound represented by formula (XVII).

This step is conducted by epoxidizing the compound represented by formula (XVI) in a solvent.

The solvent used in this step is preferably any one of ketones or halogenated hydrocarbons, and more preferably, chloroform or dichloromethane.

The epoxidation reagent used in this step is preferably 3-chloroperbenzoic acid or potassium peroxymonosulfate.

The reaction temperature to be employed in this step is generally −20° C. to 120° C. and preferably 0° C. to 80° C.

The reaction time of this step is from 1 hour to 48 hours, and the reaction is generally completed in approximately 2 hours to approximately 24 hours.

Step F2

This step is the step of producing the compound represented by formula (V).

This step is conducted by reducing the compound represented by formula (XVII) in a solvent.

The solvent used in this step is preferably any one of ethers or alcohols, and more preferably, tetrahydrofuran, methanol or ethanol.

The reducing agent used in this step is preferably any one of alkali metal borohydrides or aluminum hydride compounds, and more preferably, sodium borohydride or lithium aluminum hydride.

The reaction temperature to be employed in this step is generally −20° C. to 120° C. and preferably 0° C. to 80° C.

The reaction time of this reaction is from 1 hour to 48 hours, and the reaction is generally completed in approximately 2 hours to approximately 24 hours.

This step is also conducted by reducing the compound represented by formula (XVII) in a solvent and in the presence of a catalyst under a hydrogen atmosphere or under a nitrogen atmosphere in the presence of a catalyst.

The solvent used in this step is preferably any one of ethers or alcohols, and more preferably, tetrahydrofuran, methanol or ethanol.

The catalyst used in this step is preferably a palladium catalyst or a nickel catalyst, and more preferably, palladium-activated carbon, palladium hydroxide-activated carbon or Raney nickel.

The reaction temperature to be employed in this step is generally 0° C. to 200° C. and preferably room temperature to 120° C.

The reaction time of this reaction is from 1 hour to 48 hours, and the reaction is generally completed in approximately 2 hours to approximately 24 hours.

Method G is another method for producing the compound represented by formula (V).

[Method G]

[Formula 18]

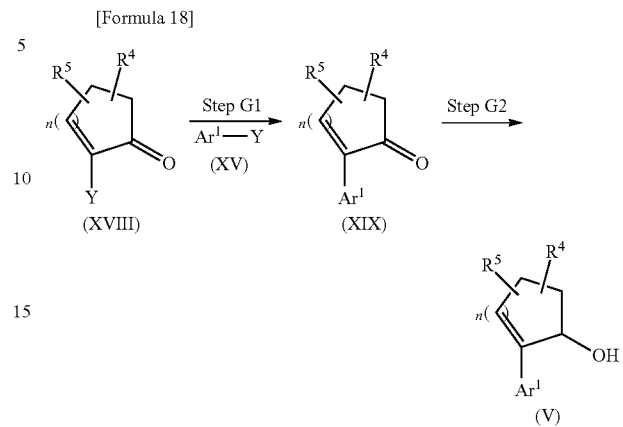

In the above formulas, $Ar^1$, $R^4$, $R^5$, $P^1$, $P^2$, Y and n represent the same as defined above.

Step G1

This step is the step of producing a compound represented by formula (XIX).

This step is conducted by causing a reaction, in a solvent and in the presence of a catalyst, between a compound represented compound represented by formula (XVIII) and a compound represented by formula (XV).

The compounds represented by formulas (XVIII) and (XV) used in this step are known compounds or may be easily produced from known compounds used as starting materials by known methods or methods similar to known methods.

The solvent used in this step is preferably any one of ethers, amides, water or mixed solvents thereof, and more preferably, a mixed solvent of 1,4-dioxane and water, tetrahydrofuran or N,N-dimethylformamide.

The catalyst used in this step is preferably a zero-valent palladium catalyst or a divalent palladium catalyst, and more preferably, tetrakis(triphenylphosphine)palladium (0), [1,1′-bis(diphenylphosphino)ferrocene]palladium (II) dichloride or [1,2-bis(diphenylphosphino)ethane]palladium (II) dichloride.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Step G2

This step is the step of producing the compound represented by formula (V).

This step is conducted by reducing the compound represented by formula (XIX) in a solvent.

The solvent used in this step is preferably any one of ethers or alcohols, and more preferably, tetrahydrofuran, ethanol or methanol.

The reducing agent used in this step is preferably any one of alkali metal borohydrides or aluminum hydride compounds, and more preferably, sodium borohydride or lithium aluminum hydride.

The reaction temperature to be employed in this step is generally −20° C. to 120° C. and preferably 0° C. to 80° C.

The reaction time of this reaction is from 1 hour to 48 hours, and the reaction is generally completed in approximately 2 hours to approximately 24 hours.

This step is also conducted by reducing the compound represented by formula (XIX) in a solvent and in the presence of a catalyst under a hydrogen atmosphere or under a nitrogen atmosphere in the presence of a catalyst.

The solvent used in this step is preferably any one of ethers or alcohols, and more preferably, tetrahydrofuran, methanol or ethanol.

The catalyst used in this step is preferably a palladium catalyst or a nickel catalyst, and more preferably, palladium-activated carbon, palladium hydroxide-activated carbon or Raney nickel.

The reaction temperature to be employed in this step is generally 0° C. to 200° C. and preferably room temperature to 120° C.

The reaction time of this reaction is from 1 hour to 48 hours, and the reaction is generally completed in approximately 2 hours to approximately 24 hours.

A compound represented by formula (Va) or (Vb) is an optical isomer of the compound represented by formula (V) and is produced by combining methods D to G with method H described below.

Method H is a method for producing the optical isomers (Va) and (Vb) of the compound (V) by optical resolution. The compound represented by formula (Ia) or (Ib) is produced through steps A2 and A3 from the optical isomer (Va) or (Vb).

[Method H]

[Formula 19]

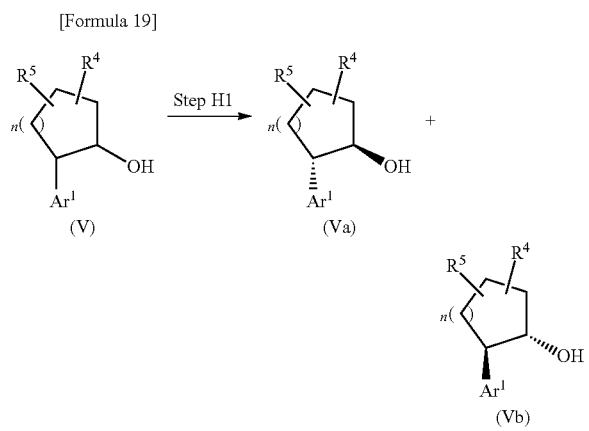

In the above formulas, $Ar^1$, $R^4$, $R^5$ and n represent the same as defined above.

Step H1

This step is the step of producing the compounds represented by formulas (Va) and (Vb). This step is conducted by optically resolving the compound represented by formula (V) into the compounds represented by formulas (Va) and (Vb) by using a chiral column.

The solvent used in this step is preferably any one of hydrocarbons, alcohols or mixed solvents thereof, and more preferably, a mixed solvent of hexane and isopropanol or a mixed solvent of hexane and ethanol.

The column used in the optical resolution can be any of those exemplified above.

The temperature to be employed in this step is generally 0° C. to 40° C. and preferably 0° C. to room temperature.

Method I is another method for producing the compound represented by formula (XVI).

[Formula 20]

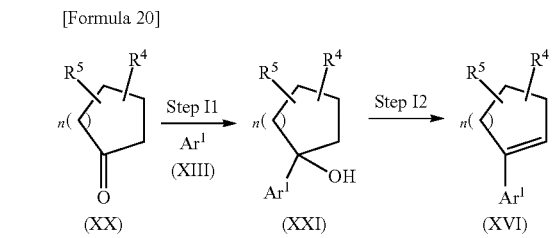

In the above formulas, $Ar^1$, $R^4$, $R^5$ and n represent the same as defined above.

Step I1

This step is the step of producing a compound represented by formula (XXI).

This step is conducted by converting a compound represented by formula (XIII) to a metal salt by deprotonation or halogen metal exchange in a solvent and then reacting the metal salt with a compound represented by formula (XX).

The compounds represented by formulas (XIII) and (XX) used in this step are known compounds or may be easily produced from known compounds used as starting materials by known methods or methods similar to known methods.

The solvent used in this step is preferably any one of ethers, hydrocarbons or halogenated hydrocarbons, and more preferably, tetrahydrofuran, toluene or dichloromethane.

The deprotonation or halogen metal exchange reagent used in this step is preferably alkyl magnesium halide or alkyl alkali metal, and more preferably, n-butyl lithium, sec-butyl lithium or isopropyl magnesium chloride.

The reaction temperature to be employed in this step is generally −100° C. to 100° C. and preferably −80° C. to room temperature.

The reaction time of this reaction is from 0.5 hours to 48 hours, and the reaction is generally completed in approximately hour to approximately 24 hours.

Step I2

This step is the step of producing the compound represented by formula (XVI).

This step is conducted by causing a reaction, in a solvent, between an acid and the compound represented by formula (XXI).

The solvent used in this step is preferably any one of alcohols, aromatic hydrocarbons or halogenated hydrocarbons, and more preferably, ethanol, toluene or dichloromethane.

The acid used in this step is preferably an organic acid or an inorganic acid, and more preferably, hydrochloric acid, sulfuric acid, acetic acid or p-toluenesulfonic acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

[Method J]

[Formula 21]

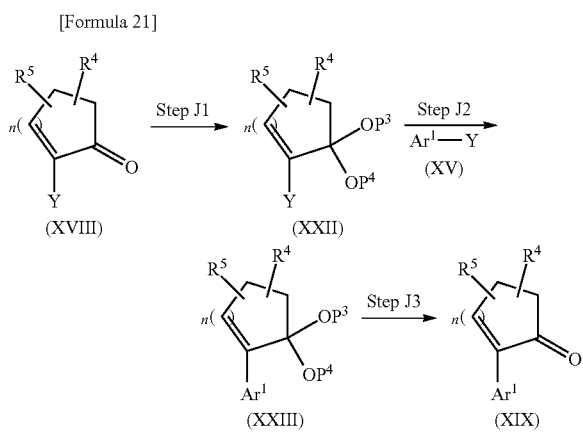

In the above formulas, $Ar^1$, $R^4$, $R^5$, $P^4$, $P^5$, Y and n represent the same as defined above.

Step J1

This step is the step of producing a compound represented by formula (XXII).

This step is conducted by causing a reaction, in a solvent and in the presence of a dehydrating agent or under dehydration conditions, between an acid and the compound represented by formula (XVIII).

The solvent used in this step is preferably any one of aromatic hydrocarbons, and more preferably, toluene or benzene.

The acid used in this step is preferably an organic acid or an inorganic acid, and more preferably, hydrochloric acid, sulfuric acid or p-toluenesulfonic acid.

The dehydrating agent used in this step is preferably an orthoester, and more preferably, hydrochloric acid or trimethoxymethane, trimethoxyethane or triethoxyethane.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Step J2

This step is the step of producing a compound represented by formula (XXIII).

This step is conducted by causing a reaction, in a solvent and in the presence of a catalyst, between the compound represented by formula (XXII) and a compound represented by formula (XV).

The compound represented by formula (XV) used in this step is a known compound or may be easily produced from known compounds used as starting materials by known methods or methods similar to known methods.

The solvent used in this step is preferably any one of ethers, amides, water or mixed solvents thereof, and more preferably, a mixed solvent of 1,4-dioxane and water, tetrahydrofuran or N,N-dimethylformamide.

The catalyst used in this step is preferably a zero-valent palladium catalyst or a divalent palladium catalyst, and more preferably, tetrakis(triphenylphosphine)palladium (0), [1,1'-bis(diphenylphosphino)ferrocene]palladium (II) dichloride or [1,2-bis(diphenylphosphino)ethane]palladium (II) dichloride.

The reaction temperature to be employed in this step is generally 0° C. to 150° C. and preferably room temperature to 120° C.

The reaction time of this reaction is from 0.5 hours to 60 hours, and the reaction is generally completed in approximately 1 hour to approximately 48 hours.

Step J3

This step is the step of producing the compound represented by formula (XIX).

This step is conducted by causing a reaction, in an aqueous solvent, between an acid and the compound represented by formula (XXIII).

The solvent used in this step is preferably any one of alcohols or ethers, and more preferably, ethanol, 1,4-dioxane or tetrahydrofuran.

The acid used in this step is preferably an organic acid or an inorganic acid, and more preferably, hydrochloric acid or sulfuric acid.

The reaction temperature to be employed in this step is generally 0° C. to 200° C. and preferably room temperature to 150° C.

The reaction time of this reaction is from 1 hour to 48 hours, and the reaction is generally completed in approximately 2 hours to approximately 24 hours.

Method K is another method for producing an optically active compound represented by formula (XVIIb) of the compound represented by formula (XVII). Also, an enantiomer thereof may be produced by appropriately selecting a reagent in step K1.

[Method K]

[Formula 22]

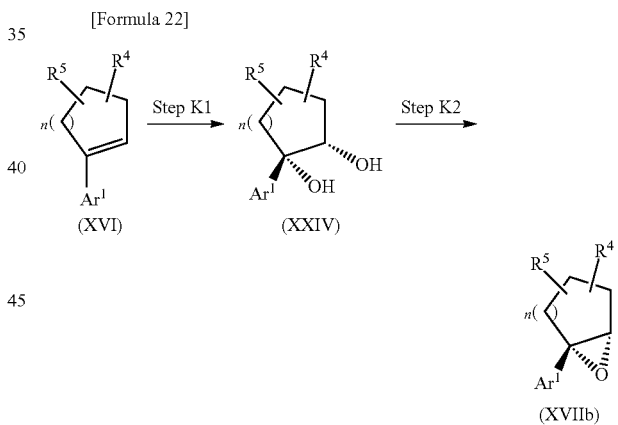

In the above formulas, $Ar^1$, $R^4$, $R^5$ and n represent the same as defined above.

Step K1

This step is the step of producing a compound represented by formula (XXIV).

This step is conducted by converting the compound represented by formula (XVI) to optically active diol in a solvent.

The solvent used in this step is preferably any one of alcohols, water or mixed solvents thereof, and more preferably, a mixed solvent of t-butanol and water.

The reagent for asymmetric conversion to diol used in this step is preferably AD-mixα or AD-mixβ (Sigma-Aldrich Corp.).

The reaction temperature to be employed in this step is generally −20° C. to 120° C. and preferably 0° C. to 80° C.

The reaction time of this step is on the order of 1 hour to 48 hours, and the reaction is generally completed in approximately 2 hours to approximately 24 hours.

Step K2

This step is the step of producing the compound represented by formula (XVIIb).

This step is conducted by subjecting the compound represented by formula (XXIV) to (I) a reaction with an orthoester in the presence of an acid, (II) a reaction with an acid halide in the presence of a base, or (III) a treatment with a base, in a solvent.

The solvent used in (I) is preferably any one of halogenated hydrocarbons, and more preferably, dichloromethane.

The acid used in (I) is preferably an inorganic acid or an organic acid, and more preferably, hydrochloric acid, sulfuric acid or p-toluenesulfonic acid.

The orthoester used in (I) is preferably trimethoxymethane, trimethoxyethane or triethoxyethane.

The reaction temperature to be employed in (I) is generally −20° C. to 120° C. and preferably 0° C. to 80° C.

The reaction time of (I) is from 1 hour to 96 hours, and the reaction is generally completed in approximately 2 hours to approximately 48 hours.

The solvent used in (II) is preferably any one of nitriles, and more preferably, acetonitrile.

The base used in (II) is preferably any one of alkali metal salts, and more preferably, potassium bromide, sodium bromide or lithium bromide.

The acid halide used in (II) is preferably acetic acid halide, formic acid halide or propionic acid halide, and more preferably, propionyl bromide or acetyl bromide.

The reaction temperature to be employed in (II) is generally −20° C. to 120° C. and preferably 0° C. to room temperature.

The reaction time of (II) is from 1 hour to 48 hours, and the reaction is generally completed in approximately 2 hours to approximately 24 hours.

The solvent used in (III) is preferably any one of alcohols, and more preferably, ethanol or methanol.

The base used in (III) is preferably any one of alkali metal carbonates, and more preferably, potassium carbonate, lithium carbonate or sodium carbonate.

The reaction temperature to be employed in (III) is generally −20° C. to 120° C. and preferably 0° C. to room temperature.

The reaction time of (III) is from 1 hour to 48 hours, and the reaction is generally completed in approximately 2 hours to approximately 24 hours.

EXAMPLES

The present invention will now be described in more detail with reference to examples and test examples, but the scope of the present invention is not limited to these examples.

In the examples described below, elution in column chromatography was performed under observation by TLC (Thin Layer Chromatography). In the TLC observation, silica gel 60F254 manufactured by Merck & Co. was adopted as a TLC plate; a solvent used as an eluting solvent in column chromatography was adopted as a developing solvent; and a UV detector was adopted as a detection method. Silica gel SK-85 (230-400 mesh) also manufactured by Merck & Co. or Chromatorex NH (200-350 mesh) manufactured by Fuji Silysia Chemical Ltd. was used as silica gel for columns. In addition to general column chromatography, an automatic chromatography apparatus (Purif-α2 or Purif-espoir2) manufactured by Shoko Scientific Co., Ltd. was appropriately used. A solvent described in each example was used as an eluting solvent at a specified ratio (or at a ratio changed appropriately if necessary). Abbreviations used in the examples mean the following:

mg: milligram, g: gram, mL: milliliter, MHz: megahertz.

In the examples described below, nuclear magnetic resonance (hereinafter, referred to as $^1$H-NMR) spectra were indicated in δ values (ppm) in terms of chemical shift values with tetramethylsilane used as standard. Splitting patterns were represented by s for singlet, d for doublet, t for triplet, q for quartet, m for multiplet, and br for broad.

Example 1

2,5-Difluoro-4-{[(1S*,2R*)-2-(1-methyl-1H-pyrazol-5-yl)cyclopentyl]oxy}-N-(pyrimidin-4-yl)benzenesulfonamide

[Formula 23]

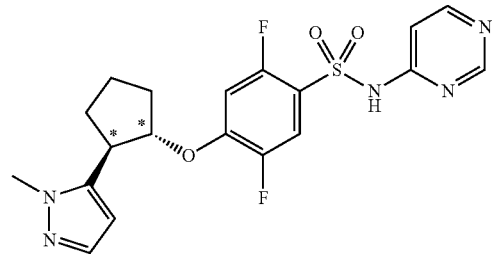

(1a) N-(2,4-Dimethoxybenzyl)pyrimidin-4-amine

A solution of 4-aminopyrimidine (20.0 g, 210 mmol), 2,4-dimethoxybenzaldehyde (69.9 g, 421 mmol) and piperidine (2.08 mL, 21.0 mmol) in toluene (1.0 L) was heated under reflux with stirring for 7 hours, and the solvent was subjected to azeotropic distillation to remove water. After allowing to cool, the reaction solution was diluted with ethanol (500 mL). Sodium borohydride (7.96 g, 210 mmol) was added thereto with cooling on ice, and the mixture was stirred at room temperature for 16 hours. To the reaction solution, water (500 mL) was added, and an organic layer was extracted. The thus obtained organic layer was dried over anhydrous sodium sulfate. After concentration under reduced pressure, the residue was purified with silica gel chromatography (ethyl acetate/methanol=95:5) to yield the title compound (27.0 g, 52%) as a colorless solid.

$^1$H-NMR (500 MHz, CDCl$_3$) δ ppm: 3.80 (3H, s), 3.84 (3H, s), 4.44 (2H, brs), 5.33 (1H, brs), 6.34 (1H, d, J=5.9 Hz), 6.44 (1H, dd, J=2.4, 8.3 Hz), 6.48 (1H, d, J=2.0 Hz), 7.18 (1H, d, J=8.3 Hz), 8.15 (1H, d, J=5.4 Hz), 8.55 (1H, s).

(1b) N-(2,4-Dimethoxybenzyl)-2,4,5-trifluoro-N-(pyrimidin-4-yl)benzenesulfonamide To a solution of the N-(2,4-dimethoxybenzyl)pyrimidin-4-amine (0.76 g, 3.10 mmol) prepared in Example 1a and 1,4-diazabicyclo[2.2.2]octane (0.70 g, 6.20 mmol) in acetonitrile (20 mL), 2,4,5-trifluorobenzenesulfonyl chloride (1.43 g, 6.20 mmol) was added with cooling on ice, and the reaction solution was stirred at room temperature for 1 hour. The reaction solution was filtered, the filtrate was concentrated under reduced pressure, and the residue was purified with silica gel chromatography (hexane/ethyl acetate=67:33) to yield the title compound (0.72 g, 53%) as a colorless solid.

¹H-NMR (500 MHz, CDCl₃) δ ppm: 3.78 (3H, s), 3.80 (3H, s), 5.23 (2H, s), 6.42-6.43 (2H, m), 6.99-7.04 (1H, m), 7.13 (1H, d, J=5.9 Hz), 7.22 (1H, d, J=9.3 Hz), 7.91-7.96 (1H, m), 8.48 (1H, d, J=6.4 Hz), 8.78 (1H, s).

(1c) (1S*,2R*)-2-(1-Methyl-1H-pyrazol-5-yl)cyclopentanol

To a solution of 1-methylpyrazole (13.4 g, 163 mmol) in THF (tetrahydrofuran; 1.0 L), n-butyl lithium (1.63 M solution in hexane; 100 mL, 163 mmol) was added dropwise at −78° C. for 40 minutes. To the reaction solution, cyclopentene oxide (15.1 g, 179 mmol) was added at −78° C., and the reaction solution was stirred at room temperature for 20 hours. To the reaction solution, a saturated aqueous solution of sodium hydrogencarbonate (100 mL) was added, followed by extraction with ethyl acetate (500 mL). The thus obtained organic layer was dried over anhydrous sodium sulfate. After concentration under reduced pressure, the residue was purified with silica gel chromatography (dichloromethane/methanol=97:3) to yield the title compound (5.77 g, 21%) as a colorless oil.

¹H-NMR (500 MHz, CDCl₃) δ ppm: 1.63-1.91 (4H, m), 2.05-2.12 (1H, m), 2.17-2.24 (1H, m), 3.03 (1H, q, J=8.3 Hz), 3.86 (3H, s), 4.24 (1H, q, J=6.4 Hz), 6.03 (1H, s), 7.39 (1H, s).

(1d) N-(2,4-Dimethoxybenzyl)-2,5-difluoro-4-{[(1S*,2R*)-2-(1-methyl-1H-pyrazol-5-yl)cyclopentyl]oxy}-N-(pyrimidin-4-yl)benzenesulfonamide To a solution of the N-(2,4-dimethoxybenzyl)-2,4,5-trifluoro-N-(pyrimidin-4-yl)benzenesulfonamide (0.76 g, 1.73 mmol) prepared in Example 1b and the (1S*,2R*)-2-(1-methyl-1H-pyrazol-5-yl)cyclopentanol (0.29 g, 1.73 mmol) prepared in Example 1c in DMF (dimethylformamide; 10 mL), sodium hydride (63%; 100 mg, 2.59 mmol) was added with cooling on ice, and the reaction solution was stirred at room temperature for 1 hour. Water (50 mL) was added to the reaction solution, followed by extraction with ethyl acetate (50 mL). The thus obtained organic layer was washed twice with water (100 mL) and dried over anhydrous sodium sulfate. After concentration under reduce pressure, the residue was purified with silica gel chromatography (hexane/ethyl acetate=1:1) to yield the title compound (0.89 g, 88%) as a colorless oil.

¹H-NMR (500 MHz, CDCl₃) δ ppm: 1.78-1.97 (4H, m), 2.20-2.33 (2H, m), 3.45-3.49 (1H, m), 3.77 (3H, s), 3.79 (3H, s), 3.86 (3H, s), 4.60-4.64 (1H, m), 5.23 (2H, s), 6.05 (1H, d, J=2.0 Hz), 6.40-6.42 (2H, m), 6.52 (1H, dd, J=5.9, 10.7 Hz), 7.18-7.20 (2H, m), 7.40 (1H, d, J=2.0 Hz), 7.76 (1H, dd, J=6.4, 10.3 Hz), 8.45 (1H, d, J=5.9 Hz), 8.78 (1H, s).

(1e) 2,5-Difluoro-4-{[(1S*,2R*)-2-(1-methyl-1H-pyrazol-5-yl)cyclopentyl]oxy}-N-(pyrimidin-4-yl)benzenesulfonamide To a solution of the N-(2,4-dimethoxybenzyl)-2,5-difluoro-4-{[(1S*,2R*)-2-(1-methyl-1H-pyrazol-5-yl)cyclopentyl]oxy}-N-pyrimidin-4-ylbenzenesulfonamide (0.54 g, 1.24 mmol) prepared in Example 1d and triethylsilane (1.98 mL, 12.4 mmol) in dichloromethane (20 mL), trifluoroacetic acid (0.96 mL, 12.4 mmol) was added at room temperature, and the reaction solution was stirred for 1 hour. The reaction solution was concentrated, and the residue was purified with silica gel chromatography (dichloromethane/methanol=95:5) to yield the title compound (0.54 g, 99%) as a colorless solid.

¹H-NMR (500 MHz, DMSO-d₆) δ ppm: 1.66-1.83 (4H, m), 2.19-2.27 (2H, m), 3.47-3.51 (1H, m), 3.76 (3H, s), 4.92-4.95 (1H, m), 6.17 (1H, s), 6.97 (1H, brs), 7.20-7.24 (1H, m), 7.30 (1H, s), 7.68-7.71 (1H, m), 8.25 (1H, brs), 8.57 (1H, s).

MS (ESI) m/z: 436 [M+H]⁺.

Example 2

5-Chloro-2-fluoro-4-{[(1S*,2R*)-2-(1-methyl-1H-pyrazol-5-yl)cyclopentyl]oxy}-N-(pyrimidin-4-yl)benzenesulfonamide

[Formula 24]

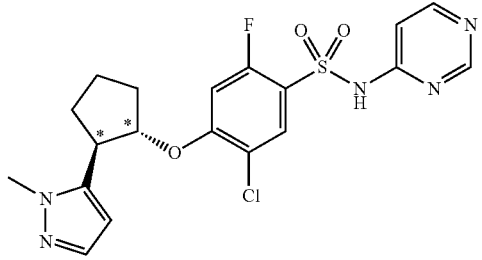

(2a) 5-Chloro-N-(2,4-dimethoxybenzyl)-2,4-difluoro-N-(pyrimidin-4-yl)benzenesulfonamide The reaction and aftertreatment were conducted in the same manner as in Example 1b by using the N-(2,4-dimethoxybenzyl)pyrimidine-4-amine (150 mg, 0.611 mmol) prepared in Example 1a, 5-chloro-2,4-difluorobenzenesulfonyl chloride (302 mg, 1.22 mmol), 1,4-diazabicyclo[2.2.2]octane (137 mg, 1.22 mmol) and acetonitrile (5.0 mL), to yield the title compound (71.7 mg, 26%) as a colorless oil.

¹H-NMR (500 MHz, CDCl₃) δ ppm: 3.78 (3H, s), 3.79 (3H, s), 5.23 (2H, s), 6.41-6.43 (2H, m), 6.98 (1H, d, J=9.3 Hz), 7.16 (1H, d, J=7.3 Hz), 7.22 (1H, d, J=8.8 Hz), 8.13 (1H, t, J=7.3 Hz), 8.49 (1H, d, J=5.9 Hz), 8.79 (1H, s).

(2b) 5-Chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (71.7 mg, 0.157 mmol) prepared in Example 2a, the (1S*,2R*)-2-(1-methyl-1H-pyrazol-5-yl)cyclopentanol (31.1 mg, 0.187 mmol) prepared in Example 1c, sodium hydride (63%; 7.1 mg, 0.186 mmol) and DMF (2.0 mL), to yield the title compound (79.1 mg, 84%) as a colorless oil.

¹H-NMR (500 MHz, CDCl₃) δ ppm: 1.73-1.98 (4H, m), 2.17-2.35 (2H, m), 3.48-3.52 (1H, m), 3.76 (3H, s), 3.78 (3H, s), 3.88 (3H, s), 4.60-4.63 (1H, m), 5.22 (1H, d, J=17.1 Hz), 5.26 (1H, d, J=17.1 Hz), 6.06 (1H, d, J=1.5 Hz), 6.39-6.41 (2H, m), 6.48 (1H, d, J=11.7 Hz), 7.18-7.21 (2H, m), 7.40 (1H, s), 8.02 (1H, d, J=7.3 Hz), 8.46 (1H, d, J=5.9 Hz), 8.79 (1H, s).

(2c) 5-Chloro-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (79.1 mg, 0.131 mmol) prepared in Example 2b, triethylsilane (0.05 mL), trifluoroacetic acid (1.0 mL) and dichloromethane (1.0 mL), to yield the title compound (30.0 mg, 51%) as a colorless solid.
¹H-NMR (500 MHz, CDCl₃) δ ppm: 1.79-1.96 (4H, m), 2.20-2.33 (2H, m), 3.48-3.52 (1H, m), 3.89 (3H, s), 4.60-4.63 (1H, m), 6.05 (1H, s), 6.54 (1H, d, J=11.7 Hz), 7.26-7.27 (1H, m), 7.39 (1H, s), 8.02 (1H, d, J=7.3 Hz), 8.39 (1H, J=4.9 Hz), 8.81 (1H, s).
MS (ESI) m/z: 452 [M+H]⁺.

Example 3

2,5-Difluoro-4-{[(1S*,2R*)-2-(1-methyl-1H-pyrazol-5-yl) cyclohexyl]oxy}-N-(pyrimidin-4-yl)benzenesulfonamide

[Formula 25]

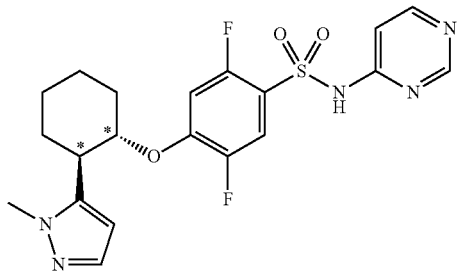

(3a) (1S*,2R*)-2-(1-Methyl-1H-pyrazol-5-yl)cyclohexanol

To a solution of 1-methylpyrazole (9.34 g, 114 mmol) and N,N,N',N'-tetramethylethylenediamine (17.1 mL, 114 mmol) in THF (300 mL), butyl lithium (1.63 M solution in hexane; 81.7 mL, 133 mmol) was added at −78° C. The reaction solution was stirred at −78° C. for 30 minutes. Then, cyclohexene oxide (13.9 mL, 137 mmol) was added thereto, and the mixture was stirred at room temperature for 15 hours. Water (1 L) was added to the reaction solution, followed by extraction with ethyl acetate (500 mL). The thus obtained organic layer was dried over anhydrous sodium sulfate. After concentration under reduced pressure, the residue was purified with silica gel chromatography (ethyl acetate) to yield the title compound (11.2 g, 55%) as a colorless solid.
¹H-NMR (400 MHz, CDCl₃) δ ppm: 1.30-1.48 (4H, m), 1.76-1.91 (4H, m), 2.09-2.15 (1H, m), 2.57-2.63 (1H, m), 3.59-3.65 (1H, m), 3.86 (3H, s), 6.08 (1H, d, J=2.0 Hz), 7.44 (1H, d, J=2.0 Hz).

(3b) N-(2,4-Dimethoxybenzyl)-2,5-difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (244 mg, 0.555 mmol) prepared in Example 1b, the (1S*,2R*)-2-(1-methyl-1H-pyrazol-5-yl)cyclohexanol (100 mg, 0.555 mmol) prepared in Example 3a, sodium hydride (63%; 31.7 mg, 0.793 mmol) and DMF (3 mL), to yield the title compound (268 mg, 80%) as a colorless oil.
¹H-NMR (500 MHz, CDCl₃) δ ppm: 1.39-1.68 (4H, m), 1.86-1.96 (2H, m), 2.04-2.07 (1H, m), 2.28 (1H, m), 2.98-3.03 (1H, m), 3.76 (3H, s), 3.77 (3H, s), 3.91 (3H, s), 4.08-4.14 (1H, m), 5.19 (1H, d, J=17.1 Hz), 5.23 (1H, d, J=16.6 Hz), 6.02 (1H, d, J=2.0 Hz), 6.39-6.40 (2H, m), 6.47 (1H, dd, J=6.4, 11.2 Hz), 7.17-7.19 (2H, m), 7.33 (1H, d, J=1.5 Hz), 7.67 (1H, dd, J=6.4, 9.8 Hz), 8.45 (1H, d, J=5.9 Hz), 8.78 (1H, s).

(3c) 2,5-Difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the N-(2,4-dimethoxybenzyl)-2,5-difluoro-4-{[(1S*,2R*)-2-(1-methyl-1H-pyrazol-5-yl)cyclohexyl]oxy}-N-(pyrimidin-4-yl)benzenesulfonamide (268 mg, 0.447 mmol) prepared in Example 3b, triethylsilane (0.20 mL), trifluoroacetic acid (2.0 mL) and dichloromethane (2.0 mL), to yield the title compound (130 mg, 65%) as a colorless solid.
¹H-NMR (500 MHz, CDCl₃) δ ppm: 1.38-1.68 (4H, m), 1.86-1.89 (1H, m), 1.93-1.95 (1H, m), 2.05-2.07 (1H, m), 2.28 (1H, m), 2.97-3.02 (1H, m), 3.90 (3H, s), 4.07-4.12 (1H, m), 6.02 (1H, d, J=2.0 Hz), 6.50 (1H, dd, J=6.4, 11.2 Hz), 7.24 (1H, d, J=6.4 Hz), 7.33 (1H, d, J=2.0 Hz), 7.66 (1H, dd, J=6.8, 10.3 Hz), 8.38 (1H, d, J=6.4 Hz), 8.80 (1H, s).
MS (ESI) m/z: 450 [M+H]⁺.

Example 4

2,6-Difluoro-4-{[(1S*,2R*)-2-(1-methyl-1H-pyrazol-5-yl) cyclopentyl]oxy}-N-(pyrimidin-4-yl)benzenesulfonamide

[Formula 26]

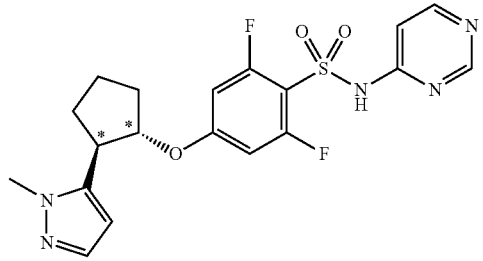

(4a) N-(2,4-Dimethoxybenzyl)-2,4,6-trifluoro-N-(pyrimidin-4-yl)benzenesulfonamide The reaction and aftertreatment were conducted in the same manner as in Example 1b by using the N-(2,4-dimethoxybenzyl)pyrimidin-4-amine (600 mg, 2.44 mmol) prepared in Example 1a, 2,4,6-trifluorobenzenesulfonyl chloride (1.50 g, 6.51 mmol), 1,4-diazabicyclo[2.2.2]octane (549 mg, 4.89 mmol) and acetonitrile (12 mL), to yield the title compound (192 mg, 18%) as a colorless amorphous solid.
¹H-NMR (500 MHz, CDCl₃) δ ppm: 3.78 (3H, s), 3.73 (3H, s), 5.26 (2H, s), 6.42-6.46 (2H, m), 6.78 (2H, t, J=8.3 Hz), 7.07 (1H, dd, J=1.5, 5.9 Hz), 7.24 (1H, d, J=8.8 Hz), 8.46 (1H, d, J=6.4 Hz), 8.78 (1H, s).

(4b) N-(2,4-Dimethoxybenzyl)-2,6-difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (192 mg, 0.44 mmol) prepared in Example 4a, the (1S*,2R*)-2-(1-methyl-1H-pyrazol-5-yl)cyclopentanol (76.3 mg, 0.46 mmol) prepared in Example 1c, sodium hydride (63%; 25.0 mg, 0.66 mmol) and DMF (2.0 mL), to yield the title compound (192 mg, 75%) as a colorless oil.

$^1$H-NMR (500 MHz, CDCl$_3$) δ ppm: 1.72-1.95 (4H, m), 2.17-2.32 (2H, m), 3.35-3.39 (1H, m), 3.77 (3H, s), 3.82 (6H, s), 4.639 (1H, m), 5.27 (2H, s), 6.04 (1H, d, J=2.0 Hz), 6.39-6.44 (4H, m), 7.16 (1H, d, J=7.3 Hz), 7.22 (1H, d, J=7.3 Hz), 7.41 (1H, d, J=2.0 Hz), 8.44 (1H, d, J=5.9 Hz), 8.78 (1H, s).

(4c) 2,6-Difluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2,6-difluoro-4-{[(1S*,2R*)-2-(1-methyl-1H-pyrazol-5-yl)cyclopentyl]oxy}-N-(pyrimidin-4-yl)benzenesulfonamide (192 mg, 0.33 mmol) prepared in Example 4b, triethylsilane (0.20 mL), trifluoroacetic acid (2.0 mL) and dichloromethane (2.0 mL), to yield the title compound (106 mg, 74%) as a colorless solid.

$^1$H-NMR (500 MHz, CDCl$_3$) δ ppm: 1.72-1.95 (4H, m), 2.17-2.31 (2H, m), 3.35-3.39 (1H, m), 3.82 (3H, s), 4.61-4.64 (1H, m), 6.04 (1H, d, J=2.0 Hz), 6.41 (2H, d, J=10.7 Hz), 7.40-7.42 (2H, m), 8.42 (1H, d, J=5.9 Hz), 8.87 (1H, s).
MS (ESI) m/z: 436 [M+H]$^+$.

Example 5

4-{[(1S*,2R*)-2-(1-Ethyl-1H-pyrazol-5-yl) cyclohexyl]oxy}-2,5-difluoro-N-(pyrimidin-4-yl)benzenesulfonamide

[Formula 27]

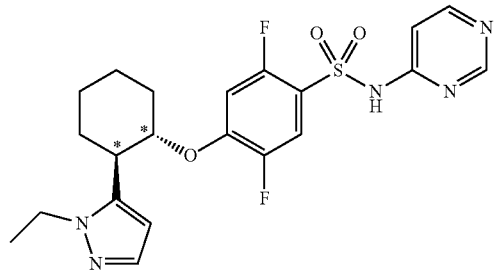

(5a) (1S*,2R*)-2-(1-Ethyl-1H-pyrazol-5-yl)cyclohexanol

The reaction and aftertreatment were conducted in the same manner as in Example 3a by using 1-ethylpyrazole (2.50 g, 26.0 mmol), butyl lithium (1.63 M solution in hexane; 18.1 mL, 29.5 mmol), cyclohexene oxide (2.97 g, 30.3 mmol), and THF (60 mL), to yield the title compound (2.86 g, 57%) as a colorless oil.

$^1$H-NMR (400 MHz, CDCl$_3$) δ ppm: 1.30-1.47 (4H, m), 1.43 (3H, t, J=7.4 Hz), 1.66 (1H, brs), 1.76-1.79 (1H, m), 1.87-1.90 (2H, m), 2.10-2.13 (1H, m), 2.56-2.62 (1H, m), 3.61-3.66 (1H, m), 4.10-4.26 (2H, m), 6.07 (1H, d, J=2.0 Hz), 7.47 (1H, d, J=1.6 Hz).

(5b) N-(2,4-Dimethoxybenzyl)-4-{[(1S*,2R*)-2-(1-ethyl-1H-pyrazol-5-yl)cyclohexyl]oxy}-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (270 mg, 0.615 mmol) prepared in Example 1b, the (1S*,2R*)-2-(1-ethyl-1H-pyrazol-5-yl)cyclohexanol (120 mg, 0.618 mmol) prepared in Example 5a, sodium hydride (63%; 50 mg, 1.31 mmol) and DMF (3 mL), to yield the title compound (220 mg, 58%) as a colorless oil.

$^1$H-NMR (500 MHz, CDCl$_3$) δ ppm: 1.39-1.66 (4H, m), 1.43 (3H, t, J=7.3 Hz), 1.85-1.88 (1H, m), 1.94-1.96 (1H, m), 2.03-2.06 (1H, m), 2.28 (1H, m), 2.97-3.03 (1H, m), 3.76 (3H, s), 3.77 (3H, s), 4.12-4.32 (3H, m), 5.19 (1H, d, J=16.6 Hz), 5.23 (1H, d, J=17.1 Hz), 6.00 (1H, d, J=2.0 Hz), 6.38-6.40 (2H, m), 6.47 (1H, dd, J=6.4, 11.2 Hz), 7.17-7.19 (2H, m), 7.36 (1H, d, J=1.5 Hz), 7.66 (1H, dd, J=6.8, 10.3 Hz), 8.45 (1H, d, J=5.9 Hz), 8.78 (1H, s).

(5c) 4-{[(1S*,2R*)-2-(1-Ethyl-1H-pyrazol-5-yl) cyclohexyl]oxy}-2,5-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-2-(1-ethyl-1H-pyrazol-5-yl)cyclohexyl]oxy}-2,5-difluoro-N-(pyrimidin-4-yl)benzenesulfonamide (220 mg, 0.359 mmol) prepared in Example 5b, triethylsilane (0.30 mL), trifluoroacetic acid (3.0 mL) and dichloromethane (3.0 mL), to yield the title compound (160 mg, 96%) as a colorless solid.

$^1$H-NMR (500 MHz, CD$_3$OD) δ ppm: 1.37 (3H, t, J=7.3 Hz), 1.43-1.73 (4H, m), 1.81-1.83 (1H, m), 1.89-1.91 (1H, m), 1.96-1.99 (1H, m), 2.23-2.25 (1H, m), 3.06-3.11 (1H, m), 4.11-4.18 (1H, m), 4.26-4.33 (1H, m), 4.46-4.50 (1H, m), 6.14 (1H, d, J=2.0 Hz), 6.97 (1H, dd, J=6.8, 11.7 Hz), 7.01 (1H, d, J=7.3 Hz), 7.27 (1H, d, J=2.0 Hz), 7.64 (1H, dd, J=6.4, 10.3 Hz), 8.26 (1H, d, J=6.4 Hz), 8.54 (1H, s).
MS (ESI) m/z: 464 [M+H]$^+$.

Example 6

2-Fluoro-4-{[(1S*,2R*)-2-(1-methyl-1H-pyrazol-5-yl)cyclopentyl]oxy}-N-(pyrimidin-4-yl)benzenesulfonamide

[Formula 28]

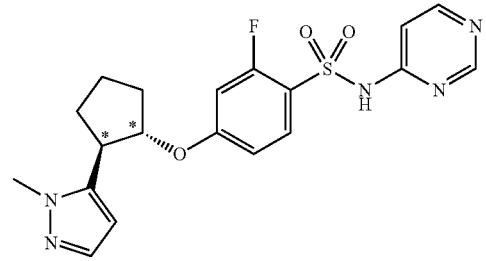

(6a) N-(2,4-Dimethoxybenzyl)-2,4-difluoro-N-(pyrimidin-4-yl)benzenesulfonamide The reaction and aftertreatment were conducted in the same manner as in Example 1b by using the N-(2,4-dimethoxybenzyl)pyrimidine-4-amine (0.40 g, 1.63 mmol) prepared in Example 1a, 2,4-difluorobenzenesulfonyl chloride (0.69 g, 3.26 mmol), 1,4-diazabicyclo[2.2.2]octane (0.37 g, 3.26 mmol) and acetonitrile (11 mL), to yield the title compound (403.8 mg, 59%) as a colorless solid.

$^1$H-NMR (400 MHz, CDCl$_3$) δ ppm: 3.77 (3H, s), 3.80 (3H, s), 5.26 (2H, s), 6.41-6.44 (2H, m), 6.87-6.92 (1H, m), 7.01-7.06 (1H, m), 7.16 (1H, dd, J=1.6, 5.9 Hz), 7.22 (1H, d, J=8.2 Hz), 8.12 (1H, dt, J=5.9, 8.6 Hz), 8.45 (1H, d, J=5.9 Hz), 8.75 (1H, d, J=1.2 Hz).

(6b) N-(2,4-Dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the N-(2,4-dimethoxybenzyl)-2,4-difluoro-N-(pyrimidin-4-yl)benzenesulfonamide (0.40 g, 0.95 mmol) prepared in Example 6a, the (1S*,2R*)-2-(1-methyl-1H-pyrazol-5-yl)cyclopentanol (0.16 g, 0.95 mmol) prepared in Example 1c, sodium hydride (63%; 0.040 g, 1.14 mmol) and DMF (5.0 mL), to yield the title compound (268.5 mg, 50%) as a colorless oil.

$^1$H-NMR (500 MHz, CDCl$_3$) δ ppm: 1.72-1.95 (4H, m), 2.17-2.31 (2H, m), 3.35-3.39 (1H, m), 3.76 (3H, s), 3.80 (3H, s), 3.82 (3H, s), 4.66-4.69 (1H, m), 5.26 (2H, s), 6.05 (1H, d, J=2.0 Hz), 6.40-6.43 (2H, m), 6.53 (1H, dd, J=2.4, 11.7 Hz), 6.67 (1H, dd, J=2.4, 9.3 Hz), 7.20 (1H, d, J=8.3 Hz), 7.23 (1H, dd, J=1.0, 5.9 Hz), 7.40 (1H, d, J=2.0 Hz), 7.94 (1H, t, J=8.8 Hz), 8.42 (1H, d, J=5.9 Hz), 8.75 (1H, d, J=1.0 Hz).

(6c) 2-Fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (0.27 g, 0.47 mmol) prepared in Example 6b, triethylsilane (0.38 mL, 2.36 mmol), trifluoroacetic acid (0.47 g, 0.44 mmol) and dichloromethane (5.0 mL), to yield the title compound (0.21 g, 22%) as a colorless solid.

$^1$H-NMR (400 MHz, CD$_3$OD) δ ppm: 1.76-1.95 (4H, m), 2.26-2.33 (2H, m), 3.45-3.49 (1H, m), 3.80 (3H, s), 4.86-4.91 (1H, m), 6.24 (1H, d, J=2.4 Hz), 6.77-6.86 (2H, m), 7.15 (1H, d, J=7.4 Hz), 7.43 (1H, d, J=2.0 Hz), 7.95 (1H, t, J=8.6 Hz), 8.40 (1H, d, J=5.9 Hz), 8.68 (1H, s).

MS (ESI) m/z: 418 [M+H]$^+$.

Example 7

2,5-Difluoro-4-{[(1S,2R)-2-(1-methyl-1H-pyrazol-5-yl)cyclopentyl]oxy}-N-(pyrimidin-4-yl)benzenesulfonamide

[Formula 29]

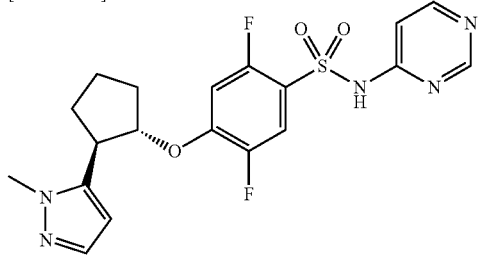

(7a) N-(2,4-Dimethoxybenzyl)-2,5-difluoro-4-{[(1S,2R)-2-(1-methyl-1H-pyrazol-5-yl)cyclopentyl]oxy}-N-(pyrimidin-4-yl)benzenesulfonamide The N-(2,4-dimethoxybenzyl)-2,5-difluoro-4-{[(1S*,2R*)-2-(1-methyl-1H-pyrazol-5-yl)cyclopentyl]oxy}-N-(pyrimidin-4-yl)benzenesulfonamide prepared in Example 1d was optically resolved with CHIRALPAK AD (Daicel Corp.; hexane/isopropanol=4:1) to yield the title compound as a colorless oil.

(7b) 2,5-Difluoro-4-{[(1S,2R)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the -(2,4-dimethoxybenzyl)-2,5-difluoro-4-{[(1S,2R)-2-(1-methyl-1H-pyrazol-5-yl)cyclopentyl]oxy}-N-(pyrimidin-4-yl)benzenesulfonamide (411 mg, 0.70 mmol) prepared in Example 7a, triethylsilane (0.20 mL), trifluoroacetic acid (2.0 mL) and dichloromethane (2.0 mL), to yield the title compound (241 mg, 79%) as a colorless solid.

$[α]_D^{25}$=58.9 (c 1.02, DMSO).

Example 8

4-{[(1S*,2R*)-2-(1-Ethyl-1H-pyrazol-5-yl)cyclopentyl]oxy}-2,3-difluoro-N-(pyrimidin-4-yl)benzenesulfonamide

[Formula 30]

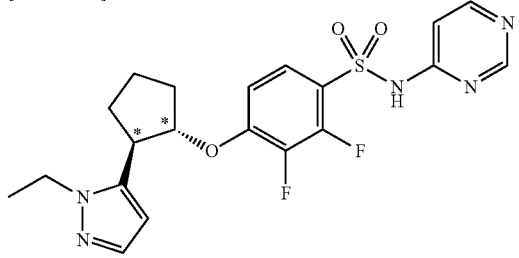

(8a) N-(2,4-Dimethoxybenzyl)-2,3,4-trifluoro-N-(pyrimidin-4-yl)benzenesulfonamide The reaction and aftertreatment were conducted in the same manner as in Example 1b by using the N-(2,4-dimethoxybenzyl)pyrimidin-4-amine (400 mg, 1.63 mmol) prepared in Example 1a, 2,3,4-trifluorobenzenesulfonyl chloride (752 mg, 3.26 mmol), 1,4-diazabicyclo[2.2.2]octane (366 mg, 3.26 mmol), and acetonitrile (8.0 mL), to yield the title compound (221 mg, 31%) as a colorless amorphous solid.

¹H-NMR (500 MHz, CDCl₃) δ ppm: 3.78 (3H, s), 3.80 (3H, s), 5.24 (2H, s), 6.42-6.44 (2H, m), 7.11-7.16 (2H, m), 7.22 (1H, d, J=7.8 Hz), 7.84-7.89 (1H, m), 8.48 (1H, d, J=5.9 Hz), 8.76 (1H, s).

(8b) (1S*,2R*)-2-(1-Ethyl-1H-pyrazol-5-yl)cyclopentanol

The reaction and aftertreatment were conducted in the same manner as in Example 3a by using 1-ethylpyrazole (97%, 2.53 g, 25.5 mmol), N,N,N',N'-tetramethylethylenediamine (3.83 mL, 25.5 mmol), butyl lithium (1.63 M solution in hexane; 18.3 mL, 29.8 mmol), cyclopentene oxide (2.66 g, 31.6 mmol) and THF (60 mL), to yield the title compound (750 mg, 16%) as a colorless oil.

¹H-NMR (500 MHz, CDCl₃) δ ppm: 1.42 (3H, t, J=7.3 Hz), 1.63-1.91 (4H, m), 2.04-2.23 (2H, m), 3.02 (1H, q, J=8.3 Hz), 4.01-4.23 (3H, m), 6.01 (1H, d, J=1.5 Hz), 7.41 (1H, s).

(8c) N-(2,4-Dimethoxybenzyl)-4-{[(1S*,2R*)-2-(1-ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1d by using the N-(2,4-dimethoxybenzyl)-2,3,4-trifluoro-N-(pyrimidin-4-yl)benzenesulfonamide (76.8 mg, 0.175 mmol) prepared in Example 8a, the (1S*,2R*)-2-(1-ethyl-1H-pyrazol-5-yl)cyclopentanol (30.0 mg, 0.166 mmol) prepared in Example 8b, sodium hydride (63%; 9.5 mg, 0.249 mmol) and DMF (1.0 mL), to yield the title compound (80.0 mg, 80%) as a colorless oil.

¹H-NMR (500 MHz, CDCl₃) δ ppm: 1.39 (3H, t, J=7.3 Hz), 1.74-1.83 (2H, m), 1.92-1.98 (2H, m), 2.22-2.35 (2H, m), 3.46 (1H, dt, J=4.9, 8.8 Hz), 3.76 (3H, s), 3.79 (3H, s), 4.12-4.21 (2H, m), 4.74-4.76 (1H, m), 5.23 (1H, d, J=16.6 Hz), 5.28 (1H, d, J=16.6. Hz), 6.05 (1H, d, J=1.5 Hz), 6.39-6.42 (2H, m), 6.64 (1H, t, J=8.3 Hz), 7.19-7.20 (2H, m), 7.45 (1H, d, J=1.5 Hz), 7.70 (1H, dt, J=1.5, 7.3 Hz), 8.44 (1H, d, J=5.9 Hz), 8.76 (1H, s).

(8d) 4-{[(1S*,2R*)-2-(1-Ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-2-(1-ethyl-1H-pyrazol-5-yl)cyclopentyl]oxy}-2,3-difluoro-N-(pyrimidin-4-yl)benzenesulfonamide (80.0 mg, 0.133 mmol) prepared in Example 8c, triethylsilane (0.10 mL), trifluoroacetic acid (1.0 mL) and dichloromethane (1.0 mL), to yield the title compound (30.0 mg, 50%) as a colorless solid.

¹H-NMR (500 MHz, CDCl₃) δ ppm: 1.38 (3H, t, J=7.3 Hz), 1.75-1.83 (1H, m), 1.93-1.96 (3H, m), 2.22-2.34 (2H, m), 3.46 (1H, dt, J=4.6, 8.3 Hz), 4.10-4.22 (2H, m), 4.73-4.76 (1H, m), 6.05 (1H, d, J=1.5 Hz), 6.65 (1H, t, J=8.8 Hz), 7.20 (1H, d, J=6.4 Hz), 7.44 (1H, d, J=1.5 Hz), 7.68-7.72 (1H, m), 8.35 (1H, d, J=6.4 Hz), 8.73 (1H, s).

MS (ESI) m/z: 450 [M+H]⁺.

Example 9

2,5-Difluoro-4-{[(1S*,2R*)-2-(1-methyl-1H-pyrazol-5-yl)cycloheptyl]oxy}-N-(pyrimidin-4-yl)benzenesulfonamide

[Formula 31]

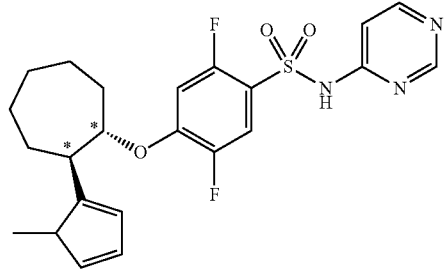

(9a) (1S*,2R*)-2-(1-Methyl-1H-pyrazol-5-yl)cycloheptanol

The reaction and aftertreatment were conducted in the same manner as in Example 3a by using 1-methylpyrazole (3.66 g, 44.6 mmol), N,N,N',N'-tetramethylethylenediamine (6.68 mL, 44.6 mmol), n-butyl lithium (1.63 M solution in hexane; 32 mL, 52.2 mmol), 1,2-epoxycycloheptane (5.0 g, 44.6 mmol), and THF (60 mL), to yield the title compound (1.13 g, 13%) as a colorless oil.

¹H-NMR (500 MHz, CDCl₃) δ ppm: 1.56-1.89 (9H, m), 1.98-2.05 (1H, m), 2.76-2.82 (1H, m), 3.80-3.86 (1H, m), 3.84 (3H, s), 6.06 (1H, d, J=2.0 Hz), 7.41 (1H, d, J=2.4 Hz).

(9b) N-(2,4-Dimethoxybenzyl)-2,5-difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (100 mg, 0.228 mmol) prepared in Example 1b, the (1S*,2R*)-2-(1-methyl-1H-pyrazol-5-yl)cycloheptanol (30 mg, 0.154 mmol) prepared in Example 9a, sodium hydride (63%; 40 mg, 1.05 mmol) and DMF (2 mL), to yield the title compound (50 mg, 53%) as a colorless oil.

¹H-NMR (500 MHz, CDCl₃) δ ppm: 1.57-1.99 (10H, m), 3.23 (1H, dt, J=3.4, 9.8 Hz), 3.76 (3H, s), 3.78 (3H, s), 3.89 (3H, s), 4.34-4.38 (1H, m), 5.19 (1H, d, J=16.6 Hz), 5.23 (1H, d, J=17.1 Hz), 6.00 (1H, d, J=2.0 Hz), 6.39-6.42 (3H, m), 7.17-7.19 (2H, m), 7.33 (1H, d, J=2.0 Hz), 7.67 (1H, dd, J=6.4, 9.8 Hz), 8.45 (1H, d, J=5.9 Hz), 8.78 (1H, s).

(9c) 2,5-Difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1e by using the N-(2,4-dimethoxybenzyl)-2,5-difluoro-4-{[(1S*,2R*)-2-(1-methyl-1H-pyrazol-5-yl)cycloheptyl]oxy}-N-(pyrimidin-4-yl)benzenesulfonamide (50 mg, 0.0815 mmol) prepared in Example 9b, triethylsilane (0.10 mL), trifluoroacetic acid (1.0 mL) and dichloromethane (1.0 mL), to yield the title compound (32 mg, 85%) as a colorless solid.

$^1$H-NMR (500 MHz, CDCl$_3$) δ ppm: 1.61-1.98 (10H, m), 3.22 (1H, dt, J=2.9, 9.3 Hz), 3.89 (3H, s), 4.32-4.36 (1H, m), 6.00 (1H, d, J=2.0 Hz), 6.45 (1H, dd, J=6.4, 11.2 Hz), 7.21 (1H, brs), 7.32 (1H, d, J=2.0 Hz), 7.66 (1H, dd, J=6.8, 9.8 Hz), 8.40 (1H, d, J=6.4 Hz), 8.78 (1H, s).

MS (ESI) m/z: 464 [M+H]$^+$.

Example 10

2-Fluoro-5-methyl-4-{[(1S*,2R*)-2-(1-methyl-1H-pyrazol-5-yl)cyclopentyl]oxy}-N-(pyrimidin-4-yl)benzenesulfonamide

[Formula 32]

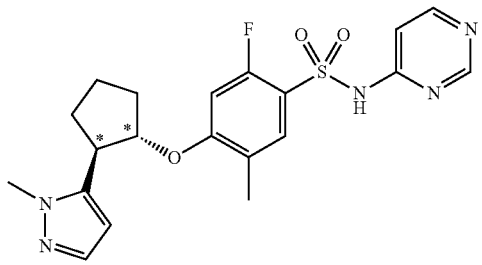

(10a) N-(2,4-Dimethoxybenzyl)-2,4-difluoro-5-methyl-N-(pyrimidin-4-yl)benzenesulfonamide The reaction and aftertreatment were conducted in the same manner as in Example 1b by using the N-(2,4-dimethoxybenzyl)pyrimidin-4-amine (1.0 g, 4.08 mmol) prepared in Example 1a, 2,4-difluoro-5-methylbenzenesulfonyl chloride (WO2010/079443; 1.85 g, 8.15 mmol), 1,4-diazabicyclo[2.2.2]octane (0.91 g, 8.15 mmol) and THF (20 mL), to yield the title compound (1.41 g, 79%) as a colorless amorphous solid.

$^1$H-NMR (500 MHz, CDCl$_3$) δ ppm: 2.31 (3H, s), 3.77 (3H, s), 3.79 (3H, s), 5.25 (2H, s), 6.40-6.42 (2H, m), 6.83 (1H, t, J=9.3 Hz), 7.20-7.23 (2H, m), 7.89 (1H, t, J=7.8 Hz), 8.45 (1H, d, J=5.9 Hz), 8.77 (1H, s).

(10b) N-(2,4-Dimethoxybenzyl)-2-fluoro-5-methyl-4-{[(1S*,2R)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (0.30 g, 0.69 mmol) prepared in Example 10a, the (1S*,2R*)-2-(1-methyl-1H-pyrazol-5-yl)cyclopentanol (0.12 g, 0.72 mmol) prepared in Example 1c, sodium hydride (63%; 0.040 g, 1.05 mmol) and DMF (10 mL), to yield the title compound (0.20 g, 50%) as a colorless oil.

$^1$H-NMR (500 MHz, CDCl$_3$) δ ppm: 1.74-1.95 (4H, m), 2.16-2.34 (2H, m), 2.20 (3H, s), 3.41 (1H, dt, J=4.9, 8.3 Hz), 3.76 (3H, s), 3.80 (3H, s), 3.84 (3H, s), 4.639 (1H, m), 5.26 (2H, s), 6.04 (1H, d, J=2.0 Hz), 6.37-6.42 (3H, m), 7.20 (1H, d, J=8.3 Hz), 7.26-7.28 (1H, m), 7.40 (1H, d, J=1.5 Hz), 7.76 (1H, d, J=7.8 Hz), 8.42 (1H, d, J=5.9 Hz), 8.76 (1H, s).

(10c) 2-Fluoro-5-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2-fluoro-5-methyl-4-{[(1S*,2R*)-2-(1-methyl-1H-pyrazol-5-yl)cyclopentyl]oxy}-N-(pyrimidin-4-yl)benzenesulfonamide (0.20 g, 0.34 mmol) prepared in Example 10b, triethylsilane (0.10 mL), trifluoroacetic acid (0.50 mL) and dichloromethane (4.0 mL), to yield the title compound (0.16 g, 98%) as a colorless amorphous solid.

$^1$H-NMR (500 MHz, CDCl$_3$) δ ppm: 1.73-1.93 (4H, m), 2.18-2.34 (2H, m), 2.21 (3H, s), 3.41 (1H, dt, J=4.4, 7.8 Hz), 3.84 (3H, s), 4.639 (1H, m), 6.04 (1H, d, J=1.5 Hz), 6.44 (1H, d, J=11.7 Hz), 7.24-7.25 (1H, m), 7.39 (1H, d, J=2.0 Hz), 7.75 (1H, d, J=7.8 Hz), 8.41 (1H, d, J=5.9 Hz), 8.86 (1H, brs).

MS (ESI) m/z: 432 [M+H]$^+$.

Example 11

2,6-Difluoro-4-{[(1S*,2R*)-2-(1-methyl-1H-pyrazol-5-yl)cyclohexyl]oxy}-N-(pyrimidin-4-yl)benzenesulfonamide

[Formula 33]

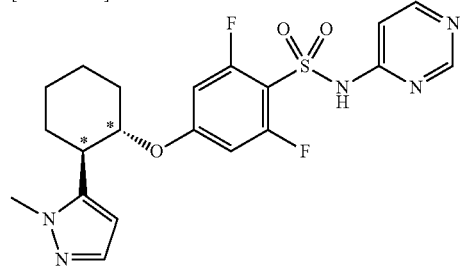

(11a) N-(2,4-Dimethoxybenzyl)-2,6-difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (0.19 g, 0.43 mmol) prepared in Example 4a, the (1S*,2R*)-2-(1-methyl-1H-pyrazol-5-yl)cyclohexanol (0.080 g, 0.45 mmol) prepared in Example 3a, sodium hydride (63%; 0.030 g, 0.79 mmol) and DMF (5 mL), to yield the title compound (0.12 g, 48%) as a colorless amorphous solid.

$^1$H-NMR (500 MHz, CDCl$_3$) δ ppm: 1.38-1.67 (4H, m), 1.86-1.88 (1H, m), 1.94-1.95 (1H, m), 2.03-2.06 (1H, m), 2.22-2.24 (1H, m), 2.90-2.95 (1H, m), 3.77 (3H, s), 3.81 (3H, s), 3.86 (3H, s), 4.10-4.15 (1H, m), 5.24 (2H, s), 5.99 (1H, d, J=2.0 Hz), 6.29 (2H, d, J=10.7 Hz), 6.40-6.44 (2H, m), 7.14 (1H, dd, J=1.0, 5.9 Hz), 7.21 (1H, d, J=8.3 Hz), 7.34 (1H, d, J=2.0 Hz), 8.44 (1H, d, J=5.9 Hz), 8.78 (1H, s).

(11b) 2,6-Difluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the N-(2,4-dimethoxybenzyl)-2,6-difluoro-4-{[(1S*,2R*)-2-(1-methyl-1H-pyrazol-5-yl)cyclohexyl]oxy}-N-(pyrimidin-4-yl)benzenesulfonamide (0.12 g, 0.21 mmol) prepared in Example 11a, triethylsilane (0.10 mL), trifluoroacetic acid (0.50 mL) and dichloromethane (2.0 mL), to yield the title compound (0.030 g, 30%) as a colorless solid.

$^{1}$H-NMR (400 MHz, CDCl$_3$) δ ppm: 1.38-1.65 (4H, m), 1.85-1.88 (1H, m), 1.93-1.95 (1H, m), 2.03-2.08 (1H, m), 2.22-2.24 (1H, m), 2.89-2.96 (1H, m), 3.86 (3H, s), 4.09-4.15 (1H, m), 6.00 (1H, d, J=2.0 Hz), 6.32 (2H, d, J=10.6 Hz), 7.34 (1H, d, J=2.0 Hz), 7.41 (1H, d, J=6.7 Hz), 8.41 (1H, d, J=6.3 Hz), 8.80 (1H, s).

MS (ESI) m/z: 450 [M+H]$^+$.

Example 12

4-{[(1S*,2R*)-5,5-Difluoro-2-(1-methyl-1H-pyrazol-5-yl)cyclohexyl]oxy}-2,5-difluoro-N-(pyrimidin-4-yl)benzenesulfonamide

[Formula 34]

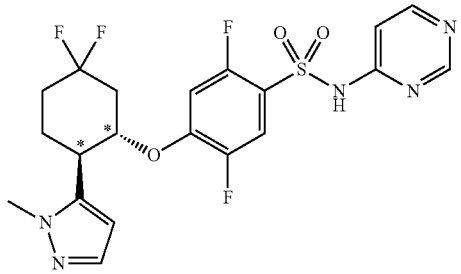

(12a) 5-(4,4-Difluorocyclohex-1-en-1-yl)-1-methyl-1H-pyrazole

A solution of 5-iodo-1-methyl-1H-pyrazole (1.90 g, 9.14 mmol), 2-(4,4-difluorocyclohex-1-en-1-yl)-4,4,5,5-tetramethyl-1,3,2-dioxaborolane (1.00 g, 4.10 mmol), tetrakis(triphenylphosphine)palladium(0) (240 mg, 0.208 mmol), and cesium carbonate (2.70 g, 8.29 mmol) in 1,4-dioxane (10 mL) and water (5.0 mL) was stirred at 90° C. for 4 hours. After allowing to cool, the reaction solution was subjected to extraction with ethyl acetate (50 mL), and the organic layer was dried over anhydrous sodium sulfate. The organic layer was concentrated under reduced pressure, and the residue was purified with column chromatography (hexane/ethyl acetate=9:1) to yield the title compound (767 mg, 94%) as a colorless oil.

$^{1}$H-NMR (500 MHz, CDCl$_3$) δ ppm: 2.13-2.22 (2H, m), 2.56-2.60 (2H, m), 2.73 (2H, t, J=14.2 Hz), 3.86 (3H, s), 5.73 (1H, brs), 6.14 (1H, d, J=2.0 Hz), 7.42 (1H, d, J=2.0 Hz).

(12b) (1S*,2R*)-5,5-Difluoro-2-(1-methyl-1H-pyrazol-5-yl)cyclohexanol

To a solution of the 5-(4,4-difluorocyclohex-1-en-1-yl)-1-methyl-1H-pyrazole (767 mg, 3.87 mmol) prepared in Example 12a in THF (4.0 mL), a borane-THF complex (0.95 M solution in THF, 12.2 mL, 11.6 mmol) was added with cooling on ice, and the reaction solution was stirred with cooling on ice for 90 minutes. Water (8.0 mL) and subsequently sodium perborate tetrahydrate (1.20 g, 7.80 mmol) were added to the reaction solution, and the mixture was stirred for 5 hours. Sodium thiosulfate (2.0 g) was added to the reaction solution, followed by extraction with ethyl acetate (50 mL). The thus obtained organic layer was dried over anhydrous sodium sulfate. After concentration under reduced pressure, the residue was purified with column chromatography (dichloromethane/methanol=96:4) to yield the title compound (148 mg, 18%) as a colorless oil.

$^{1}$H-NMR (500 MHz, CDCl$_3$) δ ppm: 1.68-1.95 (4H, m), 2.16-2.21 (1H, m), 2.51-2.57 (1H, m), 2.61-2.66 (1H, m), 3.76-3.83 (1H, m), 3.80 (3H, s), 3.89 (1H, brs), 6.02 (1H, d, J=2.0 Hz), 7.26 (1H, d, J=1.5 Hz).

(12c) 4-{[(1S*,2R*)-5,5-Difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (160 mg, 0.364 mmol) prepared in Example 1b, the (1S*,2R*)-5,5-difluoro-2-(1-methyl-1H-pyrazol-5-yl)cyclohexanol (76 mg, 0.351 mmol) prepared in Example 12b, sodium hydride (63%; 40 mg, 1.05 mmol) and DMF (2.0 mL), to yield the title compound (212 mg, 92%) as a colorless individual.

$^{1}$H-NMR (500 MHz, CDCl$_3$) δ ppm: 1.92-2.12 (4H, m), 2.29-2.33 (1H, m), 2.71-2.77 (1H, m), 3.07-3.12 (1H, m), 3.77 (3H, s), 3.78 (3H, s), 3.92 (3H, s), 4.32 (1H, dt, J=4.9, 10.7 Hz), 5.19 (1H, d, J=17.1 Hz), 5.23 (1H, d, J=17.1 Hz), 6.07 (1H, d, J=2.0 Hz), 6.39-6.44 (3H, m), 7.15-7.19 (2H, m), 7.36 (1H, d, J=2.0 Hz), 7.71 (1H, dd, J=6.4, 9.8 Hz), 8.46 (1H, d, J=5.9 Hz), 8.78 (1H, s).

(12d) 4-{[(1S*,2R*)-5,5-Difluoro-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1e by using the 4-{[(1S*,2R*)-5,5-difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (212 mg, 0.334 mmol) prepared in Example 12c, triethylsilane (0.30 mL), trifluoroacetic acid (3.0 mL) and dichloromethane (3.0 mL), to yield the title compound (153 mg, 95%) as a colorless solid.

$^{1}$H-NMR (500 MHz, DMSO-d$_6$) δ ppm: 1.36-1.77 (1H, m), 1.96-2.28 (4H, m), 2.64-2.71 (1H, m), 3.35-3.40 (1H, m), 3.79 (3H, s), 4.71 (1H, dt, J=4.4, 10.7 Hz), 6.19 (1H, d, J=1.5 Hz), 6.94 (1H, brs), 7.12-7.16 (1H, m), 7.18 (1H, d, J=2.0 Hz), 7.61-7.64 (1H, m), 8.24 (1H, brs), 8.56 (1H, s).

MS (ESI) m/z: 486 [M+H]$^+$.

Example 13

5-Chloro-2-fluoro-4-{[(1S*,2R*)-2-(1-methyl-1H-pyrazol-5-yl)cyclohexyl]oxy}-N-(pyrimidin-4-yl)benzenesulfonamide

[Formula 35]

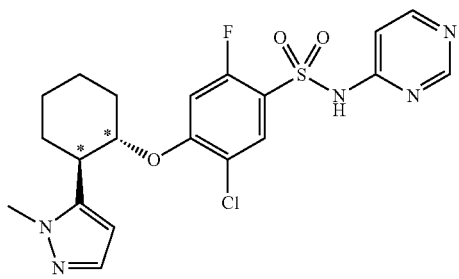

(13a) 5-Chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (0.234 g, 0.513 mmol) prepared in Example 2a, the (1S*,2R*)-2-(1-methyl-1H-pyrazol-5-yl)cyclohexanol (0.116 g, 0.644 mmol) prepared in Example 3a, sodium hydride (63%; 0.023 g, 0.600 mmol) and DMF (2 mL), to yield the title compound (0.273 g, 86%) as a colorless solid.

$^1$H-NMR (400 MHz, CDCl$_3$) δ ppm: 1.40-1.68 (4H, m), 1.85-1.97 (2H, m), 2.04-2.10 (1H, m), 2.18-2.23 (1H, m), 3.02-3.09 (1H, m), 3.76 (3H, s), 3.76 (3H, s), 3.93 (3H, s), 4.09-4.17 (1H, m), 5.21 (2H, s), 6.03 (1H, d, J=2.0 Hz), 6.38-6.45 (3H, m), 7.17-7.22 (2H, m), 7.35 (1H, d, J=2.0 Hz), 7.92 (1H, d, J=7.4 Hz), 8.46 (1H, d, J=5.9 Hz), 8.79 (1H, d, J=1.2 Hz).

(13b) 5-Chloro-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide (0.27 g, 0.438 mmol) prepared in Example 13a, triethylsilane (0.168 mL, 1.05 mmol), trifluoroacetic acid (3.4 mL) and dichloromethane (3.4 mL), to yield the title compound (0.148 g, 72%) as a colorless solid.

$^1$H-NMR (400 MHz, CDCl$_3$) δ ppm: 1.36-1.70 (4H, m), 1.85-1.96 (2H, m), 2.03-2.11 (1H, m), 2.18-2.23 (1H, m), 3.01-3.09 (1H, m), 3.93 (3H, s), 4.09-4.17 (1H, m), 6.03 (1H, d, J=2.0 Hz), 6.47 (1H, d, J=11.7 Hz), 7.23-7.27 (1H, m), 7.34 (1H, d, J=2.0 Hz), 7.94 (1H, d, J=7.8 Hz), 8.39 (1H, d, J=6.3 Hz), 8.81 (1H, s).

MS (ESI) m/z: 466 [M+H]$^+$.

Example 14

4-{[(1S*,2R*)-2-(1-Ethyl-1H-pyrazol-5-yl)cyclopentyl]oxy}-2,6-difluoro-N-(pyrimidin-4-yl)benzenesulfonamide

[Formula 36]

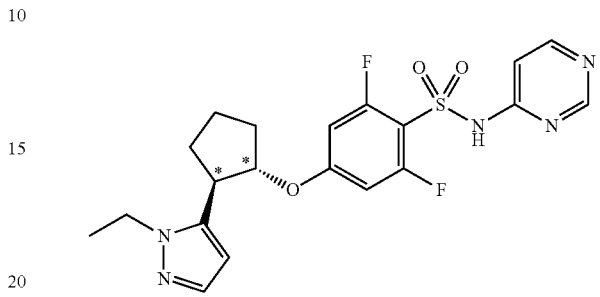

(14a) N-(2,4-Dimethoxybenzyl)-4-{[(1S*,2R*)-2-(1-ethyl-1H-pyrazol-5-yl)cyclopentyl]oxy}-2,6-difluoro-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (311 mg, 0.703 mmol) prepared in Example 4a, the (1S*,2R*)-2-(1-ethyl-1H-pyrazol-5-yl)cyclopentanol (127 mg, 0.703 mmol) prepared in Example 8b, sodium hydride (63%; 35.1 mg, 0.921 mmol) and DMF (5.0 mL), to yield the title compound (231 mg, 55%) as a colorless oil.

$^1$H-NMR (500 MHz, CDCl$_3$) δ ppm: 1.38 (3H, t, J=7.3 Hz), 1.73-1.95 (4H, m), 2.18-2.31 (2H, m), 3.36 (1H, dt, J=4.9, 8.3 Hz), 3.77 (3H, s), 3.82 (3H, s), 4.09-4.15 (2H, m), 4.639 (1H, m), 5.26 (2H, s), 6.03 (1H, d, J=2.0 Hz), 6.37-6.44 (4H, m), 7.16 (1H, dd, J=1.0, 5.9 Hz), 7.22 (1H, d, J=8.3 Hz), 7.44 (1H, d, J=2.0 Hz), 8.44 (1H, d, J=5.9 Hz), 8.78 (1H, s).

(14b) 4-{[(1S*,2R*)-2-(1-Ethyl-1H-pyrazol-5-yl)cyclopentyl]oxy}-2,6-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-2-(1-ethyl-1H-pyrazol-5-yl)cyclopentyl]oxy}-2,6-difluoro-N-(pyrimidin-4-yl)benzenesulfonamide (231 mg, 0.385 mmol) prepared in Example 14a, triethylsilane (0.20 mL), trifluoroacetic acid (2.0 mL) and dichloromethane (2.0 mL), to yield the title compound (151 mg, 87%) as a colorless amorphous solid.

$^1$H-NMR (500 MHz, CDCl$_3$) δ ppm: 1.38 (3H, t, J=7.3 Hz), 1.71-1.77 (1H, m), 1.84-1.95 (3H, m), 2.17-2.32 (2H, m), 3.37 (1H, dt, J=4.9, 8.3 Hz), 4.09-4.18 (2H, m), 4.61-4.64 (1H, m), 6.02 (1H, d, J=2.0 Hz), 6.41 (2H, d, J=10.7 Hz), 7.40 (1H, d, J=5.9 Hz), 7.43 (1H, d, J=2.0 Hz), 8.42 (1H, d, J=6.4 Hz), 8.86 (1H, s).

MS (ESI) m/z: 450 [M+H]$^+$.

Example 15

3-Methyl-4-{[(1S*,2R*)-2-(1-methyl-1H-pyrazol-5-yl)cyclopentyl]oxy}-N-(pyrimidin-4-yl)benzenesulfonamide

[Formula 37]

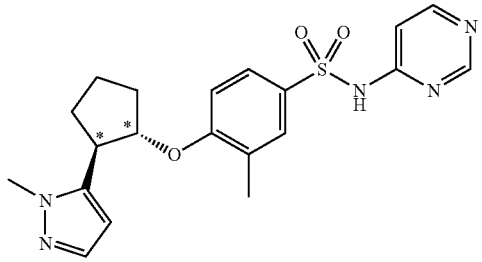

(15a) N-(2,4-Dimethoxybenzyl)-4-fluoro-3-methyl-N-(pyrimidin-4-yl)benzenesulfonamide The reaction and aftertreatment were conducted in the same manner as in Example 1b by using the N-(2,4-dimethoxybenzyl)pyrimidin-4-amine (590 mg, 2.40 mmol) prepared in Example 1a, 4-fluoro-3-methylbenzenesulfonyl chloride (WO2010/079443; 1000 mg, 4.79 mmol), 1,4-diazabicyclo[2.2.2]octane (537 mg, 4.79 mmol) and tetrahydrofuran (20 mL), to yield the title compound (598 mg, 50%) as a colorless oil.

$^1$H-NMR (500 MHz, CDCl$_3$) δ ppm: 2.28 (3H, s), 3.73 (3H, s), 3.78 (3H, s), 5.22 (2H, s), 6.39-6.41 (2H, m), 7.08 (1H, t, J=8.8 Hz), 7.14 (1H, d, J=7.8 Hz), 7.26-7.29 (1H, m), 7.64 (1H, dd, J=2.0, 6.8 Hz), 7.70-7.73 (1H, m), 8.48 (1H, d, J=5.9 Hz), 8.83 (1H, s).

(15b) N-(2,4-Dimethoxybenzyl)-3-methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the N-(2,4-dimethoxybenzyl)-4-fluoro-3-methyl-N-(pyrimidin-4-yl)benzenesulfonamide (500 mg, 1.20 mmol) prepared in Example 15a, the (1S*,2R*)-2-(1-methyl-1H-pyrazol-5-yl)cyclopentanol (209 mg, 1.26 mmol) prepared in Example 1c, sodium hydride (60%; 71.9 mg, 1.80 mmol) and DMF (15 mL), to yield the title compound (356 mg, 53%) as a colorless solid.

$^1$H-NMR (500 MHz, CDCl$_3$) δ ppm: 1.62-1.96 (4H, m), 2.18-2.32 (2H, m), 2.18 (3H, s), 3.40 (1H, dt, J=4.9, 8.3 Hz), 3.75 (3H, s), 3.76 (3H, s), 3.82 (3H, s), 4.71-4.74 (1H, m), 5.23 (2H, s), 6.05 (1H, d, J=2.0 Hz), 6.39 (1H, dd, J=2.4, 10.7 Hz), 6.42 (1H, d, J=2.0 Hz), 6.66 (1H, d, J=8.8 Hz), 7.13 (1H, d, J=8.8 Hz), 7.33 (1H, dd, J=1.0, 5.9 Hz), 7.37-7.39 (1H, m), 7.53 (1H, dd, J=1.0, 2.4 Hz), 7.65 (1H, dd, J=43 Hz), 8.42 (1H, d, J=6.4 Hz), 8.78 (1H, s).

(15c) 3-Methyl-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-3-methyl-4-{[(1S*,2R*)-2-(1-methyl-1H-pyrazol-5-yl)cyclopentyl]oxy}-N-(pyrimidin-4-yl)benzenesulfonamide (356 mg, 0.632 mmol) prepared in Example 15b, triethylsilane (0.20 mL), trifluoroacetic acid (1.0 mL) and dichloromethane (4.0 mL), to yield the title compound (202 mg, 68%) as a colorless solid.

$^1$H-NMR (500 MHz, CDCl$_3$) δ ppm: 1.75-1.93 (4H, m), 2.17-2.32 (2H, m), 2.22 (3H, s), 3.40 (1H, dt, J=4.0, 7.8 Hz), 3.81 (3H, s), 4.71-4.74 (1H, m), 6.05 (1H, d, J=2.0 Hz), 6.69 (1H, d, J=8.8 Hz), 7.23 (1H, d, J=4.4 Hz), 7.40 (1H, d, J=2.0 Hz), 7.69-7.73 (2H, m), 8.46 (1H, d, J=5.9 Hz), 8.81 (1H, s).

MS (ESI) m/z: 413 [M+H]$^+$.

Example 16

3-Methyl-4-{[(1S*,2R*)-2-(1-methyl-1H-pyrazol-5-yl)cyclohexyl]oxy}-N-(pyrimidin-4-yl)benzenesulfonamide

[Formula 38]

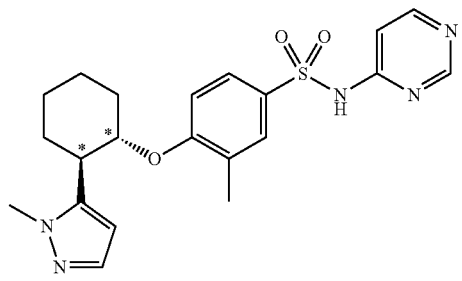

(16a) N-(2,4-Dimethoxybenzyl)-3-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1d by using the N-(2,4-dimethoxybenzyl)-4-fluoro-3-methyl-N-(pyrimidin-4-yl)benzenesulfonamide (0.25 g, 0.60 mmol) prepared in Example 15a, the (1S*,2R*)-2-(1-methyl-1H-pyrazol-5-yl)cyclohexanol (0.11 g, 0.63 mmol) prepared in Example 3a, sodium hydride (63%; 0.040 g, 0.90 mmol) and DMF (10 mL), to yield the title compound (79 mg, 23%) as a colorless amorphous solid.

(16b) 3-Methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the N-(2,4-dimethoxybenzyl)-3-methyl-4-{[(1S*,2R*)-2-(1-methyl-1H-pyrazol-5-yl)cyclohexyl]oxy}-N-(pyrimidin-4-yl)benzenesulfonamide (79 mg, 0.14 mmol) prepared in Example 16a, triethylsilane (0.1 mL), trifluoroacetic acid (1.0 mL) and dichloromethane (4.0 mL), to yield the title compound (49 mg, 84%) as a colorless solid.

$^1$H-NMR (500 MHz, CDCl$_3$) δ ppm: 1.38-1.65 (4H, m), 1.85-1.93 (2H, m), 2.05 (3H, s), 2.05-2.07 (1H, m), 12.29 (1H, m), 3.00 (1H, dt, J=3.4, 9.8 Hz), 3.88 (3H, s), 4.21-4.26 (1H, m), 5.98 (1H, d, J=2.0 Hz), 6.71 (1H, d, J=8.8 Hz), 7.21 (1H, brs), 7.33 (1H, s), 7.62 (1H, brs), 7.67 (1H, d, J=8.3 Hz), 8.47 (1H, d, J=5.9 Hz), 8.84 (1H, s).

MS (ESI) m/z: 427 [M+H]$^+$.

Example 17

3-Methyl-4-{[(1S*,2R*)-2-(1-methyl-1H-pyrazol-5-yl)cycloheptyl]oxy}-N-(pyrimidin-4-yl)benzenesulfonamide

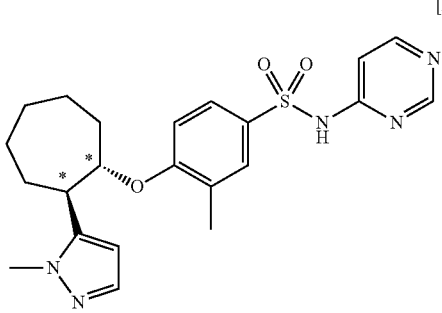

(17a) N-(2,4-Dimethoxybenzyl)-3-methyl-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1d by using the N-(2,4-dimethoxybenzyl)-4-fluoro-3-methyl-N-(pyrimidin-4-yl)benzenesulfonamide (258 mg, 0.62 mmol) prepared in Example 15a, the (1S*,2R*)-2-(1-methyl-1H-pyrazol-5-yl)cycloheptanol (120 mg, 0.62 mmol) prepared in Example 9a, sodium hydride (63%; 35.3 mg, 2.33 mmol) and DMF (10 mL), to yield the title compound (182 mg, 50%) as a colorless oil.

$^1$H-NMR (400 MHz, CDCl$_3$) δ ppm: 1.61-1.99 (10H, m), 2.01 (3H, s), 3.21 (1H, dt, J=3.5, 9.0 Hz), 3.73 (3H, s), 3.77 (3H, s), 3.86 (3H, s), 4.47-4.51 (1H, m), 5.22 (2H, s), 5.98 (1H, d, J=2.0 Hz), 6.37-6.40 (2H, m), 6.61 (1H, d, J=9.0 Hz), 7.13 (1H, d, J=8.2 Hz), 7.32-7.34 (2H, m), 7.45 (1H, s), 7.63 (1H, dd, J=2.0, 9.0 Hz), 8.44 (1H, d, J=5.9 Hz), 8.80 (1H, s).

(17b) 3-Methyl-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1e by using the N-(2,4-dimethoxybenzyl)-3-methyl-4-{[(1S*,2R*)-2-(1-methyl-1H-pyrazol-5-yl)cycloheptyl]oxy}-N-(pyrimidin-4-yl)benzenesulfonamide (182 mg, 0.31 mmol) prepared in Example 17a, triethylsilane (0.15 mL), trifluoroacetic acid (1.0 mL) and dichloromethane (1.0 mL), to yield the title compound (100 mg, 74%) as a colorless solid.

$^1$H-NMR (500 MHz, CDCl$_3$) δ ppm: 1.58-2.04 (10H, m), 2.04 (3H, s), 3.19-3.23 (1H, m), 3.87 (3H, s), 4.47-4.51 (1H, m), 5.98 (1H, s), 6.64 (1H, d, J=8.8 Hz), 7.26-7.33 (2H, m), 7.61 (1H, s), 7.68 (1H, dd, J=43 Hz), 8.49 (1H, brs), 8.97 (1H, brs).

MS (ESI) m/z: 442 [M+H]$^+$.

Example 18

4-{[(1S*,2R*)-2-(1-Ethyl-1H-pyrazol-5-yl)cyclohexyl]oxy}-2,6-difluoro-N-(pyrimidin-4-yl)benzenesulfonamide

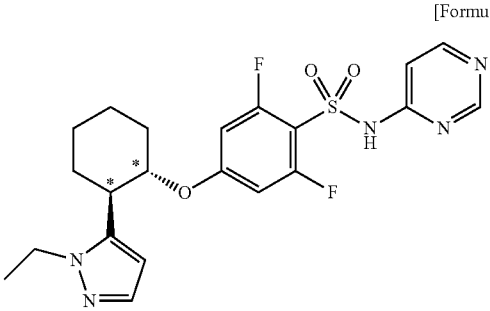

(18a) N-(2,4-Dimethoxybenzyl)-4-{[(1S*,2R*)-2-(1-ethyl-1H-pyrazol-5-yl)cyclohexyl]oxy}-2,6-difluoro-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (0.20 g, 0.45 mmol) prepared in Example 4a, the (1S*,2R*)-2-(1-ethyl-1H-pyrazol-5-yl)cyclohexanol (0.088 g, 0.45 mmol) prepared in Example 5a, sodium hydride (63%; 0.027 g, 0.67 mmol) and DMF (3.0 mL), to yield the title compound (0.085 g, 55%) as a colorless oil.

$^1$H-NMR (500 MHz, CDCl$_3$) δ ppm: 1.39-1.64 (4H, m), 1.44 (3H, t, J=7.3 Hz), 1.86-1.88 (1H, m), 1.94-1.95 (1H, m), 2.02-2.05 (1H, m), 2.23-2.26 (1H, m), 2.90-2.95 (1H, m), 3.77 (3H, s), 3.81 (3H, s), 4.01-4.25 (3H, m), 5.24 (2H, s), 5.98 (1H, d, J=2.0 Hz), 6.29 (2H, d, J=10.7 Hz), 6.41 (1H, dd, J=2.4, 10.7 Hz), 6.43-6.44 (1H, m), 7.16 (1H, d, J=7.3 Hz), 7.21 (1H, d, J=8.3 Hz), 8.38 (1H, d, J=2.0 Hz), 8.44 (1H, d, J=5.9 Hz), 8.78 (1H, s).

(18b) 4-{[(1S*,2R*)-2-(1-Ethyl-1H-pyrazol-5-yl)cyclohexyl]oxy}-2,6-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-2-(1-ethyl-1H-pyrazol-5-yl)cyclohexyl]oxy}-2,6-difluoro-N-(pyrimidin-4-yl)benzenesulfonamide (0.080 g, 0.13 mmol) prepared in Example 18a, triethylsilane (0.10 mL), trifluoroacetic acid (1.0 mL) and dichloromethane (1.0 mL), to yield the title compound (25 mg, 42%) as a colorless solid.

$^1$H-NMR (400 MHz, DMSO-d$_6$) δ ppm: 1.24-1.56 (4H, m), 1.29 (3H, t, J=7.0 Hz), 1.69-1.79 (2H, m), 1.86-1.89 (1H, m), 2.10-2.13 (1H, m), 2.97-3.04 (1H, m), 4.03-4.16 (2H, m), 4.57 (1H, dt, J=3.5, 9.8 Hz), 6.06 (1H, s), 6.73 (2H, d, J=11.7 Hz), 6.92 (1H, brs), 7.22 (1H, brs), 8.29 (1H, brs), 8.58 (1H, s).

MS (ESI) m/z: 464 [M+H]$^+$.

Example 19

5-Chloro-2-fluoro-4-{[(1S*,2R*)-2-(1-methyl-1H-pyrazol-5-yl)cycloheptyl]oxy}-N-(pyrimidin-4-yl)benzenesulfonamide

[Formula 41]

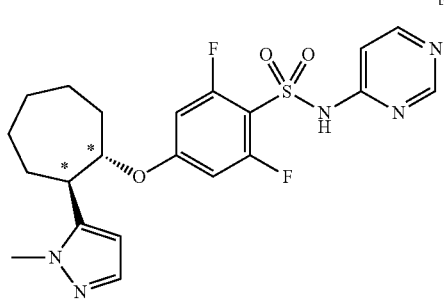

(19a) 5-Chloro-N-(2,4-dimethoxybenzyl)-2-fluoro-4-{[(1S*,2R)-2-(1-methyl-1H-pyrazol-5-yl)cycloheptyl]oxy}-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (300 mg, 0.66 mmol) prepared in Example 2a, the (1S*,2R*)-2-(1-methyl-1H-pyrazol-5-yl)cycloheptanol (134 mg, 0.69 mmol) prepared in Example 9a, sodium hydride (60%; 39.5 mg, 0.99 mmol) and DMF (10 mL), to yield the title compound (202 mg, 49%) as a colorless solid.

$^1$H-NMR (500 MHz, CDCl$_3$) δ ppm: 1.55-1.71 (1H, m), 1.61 (3H, dd, J=4.4, 8.8 Hz), 1.77-1.86 (2H, m), 1.87-1.98 (4H, m), 3.27 (1H, t, J=9.3 Hz), 3.76 (6H, s), 3.91 (3H, s), 4.40 (1H, dd, J=6.1, 12.9 Hz), 5.19 (1H, d, J=16.6 Hz), 5.23 (1H, d, J=16.6 Hz), 6.01 (1H, s), 6.37-6.42 (3H, m), 7.19 (1H, d, J=8.8 Hz), 7.22 (1H, d, J=5.9 Hz), 7.34 (1H, s), 7.94 (1H, d, J=7.3 Hz), 8.46 (1H, d, J=5.9 Hz), 8.80 (1H, s).

(19b) 5-Chloro-2-fluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-4-{[(1S*,2R*)-2-(1-methyl-1H-pyrazol-5-yl)cycloheptyl]oxy}-N-(pyrimidin-4-yl)benzenesulfonamide (202 mg, 0.32 mmol) prepared in Example 19a, triethylsilane (0.10 mL), trifluoroacetic acid (0.5 mL) and dichloromethane (2.0 mL), to yield the title compound (135 mg, 88%) as a colorless solid.

$^1$H-NMR (500 MHz, CDCl$_3$) δ ppm: 1.56-2.00 (10H, m), 3.26 (1H, dt, J=2.9, 9.0 Hz), 3.90 (3H, s), 4.34-4.45 (1H, m), 6.00 (1H, d, J=2.0 Hz), 6.43 (1H, d, J=11.7 Hz), 7.18 (1H, brs), 7.33 (1H, d, J=2.0 Hz), 7.94 (1H, d, J=7.3 Hz), 8.40 (1H, d, J=6.4 Hz), 8.74 (1H, brs).

MS (ESI) m/z: 479 [M+H]$^+$.

Example 20

2,6-Difluoro-4-{[(1S*,2R*)-2-(1-methyl-1H-pyrazol-5-yl)cycloheptyl]oxy}-N-(pyrimidin-4-yl)benzenesulfonamide

[Formula 42]

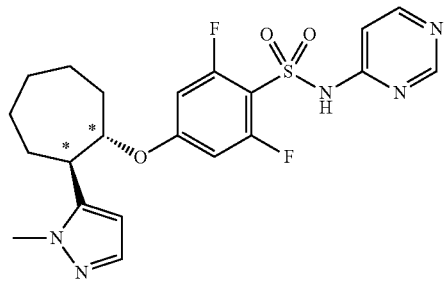

(20a) N-(2,4-Dimethoxybenzyl)-2,6-difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (0.20 g, 0.455 mmol) prepared in Example 4a, the (1S*,2R*)-2-(1-methyl-1H-pyrazol-5-yl)cycloheptanol (0.08 g, 0.409 mmol) prepared in Example 9a, sodium hydride (63%; 0.027 g, 0.682 mmol) and DMF (5 mL), to yield the title compound (0.14 g, 52%) as a colorless amorphous solid.

$^1$H-NMR (500 MHz, CDCl$_3$) δ ppm: 1.60-1.98 (10H, m), 3.15 (1H, dt, J=2.9, 9.3 Hz), 3.77 (3H, s), 3.81 (3H, s), 3.85 (3H, s), 4.36-4.40 (1H, m), 5.25 (2H, s), 5.98 (1H, d, J=2.0 Hz), 6.27 (2H, d, J=10.7 Hz), 6.41 (1H, dd, J=2.4, 8.3 Hz), 6.44 (1H, d, J=2.0 Hz), 7.16 (1H, dd, J=1.5, 5.9 Hz), 7.21 (1H, d, J=8.3 Hz), 7.33 (1H, d, J=2.0 Hz), 8.44 (1H, d, J=5.9 Hz), 8.78 (1H, s).

(20b) 2,6-Difluoro-4-{[(1S*,2R*)-2-(1-methyl-1H-pyrazol-5-yl)cycloheptyl]oxy}-N-(pyrimidin-4-yl)benzenesulfonamide The reaction and aftertreatment were conducted in the same manner as in Example 1e by using the N-(2,4-dimethoxybenzyl)-2,6-difluoro-4-{[(1S*,2R*)-2-(1-methyl-1H-pyrazol-5-yl)cycloheptyl]oxy}-N-(pyrimidin-4-yl)benzenesulfonamide (0.14 g, 0.23 mmol) prepared in Example 20a, triethylsilane (0.15 mL), trifluoroacetic acid (2.0 mL) and dichloromethane (2.0 mL), to yield the title compound (60 mg, 40%) as a colorless solid.

$^1$H-NMR (500 MHz, DMSO-d$_6$) δ ppm: 1.52-1.92 (10H, m), 3.18-3.21 (1H, m), 3.76 (3H, s), 4.73-4.77 (1H, m), 6.10 (1H, d, J=2.0 Hz), 6.72 (2H, d, J=11.2 Hz), 6.94 (1H, brs), 7.19 (1H, d, J=1.5 Hz), 8.29 (1H, brs), 8.58 (1H, s).

MS (ESI) m/z: 464 [M+H]$^+$.

Example 21

2-Fluoro-5-methyl-4-{[(1S*,2R*)-2-(1-methyl-1H-pyrazol-5-yl)cyclohexyl]oxy}-N-(pyrimidin-4-yl)benzenesulfonamide

[Formula 43]

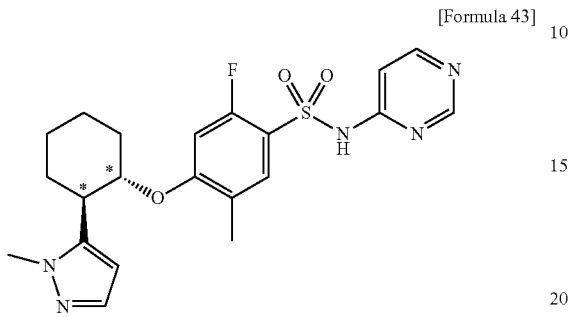

(21a) N-(2,4-Dimethoxybenzyl)-2-fluoro-5-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (0.30 g, 0.69 mmol) prepared in Example 10a, the (1S*,2R*)-2-(1-methyl-1H-pyrazol-5-yl)cyclohexanol (0.21 g, 1.15 mmol) prepared in Example 3a, sodium hydride (63%; 0.070 g, 1.65 mmol) and DMF (10 mL), to yield the title compound (0.17 g, 42%) as a colorless oil.

$^1$H-NMR (500 MHz, CDCl$_3$) δ ppm: 1.40-1.64 (4H, m), 1.86-1.88 (1H, m), 1.92-1.93 (1H, m), 2.03 (1H, m), 2.02 (3H, s), 2.23-2.26 (1H, m), 2.97-3.02 (1H, m), 3.76 (3H, s), 3.78 (3H, s), 3.89 (3H, s), 4.01-4.14 (1H, m), 5.24 (2H, s), 5.98 (1H, d, J=2.0 Hz), 6.36-6.40 (3H, m), 7.19 (1H, d, J=8.8 Hz), 7.28 (1H, dd, J=1.5, 5.9 Hz), 7.35 (1H, d, J=2.0 Hz), 7.66 (1H, d, J=7.8 Hz), 8.43 (1H, d, J=5.9 Hz), 8.77 (1H, d, J=1.0 Hz).

(21b) 2-Fluoro-5-methyl-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the N-(2,4-dimethoxybenzyl)-2-fluoro-5-methyl-4-{[(1S*,2R*)-2-(1-methyl-1H-pyrazol-5-yl)cyclohexyl]oxy}-N-(pyrimidin-4-yl)benzenesulfonamide (0.17 g, 0.29 mmol) prepared in Example 21a, triethylsilane (0.10 mL), trifluoroacetic acid (1.0 mL) and dichloromethane (4.0 mL), to yield the title compound (129 mg, 99%) as a colorless solid.

$^1$H-NMR (500 MHz, CDCl$_3$) δ ppm: 1.40-1.60 (4H, m), 1.85-1.87 (1H, m), 1.91-1.92 (1H, m), 2.04-2.06 (1H, m), 2.05 (3H, s), 2.23-2.25 (1H, m), 2.96-3.02 (1H, m), 3.88 (3H, s), 4.10-4.14 (1H, m), 5.98 (1H, d, J=2.0 Hz), 6.42 (1H, d, J=12.2 Hz), 7.23 (1H, d, J=5.4 Hz), 7.34 (1H, d, J=1.5 Hz), 7.67 (1H, d, J=8.3 Hz), 8.40 (1H, d, J=6.4 Hz), 8.86 (1H, brs).

MS (ESI) m/z: 446 [M+H]$^+$.

Example 22

4-{[(1S*,2R*)-4,4-Dimethyl-2-(1-methyl-1H-pyrazol-5-yl)cyclohexyl]oxy}-2,5-difluoro-N-(pyrimidin-4-yl)benzenesulfonamide

[Formula 44]

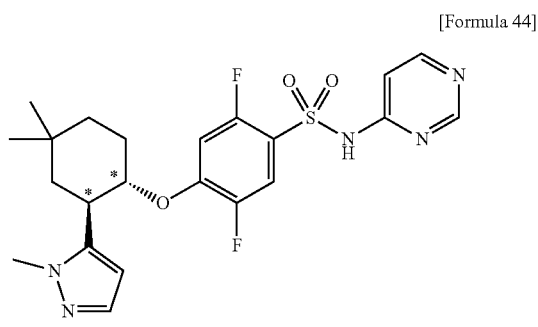 [SMILES: Cn1nccc1[C@H]1CC(C)(C)CC[C@@H]1Oc1cc(F)c(S(=O)(=O)Nc2ccncn2)cc1F]

(22a) 6-Iodo-8,8-dimethyl-1,4-dioxaspiro[4.5]dec-6-ene

A solution of 2-iodo-4,4-dimethylcyclohex-2-en-1-one (Synlett, 2005, 1263-1266; 5.46 g, 21.8 mmol), ethylene glycol (3.00 g, 48.3 mmol), p-toluenesulfonic acid hydrate (100 mg) in benzene (100 mL) was heated under reflux with stirring for 7 hours, and the solvent was subjected to azeotropic distillation to remove water. After allowing to cool, a saturated aqueous solution of sodium hydrogencarbonate (100 mL) was added to the reaction solution, and an organic layer was extracted. The thus obtained organic layer was dried over anhydrous sodium sulfate. After concentration under reduced pressure, the residue was purified with silica gel chromatography (hexane/ethyl acetate=95:5) to yield the title compound (5.78 g, 90%) as a colorless oil.

$^1$H-NMR (500 MHz, CDCl$_3$) δ ppm: 1.03 (6H, s), 1.65-1.68 (2H, m), 1.95-1.98 (2H, m), 3.96-3.99 (2H, m), 4.19-4.22 (2H, m), 6.39 (1H, s).

(22b) 5-(8,8-Dimethyl-1,4-dioxaspiro[4.5]dec-6-en-6-yl)-1-methyl-1H-pyrazole

A solution of the 6-iodo-8,8-dimethyl-1,4-dioxaspiro[4.5]dec-6-ene (1.5 g, 5.10 mmol) prepared in Example 22a, 1-methyl-5-(4,4,5,5-tetramethyl-1,3,2-dioxaboran-2-yl)-1H-pyrazole (1.00 g, 4.81 mmol), tetrakis(triphenylphosphine)palladium(0) (240 mg, 0.208 mmol), and cesium carbonate (3.40 g, 10.4 mmol) in 1,4-dioxane (7.0 mL) and water (3.0 mL) was stirred at 90° C. for 1 hour under microwave irradiation. After allowing to cool, the reaction solution was subjected to extraction with ethyl acetate (100 mL), and the organic layer was dried over anhydrous sodium sulfate. The organic layer was concentrated under reduced pressure, and the residue was purified with column chromatography (hexane/ethyl acetate=4:1) to yield the title compound (580 mg, 49%) as a brown oil.

$^1$H-NMR (500 MHz, CDCl$_3$) δ ppm: 1.11 (6H, s), 1.71-1.74 (2H, m), 1.91-1.93 (2H, m), 3.51-3.54 (2H, m), 3.78 (3H, s), 3.79-3.82 (2H, m), 5.65 (1H, s), 6.16 (1H, d, J=2.0 Hz), 7.40 (1H, d, J=2.0 Hz).

(22c) 4,4-Dimethyl-2-(1-methyl-1H-pyrazol-5-yl)cyclohex-2-en-1-one

A solution of the 5-(8,8-dimethyl-1,4-dioxaspiro[4.5]dec-6-en-6-yl)-1-methyl-1H-pyrazole (580 mg, 2.34 mmol) prepared in Example 22b and 2 M hydrochloric acid (2.0 mL) in THF (5.0 mL) was heated under reflux with stirring for 1 hour. After allowing to cool, a 1 M aqueous sodium hydroxide solution (5.0 mL) was added to the reaction solution, followed by extraction with ethyl acetate (50 mL). The thus obtained organic layer was dried over anhydrous sodium sulfate. After concentration under reduced pressure, the residue was purified with silica gel chromatography (hexane/ethyl acetate=1:1) to yield the title compound (432 mg, 91%) as a colorless oil.

$^1$H-NMR (400 MHz, CDCl$_3$) δ ppm: 1.27 (6H, s), 1.99 (2H, t, J=6.7 Hz), 2.63 (2H, t, J=7.0 Hz), 3.68 (3H, s), 6.13 (1H, d, J=2.0 Hz), 6.78 (1H, s), 7.44 (1H, d, J=2.0 Hz).

(22d) 4,4-Dimethyl-2-(1-methyl-1H-pyrazol-5-yl)cyclohexanol

To a solution of the 4,4-dimethyl-2-(1-methyl-1H-pyrazol-5-yl)cyclohex-2-en-1-one (432 mg, 2.12 mmol) prepared in Example 22c in methanol (6.0 mL), sodium borohydride (200 mg, 5.29 mmol) was added with cooling on ice, and the reaction solution was stirred at room temperature for 1 hour. To the reaction solution, a saturated aqueous solution of ammonium chloride (20 mL) was added, followed by extraction with dichloromethane (50 mL). The thus obtained organic layer was dried over anhydrous sodium sulfate and concentrated under reduced pressure to yield a mixture of the title compound and an allyl alcohol derivative.

A solution of this mixture and palladium hydroxide carbon (10%; 300 mg) in ethanol (6.0 mL) was stirred under a hydrogen atmosphere at room temperature for 3 hours. The reaction solution was filtered through Celite, and the residue was purified with silica gel chromatography (dichloromethane/methanol=97:3) to yield the title compound (347 mg, 79%) in the form of a trans/cis (3:1) mixture.

(22e) N-(2,4-Dimethoxybenzyl)-4-{[(1S*,2R*)-4,4-dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (337 mg, 0.767 mmol) prepared in Example 1b, the 4,4-dimethyl-2-(1-methyl-1H-pyrazol-5-yl)cyclohexanol (160 mg, 0.768 mmol) prepared in Example 22d, sodium hydride (63%; 80 mg, 2.10 mmol) and DMF (4.0 mL), to yield the title compound (293 mg, 61%) as a colorless oil.

$^1$H-NMR (500 MHz, CDCl$_3$) δ ppm: 1.04 (3H, s), 1.12 (3H, s), 1.41-1.47 (1H, m), 1.57-1.62 (2H, m), 1.68-1.81 (2H, m), 2.04-2.08 (1H, m), 3.21-3.26 (1H, m), 3.76 (3H, s), 3.78 (3H, s), 3.91 (3H, s), 4.08 (1H, dt, J=4.4, 11.2 Hz), 5.19 (1H, d, J=17.1 Hz), 5.23 (1H, d, J=17.1 Hz), 6.01 (1H, d, J=2.0 Hz), 6.39-6.41 (2H, m), 6.45 (1H, dd, J=6.4, 11.2 Hz), 7.17-7.18 (2H, m), 7.33 (1H, d, J=2.0 Hz), 7.67 (1H, dd, J=6.8, 10.3 Hz), 8.45 (1H, d, J=5.9 Hz), 8.78 (1H, d, J=1.0 Hz).

(22f) 4-{[(1S*,2R*)-4,4-Dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-4,4-dimethyl-2-(1-methyl-1H-pyrazol-5-yl)cyclohexyl]oxy}-2,5-difluoro-N-(pyrimidin-4-yl)benzenesulfonamide (293 mg, 0.467 mmol) prepared in Example 22e, triethylsilane (0.40 mL), trifluoroacetic acid (4.0 mL) and dichloromethane (4.0 mL), to yield the title compound (198 mg, 89%) as a colorless solid.

$^1$H-NMR (500 MHz, DMSO-d$_6$) δ ppm: 0.97 (3H, s), 1.08 (3H, s), 1.44-1.69 (5H, m), 1.98-2.02 (1H, m), 3.26 (1H, dt, J=4.4, 10.3 Hz), 3.79 (3H, s), 4.52 (1H, dt, J=4.4, 10.3 Hz), 6.05 (1H, d, J=2.0 Hz), 6.94 (1H, brs), 7.18 (1H, d, J=2.0 Hz), 7.26 (1H, brs), 7.61 (1H, brs), 8.24 (1H, brs), 8.56 (1H, s).

MS (ESI) m/z: 478 [M+H]$^+$.

Example 23

4-{[(1S*,2R*)-5,5-Dimethyl-2-(1-methyl-1H-pyrazol-5-yl)cyclohexyl]oxy}-2,5-difluoro-N-(pyrimidin-4-yl)benzenesulfonamide

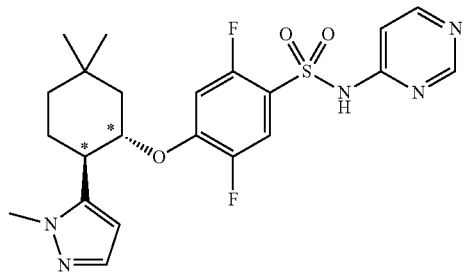

[Formula 45]

(23a) 6-Iodo-9,9-dimethyl-1,4-dioxaspiro[4.5]dec-6-ene

The reaction and aftertreatment were conducted in the same manner as in Example 22a by using 2-iodo-5,5-dimethylcyclohex-2-en-1-one (J. Org. Chem., 1994, 59, 5393-5396; 6.10 g, 24.4 mmol), ethylene glycol (3.00 g, 48.3 mmol), p-toluenesulfonic acid hydrate (230 mg, 1.22 mmol) and benzene (70 mL), to yield the title compound (3.33 g, 46%) as a brown oil.

$^1$H-NMR (500 MHz, CDCl$_3$) δ ppm: 1.01 (6H, s), 1.84 (2H, s), 1.96 (2H, d, J=3.9 Hz), 3.95-3.98 (2H, m), 4.18-4.21 (2H, m), 6.59 (1H, t, J=4.4 Hz).

(23b) 5-(9,9-Dimethyl-1,4-dioxaspiro[4.5]dec-6-en-6-yl)-1-methyl-1H-pyrazole

The reaction and aftertreatment were conducted in the same manner as in Example 12a by using the 6-iodo-9,9-dimethyl-1,4-dioxaspiro[4.5]dec-6-ene (1.4 g, 4.76 mmol) prepared in Example 23a, 1-methyl-5-(4,4,5,5-tetramethyl-1,3,2-dioxaboran-2-yl)-1H-pyrazole (1.00 g, 4.81 mmol), tetrakis(triphenylphosphine)palladium (0) (240 mg, 0.208 mmol), cesium carbonate (3.40 g, 10.4 mmol), 1,4-dioxane (10 mL) and water (5.0 mL), to yield the title compound (758 mg, 64%) as a colorless oil.

$^1$H-NMR (500 MHz, CDCl$_3$) δ ppm: 1.09 (6H, s), 1.80 (2H, s), 2.07 (2H, d, J=3.9 Hz), 3.44-3.47 (2H, m), 3.77-3.79 (2H, m), 3.80 (3H, s), 5.88 (1H, t, J=3.9 Hz), 6.17 (1H, d, J=1.5 Hz), 7.41 (1H, d, J=2.0 Hz).

(23c) 5,5-Dimethyl-2-(1-methyl-1H-pyrazol-5-yl)cyclohex-2-en-1-one

The reaction and aftertreatment were conducted in the same manner as in Example 22c by using the 5-(9,9-dimethyl-1,4-dioxaspiro[4.5]dec-6-en-6-yl)-1-methyl-1H-pyrazole (758 mg, 3.05 mmol) prepared in Example 23b, 2 M hydrochloric acid (2.0 mL) and THF (5.0 mL), to yield the title compound (581 mg, 93%) as a colorless oil.

$^1$H-NMR (500 MHz, CDCl$_3$) δ ppm: 1.14 (6H, s), 1.58 (2H, s), 2.46 (2H, d, J=2.9 Hz), 3.70 (3H, s), 6.14 (1H, d, J=1.5 Hz), 6.98 (1H, t, J=3.9 Hz), 7.44 (1H, d, J=1.5 Hz).

(23d) (1S*,2R*)-5,5-Dimethyl-2-(1-methyl-1H-pyrazol-5-yl)cyclohexanol

To a solution of the 5,5-dimethyl-2-(1-methyl-1H-pyrazol-5-yl)cyclohex-2-en-1-one (581 mg, 2.84 mmol) prepared in Example 23c in methanol (6.0 mL), sodium borohydride (200 mg, 5.29 mmol) was added with cooling on ice, and the reaction solution was stirred at room temperature for 30 minutes. To the reaction solution, a saturated aqueous solution of ammonium chloride (50 mL) was added, followed by extraction with ethyl acetate (100 mL). The thus obtained organic layer was dried over anhydrous sodium sulfate. After concentration under reduced pressure, the residue was purified with silica gel chromatography (dichloromethane/methanol=98:2) to yield the title compound (40 mg, 6.8%) as a colorless oil.

$^1$H-NMR (500 MHz, CDCl$_3$) δ ppm: 1.01 (3H, s), 1.02 (3H, s), 1.29-1.34 (2H, m), 1.44-1.48 (1H, m), 1.55-1.64 (1H, m), 1.72-1.83 (2H, m), 2.47-2.52 (1H, m), 3.81 (1H, dt, J=4.4, 11.2 Hz), 3.84 (3H, s), 6.08 (1H, d, J=1.5 Hz), 7.42 (1H, d, J=1.5 Hz).

(23e) N-(2,4-Dimethoxybenzyl)-4-{[(1S*,2R*)-5,5-dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (85 mg, 0.193 mmol) prepared in Example 1b, the (1S*,2R*)-5,5-dimethyl-2-(1-methyl-1H-pyrazol-5-yl)cyclohexanol (40 mg, 0.192 mmol) prepared in Example 23d, sodium hydride (63%; 30 mg, 0.788 mmol) and DMF (2.0 mL), to yield the title compound (100 mg, 83%) as a colorless oil.

$^1$H-NMR (500 MHz, CDCl$_3$) δ ppm: 1.06 (3H, s), 1.10 (3H, s), 1.39-1.48 (2H, m), 1.55-1.62 (1H, m), 1.81-1.96 (3H, m), 2.91-2.96 (1H, m), 3.77 (3H, s), 3.78 (3H, s), 3.90 (3H, s), 4.30 (1H, dt, J=3.9, 11.2 Hz), 5.19 (1H, d, J=16.6 Hz), 5.24 (1H, d, J=17.1 Hz), 6.05 (1H, d, J=2.0 Hz), 6.38-6.42 (3H, m), 7.18-7.20 (2H, m), 7.36 (1H, d, J=1.5 Hz), 7.67 (1H, dd, J=6.4, 9.8 Hz), 8.46 (1H, d, J=5.9 Hz), 8.79 (1H, d, J=1.0 Hz).

(23f) 4-{[(1S*,2R*)-5,5-Dimethyl-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-5,5-dimethyl-2-(1-methyl-1H-pyrazol-5-yl)cyclohexyl]oxy}-2,5-difluoro-N-(pyrimidin-4-yl)benzenesulfonamide (100 mg, 0.159 mmol) prepared in Example 23e, triethylsilane (0.20 mL), trifluoroacetic acid (2.0 mL) and dichloromethane (2.0 mL), to yield the title compound (70 mg, 92%) as a colorless solid.

$^1$H-NMR (500 MHz, DMSO-d$_6$) δ ppm: 0.98 (3H, s), 1.09 (3H, s), 1.36-1.43 (3H, m), 1.68-1.90 (3H, m), 3.01 (1H, dt, J=4.4, 11.7 Hz), 3.77 (3H, s), 4.68 (1H, dt, J=3.9, 10.7 Hz), 6.21 (1H, d, J=2.0 Hz), 6.98 (1H, brs), 7.08 (1H, dd, J=6.4, 11.2 Hz), 7.19 (1H, d, J=2.0 Hz), 7.60-7.63 (1H, m), 8.24 (1H, brs), 8.57 (1H, s).

MS (ESI) m/z: 478 [M+H]$^+$.

Example 24

3-Chloro-2-fluoro-4-{[(1S*,2R*)-2-(1-methyl-1H-pyrazol-5-yl)cyclohexyl]oxy}-N-(pyrimidin-4-yl)benzenesulfonamide

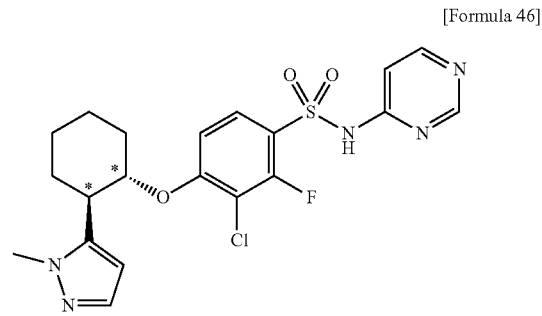 [SMILES: Cn1nccc1[C@H]1CCCC[C@@H]1Oc1ccc(S(=O)(=O)Nc2ccncn2)c(F)c1Cl]

[Formula 46]

(24a) 3-Chloro-N-(2,4-dimethoxybenzyl)-2,4-difluoro-N-(pyrimidin-4-yl)benzenesulfonamide The reaction and aftertreatment were conducted in the same manner as in Example 1b by using the N-(2,4-dimethoxybenzyl)pyrimidin-4-amine (1.00 g, 4.07 mmol) prepared in Example 1a, 3-chloro-2,4-difluorobenzenesulfonyl chloride (1.51 g, 6.11 mmol), 1,4-diazabicyclo[2.2.2]octane (0.69 g, 6.11 mmol) and THF (20 mL), to yield the title compound (0.983 g, 53%) as a colorless amorphous solid.

$^1$H-NMR (500 MHz, CDCl$_3$) δ ppm: 3.78 (3H, s), 3.81 (3H, s), 5.25 (2H, s), 6.41-6.43 (2H, m), 7.11-7.15 (2H, m), 7.22 (1H, d, J=8.8 Hz), 8.01-8.05 (1H, m), 8.47 (1H, d, J=5.9 Hz), 8.75 (1H, d, J=1.0 Hz).

(24b) 3-Chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1d by using the 3-chloro-N-(2,4-dimethoxybenzyl)-2,4-difluoro-N-(pyrimidin-4-yl)benzenesulfonamide (0.30 g, 0.69 mmol) prepared in Example 24a, the (1S*,2R*)-2-(1-methyl-1H-pyrazol-5-yl)cyclohexanol (0.12 g, 0.66 mmol) prepared in Example 3a, sodium hydride (63%; 0.050 g, 1.31 mmol) and DMF (2.0 mL), to yield the title compound (314 mg, 77%) as a colorless amorphous solid.

$^1$H-NMR (500 MHz, CDCl$_3$) δ ppm: 1.41-1.63 (4H, m), 1.88-1.97 (2H, m), 2.07-2.09 (1H, m), 2.23-2.26 (1H, m), 3.03-3.08 (1H, m), 3.77 (3H, s), 3.78 (3H, s), 3.92 (3H, s), 4.29 (1H, dt, J=3.9, 10.3 Hz), 5.21 (1H, d, J=17.1 Hz), 5.26 (1H, d, J=17.1 Hz), 6.05 (1H, d, J=2.0 Hz), 6.39-6.41 (2H, m), 6.60 (1H, d, J=9.3 Hz), 7.16 (1H, dd, J=1.5, 5.9 Hz), 7.19 (1H, d, J=9.3 Hz), 7.36 (1H, d, J=2.0 Hz), 7.81 (1H, dd, J=7.8, 8.8 Hz), 8.44 (1H, d, J=5.9 Hz), 8.76 (1H, s).

(24c) 3-Chloro-2-fluoro-4-{[(1S*,2R*)-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the 3-chloro-N-(2,4-dimethoxybenzyl)-2-fluoro-4-{[(1S*,2R*)-2-(1-methyl-1H-pyrazol-5-yl)cyclohexyl]oxy}-N-(pyrimidin-4-yl)benzenesulfonamide (314 mg, 0.51 mmol) prepared in Example 24b, triethylsilane (0.50 mL), trifluoroacetic acid (5.0 mL) and dichloromethane (5.0 mL), to yield the title compound (183 mg, 77%) as a colorless solid.
¹H-NMR (500 MHz, CDCl₃) δ ppm: 1.38-1.70 (4H, m), 1.87-1.95 (2H, m), 2.06-2.10 (1H, m), 2.28 (1H, m), 3.03-3.08 (1H, m), 3.92 (3H, s), 4.28 (1H, dt, J=4.4, 10.7 Hz), 6.04 (1H, d, J=2.0 Hz), 6.61 (1H, dd, J=1.0, 9.3 Hz), 7.20-7.21 (1H, m), 7.36 (1H, d, J=2.0 Hz), 7.78 (1H, t, J=7.8 Hz), 8.35 (1H, d, J=6.4 Hz), 8.81 (1H, s).
MS (ESI) m/z: 466[M+H]⁺.

Example 25

3-Chloro-2-fluoro-4-{[(1S*,2R*)-2-(1-methyl-1H-pyrazol-5-yl)cyclopentyl]oxy}-N-(pyrimidin-4-yl)benzenesulfonamide

[Formula 47]

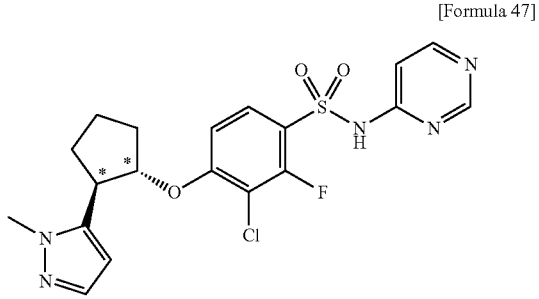 [SMILES: Cn1nccc1[C@H]1CCC[C@@H]1Oc1ccc(S(=O)(=O)Nc2ccncn2)c(F)c1Cl]

(25a) 3-Chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the 3-chloro-N-(2,4-dimethoxybenzyl)-2,4-difluoro-N-(pyrimidin-4-yl)benzenesulfonamide (463 mg, 1.02 mmol) prepared in Example 24a, the (1S*,2R*)-2-(1-methyl-1H-pyrazol-5-yl)cyclopentanol (169 mg, 1.02 mmol) prepared in Example 1c, sodium hydride (63%; 50 mg, 1.31 mmol) and DMF (3.0 mL), to yield the title compound (347 mg, 57%) as a colorless amorphous solid.
¹H-NMR (500 MHz, CDCl₃) δ ppm: 1.80-1.98 (4H, m), 2.22-2.35 (2H, m), 3.50 (1H, dt, J=4.9, 8.8 Hz), 3.76 (3H, s), 3.80 (3H, s), 3.87 (3H, s), 4.73-4.76 (1H, m), 5.24 (1H, d, J=17.1 Hz), 5.29 (1H, d, J=17.1 Hz), 6.08 (1H, d, J=2.0 Hz), 6.40-6.42 (2H, m), 6.63 (1H, dd, J=1.0, 8.8 Hz), 7.18 (1H, dd, J=1.5, 5.9 Hz), 7.20 (1H, d, J=7.8 Hz), 7.42 (1H, d, J=1.5 Hz), 7.88 (1H, dd, J=7.8, 8.8 Hz), 8.44 (1H, d, J=6.4 Hz), 8.76 (1H, d, J=1.0 Hz).

(25b) 3-Chloro-2-fluoro-4-{[(1S*,2R*)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the 3-chloro-N-(2,4-dimethoxybenzyl)-2-fluoro-4-{[(1S*,2R*)-2-(1-methyl-1H-pyrazol-5-yl)cyclopentyl]oxy}-N-(pyrimidin-4-yl)benzenesulfonamide (344 mg, 0.31 mmol) prepared in Example 25a, triethylsilane (0.50 mL), trifluoroacetic acid (5.0 mL) and dichloromethane (5.0 mL), to yield the title compound (227 mg, 88%) as a colorless solid.
¹H-NMR (500 MHz, CDCl₃) δ ppm: 1.78-1.98 (4H, m), 2.22-2.35 (2H, m), 3.49 (1H, dt, J=4.9, 8.3 Hz), 3.86 (3H, s), 4.72-4.75 (1H, m), 6.07 (1H, d, J=2.0 Hz), 6.64 (1H, d, J=7.8 Hz), 7.24-7.25 (1H, m), 7.42 (1H, d, J=2.0 Hz), 7.86 (1H, dd, J=7.8, 8.8 Hz), 8.37 (1H, d, J=6.4 Hz), 8.84 (1H, brs).
MS (ESI) m/z: 452 [M+H]⁺.

Example 26

4-{[(1S*,2R*)-5,5-Difluoro-2-(1-methyl-1H-pyrazol-5-yl)cyclohexyl]oxy}-2-fluoro-3-methyl-N-(pyrimidin-4-yl)benzenesulfonamide

[Formula 48]

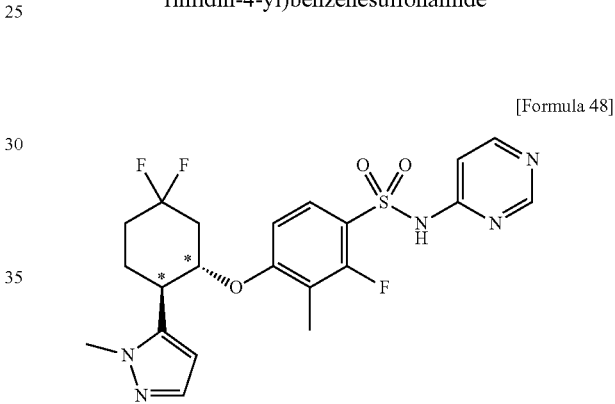

(26a) 2,4-Difluoro-3-methylbenzenesulfonyl chloride

To 1,3-difluoro-2-methylbenzene (5.00 g, 39.0 mmol), chlorosulfuric acid (10.5 mL, 158 mmol) was added with cooling on ice, and the reaction solution was stirred at room temperature for 5 hours. Water (100 mL) was added to the reaction solution with cooling on ice, followed by extraction with dichloromethane (100 mL). The thus obtained organic layer was dried over anhydrous sodium sulfate. After concentration under reduced pressure, the residue was purified with silica gel chromatography to yield the title compound (8.65 g, 98%) as a colorless amorphous solid.
¹H-NMR (500 MHz, CDCl₃) δ ppm: 2.32 (3H, s), 7.05 (1H, dt, J=1.5, 8.8 Hz), 7.82-7.87 (1H, m).

(26b) N-(2,4-Dimethoxybenzyl)-2,4-difluoro-3-methyl-N-(pyrimidin-4-yl)benzenesulfonamide The reaction and aftertreatment were conducted in the same manner as in Example 1b by using the N-(2,4-dimethoxybenzyl)pyrimidin-4-amine (1.00 g, 4.08 mmol) prepared in Example 1a, the 2,4-difluoro-3-methylbenzenesulfonyl chloride (1.85 g, 8.15 mmol) prepared in Example 26a, 1,4-diazabicyclo[2.2.2]octane (0.91 g, 8.15 mmol), and THF (20 mL), to yield the title compound (1.75 g, 99%) as a colorless amorphous solid.

¹H-NMR (500 MHz, CDCl₃) δ ppm: 2.05 (3H, s), 3.78 (3H, s), 3.81 (3H, s), 5.28 (2H, s), 6.41-6.44 (2H, m), 6.99 (1H, d, J=1.5, 9.3 Hz), 7.20 (1H, dd, J=1.5, 5.9 Hz), 7.22 (1H, d, J=8.3 Hz), 7.92-7.96 (1H, m), 8.44 (1H, d, J=5.9 Hz), 8.75 (1H, d, J=1.0 Hz).

(26c) 4-{[(1S*,2R*)-5,5-Difluoro-2-(1-methyl-1H-pyrazol-5-yl)cyclohexyl]oxy}-N-(2,4-dimethoxybenzyl)-2-fluoro-3-methyl-N-(pyrimidin-4-yl)benzenesulfonamide The reaction and aftertreatment were conducted in the same manner as in Example 1d by using the N-(2,4-dimethoxybenzyl)-2,4-difluoro-3-methyl-N-(pyrimidin-4-yl)benzenesulfonamide (60 mg, 0.14 mmol) prepared in Example 26b, the (1S*,2R*)-5,5-difluoro-2-(1-methyl-1H-pyrazol-5-yl)cyclohexanol (30 mg, 0.14 mmol) prepared in Example 12b, sodium hydride (63%; 20 mg, 0.21 mmol) and DMF (5.0 mL), to yield the title compound (51 mg, 59%) as a colorless solid.

¹H-NMR (500 MHz, CDCl₃) δ ppm: 1.90-2.17 (4H, m), 1.90 (3H, s), 2.30-2.31 (1H, m), 2.73-2.80 (1H, m), 3.07-3.12 (1H, m), 3.77 (3H, s), 3.79 (3H, s), 3.88 (3H, s), 4.51 (1H, dt, J=4.4, 10.7 Hz), 5.26 (2H, s), 6.04 (1H, d, J=2.0 Hz), 6.39-6.42 (2H, m), 6.54 (1H, d, J=8.8 Hz), 7.20 (1H, d, J=7.8 Hz), 7.25 (1H, dd, J=1.5, 5.9 Hz), 7.38 (1H, d, J=2.0 Hz), 7.80 (1H, t, J=8.3 Hz), 8.42 (1H, d, J=5.9 Hz), 8.76 (1H, d, J=1.0 Hz).

(26d) 4-{[(1S*,2R*)-5,5-Difluoro-2-(1-methyl-1H-pyrazol-5-yl)cyclohexyl]oxy}-2-fluoro-3-methyl-N-(pyrimidin-4-yl)benzenesulfonamide The reaction and aftertreatment were conducted in the same manner as in Example 1e by using the 4-{[(1S*,2R*)-5,5-difluoro-2-(1-methyl-1H-pyrazol-5-yl)cyclohexyl]oxy}-N-(2,4-dimethoxybenzyl)-2-fluoro-3-methyl-N-(pyrimidin-4-yl)benzenesulfonamide (51 mg, 0.081 mmol) prepared in Example 26c, triethylsilane (0.10 mL), trifluoroacetic acid (0.5 mL) and dichloromethane (2.0 mL), to yield the title compound (31 mg, 79%) as a colorless solid.

¹H-NMR (500 MHz, CDCl₃) δ ppm: 1.90-2.12 (4H, m), 1.93 (3H, s), 2.31-2.35 (1H, m), 2.73-2.78 (1H, m), 3.07-3.12 (1H, m), 3.89 (3H, s), 4.50 (1H, dt, J=3.9, 10.7 Hz), 6.05 (1H, d, J=2.0 Hz), 6.55 (1H, d, J=8.8 Hz), 7.20 (1H, brs), 7.40 (1H, d, J=2.0 Hz), 7.76 (1H, t, J=8.8 Hz), 8.42 (1H, brs), 8.78 (1H, brs).

MS (ESI) m/z: 482 [M+H]⁺.

Example 27

4-{[(1S*,2R*)-5,5-Difluoro-2-(1-methyl-1H-pyrazol-5-yl)cyclohexyl]oxy}-2-fluoro-5-methyl-N-(pyrimidin-4-yl)benzenesulfonamide (27a) 4-{[(1S*,2R*)-5,5-Difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (180 mg, 0.413 mmol) prepared in Example 10a, the (1S*,2R*)-5,5-difluoro-2-(1-methyl-1H-pyrazol-5-yl)cyclohexanol (89 mg, 0.413 mmol) prepared in Example 12b, sodium hydride (63%; 60 mg, 0.620 mmol) and DMF (5.0 mL), to yield the title compound (172 mg, 66%) as a colorless solid.

¹H-NMR (500 MHz, CDCl₃) δ ppm: 1.89-2.30 (5H, m), 2.05 (3H, s), 2.67-2.74 (1H, m), 3.07-3.12 (1H, m), 3.76 (3H, s), 3.78 (3H, s), 3.89 (3H, s), 4.36 (1H, dt, J=4.9, 10.7 Hz), 5.23 (2H, s), 6.04 (1H, d, J=2.0 Hz), 6.35-6.41 (3H, m), 7.19 (1H, d, J=8.3 Hz), 7.25 (1H, dd, J=1.0, 6.8 Hz), 7.38 (1H, d, J=1.0 Hz), 7.70 (1H, d, J=7.8 Hz), 8.43 (1H, d, J=5.9 Hz), 8.77 (1H, s).

(27b) 4-{[(1S*,2R*)-5,5-Difluoro-2-(1-methyl-1H-pyrazol-5-yl)cyclohexyl]oxy}-2-fluoro-5-methyl-N-(pyrimidin-4-yl)benzenesulfonamide The reaction and aftertreatment were conducted in the same manner as in Example 1e by using the 4-{[(1S*,2R*)-5,5-difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide (172 mg, 0.272 mmol) prepared in Example 27a, triethylsilane (0.10 mL), trifluoroacetic acid (0.5 mL) and dichloromethane (3.0 mL), to yield the title compound (131 mg, 99%) as a colorless solid.

¹H-NMR (500 MHz, CDCl₃) δ ppm: 1.91-2.33 (5H, m), 2.05 (3H, s), 2.70-2.74 (1H, m), 3.07-3.12 (1H, m), 3.88 (3H, s), 4.38 (1H, dt, J=4.4, 10.7 Hz), 6.05 (1H, d, J=2.0 Hz), 6.42 (1H, d, J=11.7 Hz), 6.15 (1H, d, J=5.9 Hz), 7.36 (1H, s), 7.71 (1H, d, J=8.3 Hz), 8.36 (1H, d, J=6.4 Hz), 8.70 (1H, s).

MS (ESI) m/z: 482 [M+H]⁺.

Example 28

4-{[(1S*,2R*)-4,4-Dimethyl-2-(1-methyl-1H-pyrazol-5-yl)cyclopentyl]oxy}-2,5-difluoro-N-(pyrimidin-4-yl)benzenesulfonamide

[Formula 49]

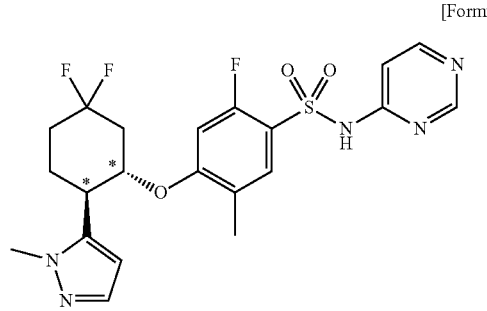

[Formula 50]

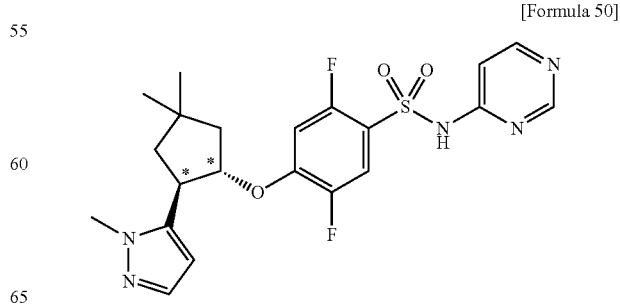

(28a) 6-Iodo-8,8-dimethyl-1,4-dioxaspiro[4.4]non-6-ene

The reaction and aftertreatment were conducted in the same manner as in Example 22a by using 2-iodo-4,4-dimethylcyclopent-2-en-1-one (U.S. Pat. No. 6,222,048; 3.77 g, 16.0 mmol), ethylene glycol (2.0 mL, 32.2 mmol), p-toluenesulfonic acid hydrate (100 mg, 0.526 mmol) and benzene (60 mL), to yield the title compound (3.30 g, 74%) as a colorless oil.

$^1$H-NMR (500 MHz, CDCl$_3$) δ ppm: 1.13 (6H, s), 1.95 (2H, s), 3.95-3.98 (2H, m), 4.18-4.20 (2H, m), 6.23 (1H, s).

(28b) 5-(8,8-Dimethyl-1,4-dioxaspiro[4.4]non-6-en-6-yl)-1-methyl-1H-pyrazole The reaction and aftertreatment were conducted in the same manner as in Example 12a by using the 6-iodo-8,8-dimethyl-1,4-dioxaspiro[4.4]non-6-ene (1.30 g, 4.64 mmol) prepared in Example 28a, 1-methyl-5-(4,4,5,5-tetramethyl-1,3,2-dioxaboran-2-yl)-1H-pyrazole (1.30 g, 6.25 mmol), [1,1'-bis(diphenylphosphino)ferrocene]dichloropalladium (II) (200 mg, 0.245 mmol), cesium carbonate (3.30 g, 10.1 mmol), 1,4-dioxane (10 mL) and water (5.0 mL), to yield the title compound (1.07 g, 98%) as an orange oil.

$^1$H-NMR (500 MHz, CDCl$_3$) δ ppm: 1.23 (6H, s), 2.03 (2H, s), 3.77-3.79 (2H, m), 3.85-3.90 (2H, m), 3.86 (3H, s), 5.95 (1H, s), 6.27 (1H, d, J=2.0 Hz), 7.43 (1H, d, J=2.0 Hz).

(28c) 4,4-Dimethyl-2-(1-methyl-1H-pyrazol-5-yl)cyclopent-2-en-1-one

The reaction and aftertreatment were conducted in the same manner as in Example 22c by using the 5-(8,8-dimethyl-1,4-dioxaspiro[4.4]non-6-en-6-yl)-1-methyl-1H-pyrazole (1.07 g, 4.56 mmol) prepared in Example 28b, 2 M hydrochloric acid (5.0 mL) and THF (5.0 mL), to yield the title compound (780 mg, 90%) as a light brown solid.

$^1$H-NMR (500 MHz, CDCl$_3$) δ ppm: 1.33 (6H, s), 2.46 (2H, s), 3.90 (3H, s), 6.55 (1H, d, J=2.0 Hz), 7.47 (1H, d, J=2.0 Hz), 7.50 (1H, s).

(28d) 4,4-Dimethyl-2-(1-methyl-1H-pyrazol-5-yl)cyclopentanone

A solution of the 4,4-dimethyl-2-(1-methyl-1H-pyrazol-5-yl)cyclopent-2-en-1-one (780 mg, 4.10 mmol) prepared in Example 28c and palladium carbon (5%; 700 mg) in ethanol (8.0 mL) was stirred under a hydrogen atmosphere for 6 hours. The reaction solution was filtered through Celite to yield the title compound (750 mg, 95%) in a crude form as a yellow oil.

$^1$H-NMR (500 MHz, CDCl$_3$) δ ppm: 1.19 (3H, s), 1.28 (3H, s), 2.02 (1H, t, J=12.2 Hz), 2.20-2.32 (3H, m), 3.68 (1H, dd, J=9.3, 12.2 Hz), 6.01 (1H, d, J=2.0 Hz), 7.40 (1H, d, J=2.0 Hz).

(28e) (1S*,2R*)-4,4-Dimethyl-2-(1-methyl-1H-pyrazol-5-yl)cyclopentanol

To a solution of the 4,4-dimethyl-2-(1-methyl-1H-pyrazol-5-yl)cyclopentanone (750 mg, 3.90 mmol) prepared in Example 28d in methanol (8.0 mL), sodium borohydride (150 mg, 3.97 mmol) was added with cooling on ice, and the reaction solution was stirred at room temperature for 1 hour. To the reaction solution, water (50 mL) was added, followed by extraction with ethyl acetate (100 mL). The thus obtained organic layer was dried over anhydrous sodium sulfate. After concentration under reduced pressure, the residue was purified with silica gel chromatography (dichloromethane/methanol=97:3) to yield the title compound (390 mg, 52%) as a colorless oil.

$^1$H-NMR (500 MHz, CDCl$_3$) δ ppm: 1.10 (3H, s), 1.18 (3H, s), 1.54 (1H, dd, J=11.2, 13.2 Hz), 1.59 (1H, dd, J=7.8, 12.7 Hz), 1.93 (1H, dd, J=7.8, 12.7 Hz), 1.99 (1H, dd, J=7.8, 13.2 Hz), 3.11-3.16 (2H, m), 3.78 (3H, s), 4.21-4.27 (1H, m), 6.04 (1H, d, J=2.0 Hz), 7.32 (1H, d, J=2.0 Hz).

(28f) N-(2,4-Dimethoxybenzyl)-4-{[(1S*,2R*)-4,4-dimethyl-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (290 mg, 0.660 mmol) prepared in Example 1b, the (1S*,2R*)-4,4-dimethyl-2-(1-methyl-1H-pyrazol-5-yl)cyclopentanol (130 mg, 0.669 mmol) prepared in Example 28e, sodium hydride (63%; 60 mg, 1.58 mmol) and DMF (3.0 mL), to yield the title compound (309 mg, 76%) as a colorless oil.

$^1$H-NMR (500 MHz, CDCl$_3$) δ ppm: 1.19 (3H, s), 1.24 (3H, s), 1.71-1.77 (2H, m), 2.07 (1H, ddd, J=1.5, 7.8, 13.2 Hz), 2.14 (1H, dd, J=7.8, 13.7 Hz), 3.69-3.75 (1H, m), 3.76 (3H, s), 3.79 (3H, s), 3.88 (3H, s), 4.58-4.62 (1H, m), 5.21 (1H, d, J=17.1 Hz), 5.25 (1H, d, J=17.1 Hz), 6.08 (1H, d, J=2.0 Hz), 6.39-6.42 (2H, m), 6.47 (1H, dd, J=6.4, 10.7 Hz), 7.17-7.20 (2H, m), 7.40 (1H, d, J=2.0 Hz), 7.75 (1H, dd, J=6.8, 10.3 Hz), 8.46 (1H, d, J=5.9 Hz), 8.79 (1H, d, J=1.0 Hz).

(28g) 4-{[(1S*,2R*)-4,4-Dimethyl-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1e by using the N-(2,4-dimethoxybenzyl)-4-{[(1S*,2R*)-4,4-dimethyl-2-(1-methyl-1H-pyrazol-5-yl)cyclopentyl]oxy}-2,5-difluoro-N-(pyrimidin-4-yl)benzenesulfonamide (309 mg, 0.504 mmol) prepared in Example 28f, triethylsilane (0.30 mL), trifluoroacetic acid (3.0 mL) and dichloromethane (3.0 mL), to yield the title compound (212 mg, 91%) as a colorless solid.

$^1$H-NMR (500 MHz, CD$_3$OD) δ ppm: 1.18 (3H, s), 1.23 (3H, s), 1.69 (1H, dd, J=4.9, 13.7 Hz), 1.74 (1H, t, J=12.2 Hz), 2.07 (1H, dd, J=8.3, 13.2 Hz), 2.24 (1H, dd, J=7.8, 13.7 Hz), 3.73-3.78 (1H, m), 3.81 (3H, s), 4.83-4.91 (1H, m), 6.23 (1H, d, J=2.0 Hz), 6.88 (1H, dd, J=6.8, 11.7 Hz), 7.03 (1H, d, J=6.4 Hz), 7.36 (1H, d, J=2.0 Hz), 7.75 (1H, dd, J=6.8, 10.3 Hz), 8.27 (1H, d, J=6.4 Hz), 8.56 (1H, s).

MS (ESI) m/z: 464 [M+H]$^+$.

Example 29

2,6-Difluoro-4-{[(1S*,2R*)-2-(1H-pyrazol-4-yl)cyclohexyl]oxy}-N-(pyrimidin-4-yl)benzenesulfonamide

[Formula 51]

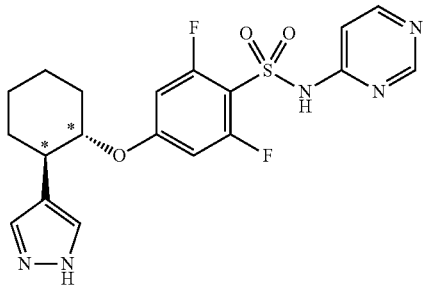

(29a) 4-(Cyclohex-1-en-1-yl)-1-(tetrahydro-2H-pyran-2-yl)-1H-pyrazole

The reaction and aftertreatment were conducted in the same manner as in Example 22b by using 4-iodo-1-(tetrahydro-2H-pyran-2-yl)-1H-pyrazole (J. Org. Chem. 2007, 72, 3589-3591; 2.00 g, 7.19 mmol), 2-(cyclohex-1-en-1-yl)-4,4,5,5-tetramethyl-1,3,2-dioxaborolane (1.50 g, 7.21 mmol), [1,1'-bis(diphenylphosphino)ferrocene]dichloropalladium (II) (300 mg, 0.41 mmol), potassium carbonate (3.00 g, 21.7 mmol), and DMF (13 mL), to yield the title compound (637 mg, 38%) as a colorless oil.

$^1$H-NMR (500 MHz, CDCl$_3$) δ ppm: 1.58-1.76 (8H, m), 2.03-2.05 (2H, m), 2.08-2.16 (2H, m), 16.28 (2H, m), 3.69 (1H, dt, J=2.4, 11.2 Hz), 4.04-4.07 (1H, m), 5.34 (1H, dd, J=2.4, 9.8 Hz), 6.00-6.02 (1H, m), 6.96 (1H, brs), 7.52 (1H, s), 7.61 (1H, s).

(29b) (1S*,2R*)-2-[1-(Tetrahydro-2H-pyran-2-yl)-1H-pyrazol-4-yl]cyclohexanol To a solution of the 4-(cyclohex-1-en-1-yl)-1-(tetrahydro-2H-pyran-2-yl)-1H-pyrazole (775 mg, 3.34 mmol) prepared in Example 29a in THF (4 mL), a borane-THF complex (0.95 M solution in THF; 3.4 mL, 3.23 mmol) was added with cooling on ice, and the reaction solution was stirred for 30 minutes with cooling on ice. A borane-THF complex (0.95 M solution in THF; 3.4 mL, 3.23 mmol) was added again to the reaction solution, and the mixture was stirred at room temperature for 90 minutes. Water (5 mL) and subsequently sodium perborate tetrahydrate (1.00 g, 6.50 mmol) were added to the reaction solution, and the mixture was stirred for 5 hours. Sodium thiosulfate (2.0 g) was added to the reaction solution, followed by extraction with ethyl acetate (50 mL). The thus obtained organic layer was dried over anhydrous sodium sulfate. After concentration under reduced pressure, the residue was purified with column chromatography (dichloromethane/methanol=97:3) to yield the title compound (590 mg, 71%) as a colorless oil.

$^1$H-NMR (400 MHz, CDCl$_3$) δ ppm: 1.24-1.94 (10H, m), 2.05-2.14 (4H, m), 2.37-2.43 (1H, m), 3.38-3.44 (1H, m), 3.67-3.73 (1H, m), 4.07 (1H, dd, J=3.9, 11.7 Hz), 5.34 (1H, dd, J=2.7, 9.8 Hz), 7.49 (1H, s), 7.50 (1H, s).

(29c) N-(2,4-Dimethoxybenzyl)-2,6-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (0.20 g, 0.45 mmol) prepared in Example 4a, the (1S*,2R*)-2-[1-(tetrahydro-2H-pyran-2-yl)-1H-pyrazol-4-yl]cyclohexanol (0.10 g, 0.40 mmol) prepared in Example 29b, sodium hydride (63%; 27 mg, 0.68 mmol), DMF (6.0 mL) and water (0.008 mL), to yield the title compound (100 mg, 33%) as a colorless solid.

$^1$H-NMR (500 MHz, CDCl$_3$) δ ppm: 1.36-1.67 (8H, m), 1.80-2.17 (6H, m), 2.77-2.82 (1H, m), 3.62-3.67 (1H, m), 3.77 (3H, s), 3.82 (3H, s), 3.97-4.02 (2H, m), 5.26 (2H, s), 5.25-5.28 (1H, m), 6.37 (2H, dd, J=2.0, 11.2 Hz), 6.41 (1H, dd, J=2.4, 8.3 Hz), 6.44 (1H, d, J=2.4 Hz), 7.18 (1H, dt, J=1.5, 6.4 Hz), 7.21 (1H, d, J=8.3 Hz), 7.39 (2H, d, J=11.7 Hz), 8.44 (1H, d, J=6.4 Hz), 8.78 (1H, s).

(29d) 2,6-Difluoro-4-{[(1S*,2R*)-2-(1H-pyrazol-4-yl)cyclohexyl]oxy}-N-(pyrimidin-4-yl)benzenesulfonamide To a solution of the N-(2,4-dimethoxybenzyl)-2,6-difluoro-N-(pyrimidin-4-yl)-4-({(1S*,2R*)-2-[1-(tetrahydro-2H-pyran-2-yl)-1H-pyrazol-4-yl]cyclohexyl}oxy)benzenesulfonamide (100 mg, 0.171 mmol) prepared in Example 29c and triethylsilane (0.10 mL) in dichloromethane (1.0 mL), trifluoroacetic acid (1.0 mL) was added at room temperature, and the reaction solution was stirred for 1 hour. Methanol (1.0 mL) was added to the reaction solution, and the mixture was further stirred at room temperature for 1 hour. The reaction solution was concentrated, and the residue was purified with silica gel chromatography (dichloromethane/methanol=95:5) to yield the title compound (40 mg, 54%) as a colorless solid.

$^1$H-NMR (500 MHz, DMSO-d$_6$) δ ppm: 1.24-1.36 (2H, m), 1.44-1.59 (2H, m), 1.68-1.75 (2H, m), 1.92-1.95 (1H, m), 2.07-2.09 (1H, m), 2.68-2.74 (1H, m), 4.36 (1H, dt, J=3.9, 10.3 Hz), 6.78 (2H, d, J=11.7 Hz), 6.95 (1H, brs), 7.42 (2H, s), 8.29 (1H, brs), 8.58 (1H, s).

MS (ESI) m/z: 436[M+H]$^+$

Example 30

4-{[(1S,2R)-5,5-Difluoro-2-(1-methyl-1H-pyrazol-5-yl)cyclohexyl]oxy}-2,5-difluoro-N-(pyrimidin-4-yl)benzenesulfonamide

[Formula 52]

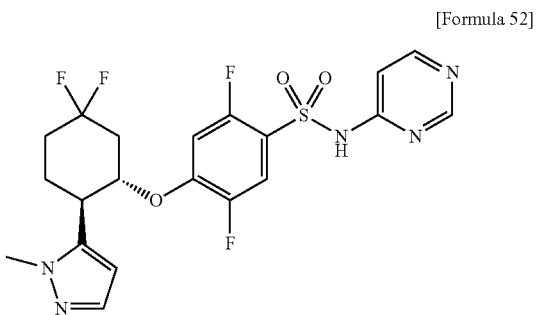 [SMILES: Cn1nccc1[C@H]1CCC(F)(F)C[C@@H]1Oc1cc(F)c(S(=O)(=O)Nc2ccncn2)cc1F]

(30a) (1S,2R)-4,4-Difluoro-1-(1-methyl-1H-pyrazol-5-yl)cyclohexane-1,2-diol

To a solution of methanesulfonamide (480 mg, 5.05 mmol) in a mixed solvent of t-butanol (10 mL) and water (10 mL), AD-mixα (Sigma-Aldrich Corp.; 7.10 g) was added, and the reaction solution was stirred at room temperature for 10 minutes. To the reaction solution, a solution of the 5-(4,4-difluorocyclohex-1-en-1-yl)-1-methyl-1H-pyrazole (1.0 g, 5.05 mmol) prepared in Example 12a in t-butanol (5 mL) was added with cooling on ice, and the reaction solution was vigorously stirred at room temperature for 16 hours. To the reaction solution, an aqueous sodium sulfite solution (10 mL) was added, followed by extraction with ethyl acetate (50 mL). The thus obtained organic layer was dried over anhydrous sodium sulfate to yield the title compound in a crude form.

(30b) 5-[(1S,6S)-4,4-Difluoro-7-oxabicyclo[4.1.0]hept-1-yl]-1-methyl-1H-pyrazole A solution of the crude (1S,2R)-4,4-difluoro-1-(1-methyl-1H-pyrazol-5-yl)cyclohexane-1,2-diol prepared in Example 30a, trimethyl orthoacetate (1.60 mL, 12.6 mmol) and p-toluenesulfonic acid (48 mg, 0.25 mmol) in dichloromethane (25 mL) was stirred for 45 hours. The reaction solution was concentrated and diluted with acetonitrile (15 mL). Lithium bromide (220 mg, 2.53 mmol) and acetyl bromide (0.93 mL, 12.6 mmol) were added thereto with cooling on ice, and the reaction solution was stirred for 6 hours with cooling on ice. The reaction solution was concentrated and then diluted with methanol (20 mL). Potassium carbonate (1.75 g, 12.7 mmol) was added thereto, and the reaction solution was stirred at room temperature for 2 hours. To the reaction solution, water (50 mL) was added, followed by extraction with ethyl acetate (100 mL). The thus obtained organic layer was dried over anhydrous sodium sulfate. After concentration under reduced pressure, the residue was purified with silica gel chromatography to yield the title compound (752 mg, 70%, 2 steps) as a colorless solid.

(30c) (1S,2R)-5,5-Difluoro-2-(1-methyl-1H-pyrazol-5-yl)cyclohexanol

A solution of the 5-[(1S,6S)-4,4-difluoro-7-oxabicyclo[4.1.0]hept-1-yl]-1-methyl-1H-pyrazole (50 mg, 0.233 mmol) prepared in Example 30b and Raney nickel (500 mg) in isopropanol (20 mL) was stirred for 3 hours under a hydrogen atmosphere. The reaction solution was filtered, the filtrate was concentrated, and the residue was then purified with silica gel chromatography to yield the title compound (21.2 mg, 42%) as a colorless oil.

(30d) 4-{[(1S,2R)-5,5-Difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (145 mg, 0.33 mmol) prepared in Example 1b, the (1S,2R)-5,5-difluoro-2-(1-methyl-1H-pyrazol-5-yl)cyclohexanol (50 mg, 0.23 mmol) prepared in Example 30c, sodium hydride (63%; 12 mg, 0.33 mmol), DMF (1.6 mL) and water (0.006 mL), to yield the title compound (130 mg, 62%) as a colorless oil.

(30e) 4-{[(1S,2R)-5,5-Difluoro-2-(1-methyl-1H-pyrazol-5-yl)cyclohexyl]oxy}-2,5-difluoro-N-(pyrimidin-4-yl)benzenesulfonamide The reaction and aftertreatment were conducted in the same manner as in Example 1e by using the 4-{[(1S,2R)-5,5-difluoro-2-(1-methyl-1H-pyrazol-5-yl)cyclohexyl]oxy}-N-(2,4-dimethoxybenzyl)-2,5-difluoro-N-(pyrimidin-4-yl)benzenesulfonamide (130 mg, 0.20 mmol) prepared in Example 30d, triethylsilane (0.30 mL), trifluoroacetic acid (3.0 mL) and dichloromethane (3.0 mL), to yield the title compound (70 mg, 99%) as a colorless solid.

$[\alpha]_D^{25} = -7.62$ (c 1.03, DMSO).

Example 31

4-{[(1S*,2R*)-4,4-Difluoro-2-(1-methyl-1H-pyrazol-5-yl)cyclopentyl]oxy}-2,5-difluoro-N-(pyrimidin-4-yl)benzenesulfonamide

[Formula 53]

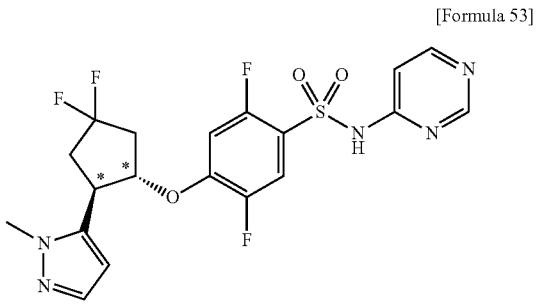 [SMILES: Cn1nccc1[C@H]1CC(F)(F)C[C@@H]1Oc1cc(F)c(S(=O)(=O)Nc2ccncn2)cc1F]

(31a) (1S*,2R*,4S*)-4-(Benzyloxy)-2-(1-methyl-1H-pyrazol-5-yl)cyclopentanol

The reaction and aftertreatment were conducted in the same manner as in Example 3a by using 1-methylpyrazole (3.40 g, 41.4 mmol), n-butyl lithium (2.69 M solution in hexane; 15.4 mL, 41.4 mmol), (1R*,3R*,5S*)-3-benzyloxy-6-oxabicyclo[3.1.0]hexane (Tetrahedron, 2002, 58, 4675-4689; 7.77 g, 40.8 mmol), and THF (120 mL), to yield the title compound (2.58 g, 23%) as a brown oil.

$^{1}$H-NMR (500 MHz, CDCl$_3$) δ ppm: 1.83-1.89 (1H, m), 2.01-2.05 (1H, m), 2.14-2.19 (1H, m), 2.46-2.50 (1H, m), 2.73 (1H, d, J=8.3 Hz), 3.38-3.42 (1H, m), 3.89 (3H, s), 4.11-4.15 (1H, m), 4.19-4.21 (1H, m), 4.54 (2H, s), 5.94 (1H, d, J=2.0 Hz), 7.29-7.41 (6H, m).

(31b) (1S*,2R*,4S*)-4-(Benzyloxy)-2-(1-methyl-1H-pyrazol-5-yl)cyclopentyl benzoate To a solution of the (1S*,2R*,4S*)-4-(benzyloxy)-2-(1-methyl-1H-pyrazol-5-yl)cyclopentanol (234 mg, 0.859 mmol) prepared in Example 31a and triethylamine (0.40 mL, 2.87 mmol) in dichloromethane (4.0 mL), benzoyl chloride (0.260 mL, 2.24 mmol) was added, and the reaction solution was stirred for 5 hours. To the reaction solution, water (50 mL) was added, and an organic layer was extracted. The thus obtained organic layer was dried over anhydrous sodium sulfate. After concentration under reduced pressure, the residue was purified with column chromatography (hexane/ethyl acetate=3:2) to yield the title compound (297 mg, 92%) as a colorless oil.

¹H-NMR (500 MHz, CDCl₃) δ ppm: 1.97-2.08 (2H, m), 2.41-2.46 (1H, m), 2.619 (1H, m), 3.72-3.77 (1H, m), 3.89 (3H, s), 4.125 (1H, m), 4.51 (1H, d, J=11.7 Hz), 4.56 (1H, d, J=11.7 Hz), 5.33 (1H, dt, J=4.9, 7.3 Hz), 6.06 (1H, d, J=1.5 Hz), 7.28-7.44 (8H, m), 7.54-7.58 (1H, m), 8.02 (2H, d, J=8.3 Hz).

(31c) (1S*,2R*,4S*)-4-Hydroxy-2-(1-methyl-1H-pyrazol-5-yl)cyclopentyl benzoate

A solution of the (1S*,2R*,4S*)-4-(benzyloxy)-2-(1-methyl-1H-pyrazol-5-yl)cyclopentyl benzoate (297 mg, 0.789 mmol) prepared in Example 31b and palladium carbon (5%; 300 mg) in ethanol (3.0 mL) was stirred under a hydrogen atmosphere for 8 hours. The reaction solution was filtered through Celite and concentrated to yield the title compound (205 mg, 91%) as a colorless oil.

¹H-NMR (500 MHz, CDCl₃) δ ppm: 1.88-1.92 (1H, m), 2.03-2.09 (1H, m), 2.28-2.33 (1H, m), 2.66-2.71 (1H, m), 3.79-3.84 (1H, m), 3.91 (3H, s), 4.58-4.60 (1H, m), 5.31-5.35 (1H, m), 6.06 (1H, d, J=2.0 Hz), 7.39 (1H, d, J=2.0 Hz), 7.43-7.46 (2H, m), 7.56-7.59 (1H, m), 8.01-8.03 (2H, m).

(31d) (1S*,2R*)-2-(1-Methyl-1H-pyrazol-5-yl)-4-oxocyclopentyl benzoate

To a solution of the (1S*,2R*,4S*)-4-hydroxy-2-(1-methyl-1H-pyrazol-5-yl)cyclopentyl benzoate (205 mg, 0.716 mmol) prepared in Example 31c in dichloromethane (3.0 mL), Dess-Martin reagent (610 mg, 1.44 mmol) was added, and the reaction solution was stirred for 2 hours. To the reaction solution, an aqueous sodium hydrogencarbonate solution (10 mL) was added, and an organic layer was extracted with dichloromethane (10 mL). The thus obtained organic layer was dried over anhydrous sodium sulfate. After concentration under reduced pressure, the residue was purified with silica gel chromatography (hexane/ethyl acetate=2:3) to yield the title compound (140 mg, 69%) as a colorless oil.

¹H-NMR (500 MHz, CDCl₃) δ ppm: 2.47-2.59 (2H, m), 2.81-2.98 (2H, m), 3.88-3.89 (1H, m), 4.09 (3H, s), 5.57-5.59 (1H, m), 6.03 (1H, d, J=2.0 Hz), 7.43-7.49 (3H, m), 7.60-7.63 (1H, m), 8.02-8.04 (2H, m).

(31e) (1S*,2R*)-4,4-Difluoro-2-(1-methyl-1H-pyrazol-5-yl)cyclopentyl benzoate

To a solution of the (1S*,2R*)-2-(1-methyl-1H-pyrazol-5-yl)-4-oxocyclopentyl benzoate (140 mg, 0.716 mmol) prepared in Example 31d in dichloromethane (3.0 mL), bis(2-methoxyethyl)amino sulfur trifluoride (0.80 mL, 4.10 mmol) was added with cooling on ice, and the reaction solution was stirred at room temperature for 4 hours. To the reaction solution, an aqueous sodium hydrogencarbonate solution (10 mL) was added, and an organic layer was extracted. The thus obtained organic layer was dried over anhydrous sodium sulfate. After concentration under reduced pressure, the residue was purified with silica gel chromatography (hexane/ethyl acetate=1:1) to yield the title compound (90 mg, 60%) as a colorless oil.

¹H-NMR (500 MHz, CDCl₃) δ ppm: 2.35-2.47 (2H, m), 2.76-2.93 (2H, m), 3.68-3.72 (1H, m), 3.97 (3H, s), 5.38-5.41 (1H, m), 6.19 (1H, d, J=2.0 Hz), 7.43-7.48 (3H, m), 7.58-7.62 (1H, m), 8.01-8.03 (2H, m).

(31f) (1S*,2R*)-4,4-Difluoro-2-(1-methyl-1H-pyrazol-5-yl)cyclopentanol

To a solution of the (1S*,2R*)-4,4-difluoro-2-(1-methyl-1H-pyrazol-5-yl)cyclopentyl benzoate (90 mg, 0.294 mmol) prepared in Example 31e in methanol (3.0 mL), potassium carbonate (60 mg, 0.434 mmol) was added, and the reaction solution was stirred for 30 minutes. To the reaction solution, water (10 mL) was added, and an organic layer was extracted with ethyl acetate (20 mL). The thus obtained organic layer was dried over anhydrous sodium sulfate. After concentration under reduced pressure, the residue was purified with silica gel chromatography (dichloromethane/methanol=96:4) to yield the title compound (48 mg, 81%) as a colorless oil.

¹H-NMR (500 MHz, CDCl₃) δ ppm: 2.14-2.38 (2H, m), 2.60-2.71 (2H, m), 3.24-3.30 (1H, m), 3.68 (1H, brs), 3.79 (3H, s), 4.26-4.31 (1H, m), 6.08 (1H, d, J=1.5 Hz), 7.33 (1H, d, J=1.5 Hz).

(31g) 4-{[(1S*,2R*)-4,4-Difluoro-2-(1-methyl-1H-pyrazol-5-yl)cyclopentyl]oxy}-N-(2,4-dimethoxybenzyl)-2,5-difluoro-N-(pyrimidin-4-yl)benzenesulfonamide The reaction and aftertreatment were conducted in the same manner as in Example 1d by using the N-(2,4-dimethoxybenzyl)-2,4,5-trifluoro-N-(pyrimidin-4-yl)benzenesulfonamide (105 mg, 0.239 mmol) prepared in Example 1b, the (1S*,2R*)-4,4-difluoro-2-(1-methyl-1H-pyrazol-5-yl)cyclopentanol (48 mg, 0.237 mmol) prepared in Example 31f, sodium hydride (63%; 30 mg, 0.788 mmol) and DMF (2.0 mL), to yield the title compound (118 mg, 79%) as a colorless oil.

¹H-NMR (500 MHz, CDCl₃) δ ppm: 2.33-2.45 (2H, m), 2.74-2.92 (2H, m), 3.75-3.80 (1H, m), 3.77 (3H, s), 3.79 (3H, s), 3.90 (3H, s), 4.67 (1H, q, J=6.8 Hz), 5.20 (1H, d, J=16.6 Hz), 5.24 (1H, d, J=16.6 Hz), 6.14 (1H, d, J=2.0 Hz), 6.39-6.47 (3H, m), 7.15 (1H, dd, J=1.5, 5.9 Hz), 7.19 (1H, d, J=8.3 Hz), 7.43 (1H, d, J=2.0 Hz), 7.79 (1H, dd, J=6.8, 10.3 Hz), 8.46 (1H, d, J=5.9 Hz), 8.78 (1H, d, J=1.0 Hz).

(31h) 4-{[(1S*,2R*)-4,4-Difluoro-2-(1-methyl-1H-pyrazol-5-yl)cyclopentyl]oxy}-2,5-difluoro-N-(pyrimidin-4-yl)benzenesulfonamide The reaction and aftertreatment were conducted in the same manner as in Example 1e by using the 4-{[(1S*,2R*)-4,4-difluoro-2-(1-methyl-1H-pyrazol-5-yl)cyclopentyl]oxy}-N-(2,4-dimethoxybenzyl)-2,5-difluoro-N-(pyrimidin-4-yl)benzenesulfonamide (118 mg, 0.190 mmol) prepared in Example 31g, triethylsilane (0.20 mL), trifluoroacetic acid (2.0 mL) and dichloromethane (2.0 mL), to yield the title compound (50 mg, 56%) as a colorless solid.

¹H-NMR (500 MHz, DMSO-d₆) δ ppm: 2.29-2.43 (2H, m), 2.73-2.80 (1H, m), 2.99-3.01 (1H, m), 3.79-3.84 (1H, m), 3.79 (3H, s), 5.04-5.08 (1H, m), 6.29 (1H, s), 6.98 (1H, brs), 7.20-7.23 (1H, m), 7.33 (1H, s), 7.71 (1H, brs), 8.21 (1H, brs), 8.57 (1H, s).

MS (ESI) m/z: 472 [M+H]⁺.

Example 32

4-{[(1S*,2R*)-5,5-Difluoro-2-(1-methyl-1H-pyrazol-5-yl)cyclohexyl]oxy}-2,6-difluoro-N-(pyrimidin-4-yl)benzenesulfonamide

[Formula 54]

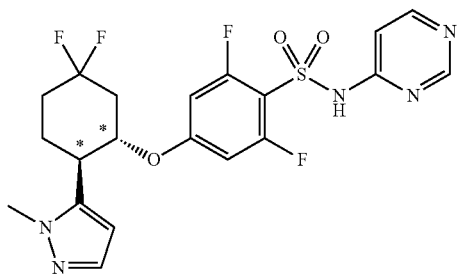

(32a) 4-{[(1S*,2R*)-5,5-Difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (243 mg, 0.55 mmol) prepared in Example 4a, the (1S*,2R*)-5,5-difluoro-2-(1-methyl-1H-pyrazol-5-yl)cyclohexanol (100 mg, 0.46 mmol) prepared in Example 12b, sodium hydride (63%; 27 mg, 0.69 mmol), DMF (4.0 mL) and water (0.008 mL), to yield the title compound (140 mg, 48%) as a colorless amorphous solid.

$^1$H-NMR (500 MHz, CDCl$_3$) δ ppm: 1.90-2.11 (4H, m), 2.29-2.33 (1H, m), 55.74 (1H, m), 3.00-3.05 (1H, m), 3.77 (3H, s), 3.81 (3H, s), 3.87 (3H, s), 4.36 (1H, dt, J=4.4, 10.7 Hz), 5.24 (2H, s), 6.05 (1H, d, J=2.0 Hz), 6.30 (2H, d, J=10.7 Hz), 6.40-6.44 (2H, m), 7.13 (1H, dd, J=1.5, 5.9 Hz), 7.21 (1H, d, J=8.3 Hz), 7.37 (1H, d, J=2.0 Hz), 8.45 (1H, d, J=5.8 Hz), 8.78 (1H, d, J=1.0 Hz).

(32b) 4-{[(1S*,2R*)-5,5-Difluoro-2-(1-methyl-1H-pyrazol-5-yl)cyclohexyl]oxy}-2,6-difluoro-N-(pyrimidin-4-yl)benzenesulfonamide The reaction and aftertreatment were conducted in the same manner as in Example 1e by using the 4-{[(1S*,2R*)-5,5-difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide (120 mg, 0.188 mmol) prepared in Example 32a, triethylsilane (0.15 mL), trifluoroacetic acid (1.5 mL) and dichloromethane (1.5 mL), to yield the title compound (45 mg, 49%) as a colorless solid.

$^1$H-NMR (500 MHz, DMSO-d$_6$) δ ppm: 1.24-1.29 (1H, m), 1.67-1.76 (1H, m), 1.91-2.22 (3H, m), 2.64-2.66 (1H, m), 3.27-3.33 (1H, m), 3.77 (3H, s), 4.70 (1H, dt, J=4.4, 10.3 Hz), 6.19 (1H, d, J=2.0 Hz), 6.70-6.73 (2H, m), 6.91 (1H, brs), 7.20 (1H, d, J=2.0 Hz), 8.27 (1H, brs), 8.57 (1H, s).

MS (ESI) m/z: 486 [M+H]$^+$.

Example 33

4-{[(1S,2R)-2-(1-Ethyl-1H-pyrazol-5-yl)cyclopentyl]oxy}-2,3-difluoro-N-(pyrimidin-4-yl)benzenesulfonamide

[Formula 55]

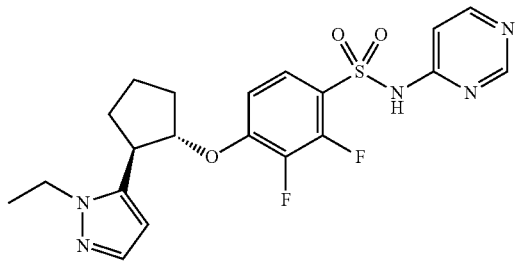

(33a) (1S,2R)-2-(1-Ethyl-1H-pyrazol-5-yl)cyclopentanol

The (1S*,2R*)-2-(1-ethyl-1H-pyrazol-5-yl)cyclopentanol prepared in Example 8b was optically resolved with CHIRALPAK AD-H (Daicel Corp.; hexane/ethanol=8:2) to yield the title compound as a colorless oil.

$[\alpha]_D^{25}$=56.1 (c 1.00, MeOH).

(33b) N-(2,4-Dimethoxybenzyl)-4-{[(1S,2R)-2-(1-ethyl-1H-pyrazol-5-yl)cyclopentyl]oxy}-2,3-difluoro-N-(pyrimidin-4-yl)benzenesulfonamide The reaction and aftertreatment were conducted in the same manner as in Example 1d by using the N-(2,4-dimethoxybenzyl)-2,3,4-trifluoro-N-(pyrimidin-4-yl)benzenesulfonamide (99.1 g, 226 mmol) prepared in Example 8a, the (1S,2R)-2-(1-ethyl-1H-pyrazol-5-yl)cyclopentanol (40.7 g, 226 mol) prepared in Example 33a, sodium hydride (63%; 12.9 g, 339 mmol) and DMF (1.2 L), to yield the title compound (100.3 g, 74%) as a colorless oil.

(33c) 4-{[(1S,2R)-2-(1-Ethyl-1H-pyrazol-5-yl)cyclopentyl]oxy}-2,3-difluoro-N-(pyrimidin-4-yl)benzenesulfonamide The N-(2,4-dimethoxybenzyl)-4-{[(1S,2R)-2-(1-ethyl-1H-pyrazol-5-yl)cyclopentyl]oxy}-2,3-difluoro-N-(pyrimidin-4-yl)benzenesulfonamide (100.3 g, 167 mmol) prepared in Example 33b and triethylsilane (30 mL) in dichloromethane (300 mL), trifluoroacetic acid (300 mL) was added at room temperature, the reaction solution was stirred for 1 hour. The reaction solution was concentrated, and the residue was purified with silica gel chromatography (ethyl acetate/methanol=9:1). The purified compound was further washed with ethyl acetate to yield the title compound (44.5 g, 59%) as a colorless solid.

$^1$H-NMR (500 MHz, DMSO-d$_6$) δ ppm: 1.25 (3H, t, J=7.0 Hz), 1.64-1.91 (4H, m), 2.19-2.32 (2H, m), 3.47-3.50 (1H, m), 4.09 (2H, q, J=7.0 Hz), 4.92-4.96 (1H, m), 6.17 (1H, d, J=1.5 Hz), 6.97 (1H, brs), 7.07 (1H, t, J=7.7 Hz), 7.34 (1H, d, J=1.5 Hz), 7.60-7.64 (1H, m), 8.23 (1H, brs), 8.55 (1H, s), 13.2 (1H, brs).

MS (ESI) m/z: 450 [M+H]$^+$.

$[\alpha]_D^{25}$=50.4 (c 1.05, DMSO).

Example 34

5-Chloro-2-fluoro-4-{[(1S,2R)-2-(1-methyl-1H-pyrazol-5-yl)cyclohexyl]oxy}-N-(pyrimidin-4-yl)benzenesulfonamide

[Formula 56]

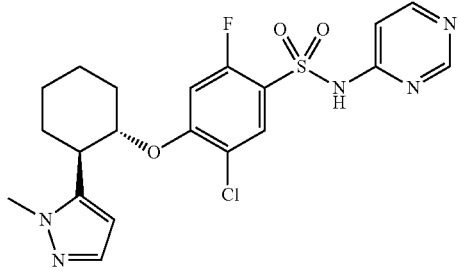

(34a) (1S,2R)-2-(1-Methyl-1H-pyrazol-5-yl)cyclohexanol

The (1S*,2R*)-2-(1-methyl-1H-pyrazol-5-yl)cyclohexanol prepared in Example 3a was optically resolved with CHIRALPAK IB (Daicel Corp.; hexane/ethanol=9:1) to yield the title compound as a colorless oil.

$[\alpha]_D^{25}$=33.3 (c 0.916, MeOH).

(34b) 5-Chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide The reaction and aftertreatment were conducted in the same manner as in Example 1a by using the 5-chloro-N-(2,4-dimethoxybenzyl)-2,4-difluoro-N-(pyrimidin-4-yl)benzenesulfonamide (0.60 g, 1.32 mmol) prepared in Example 2a, the (1S,2R)-2-(1-methyl-1H-pyrazol-5-yl)cyclohexanol (0.19 g, 1.05 mmol) prepared in Example 34a, sodium hydride (63%; 0.050 g, 1.32 mmol), DMF (6.6 mL) and water (0.020 mL), to yield the title compound (0.371 g, 50%) as a colorless solid.

(34c) 5-Chloro-2-fluoro-4-{[(1S,2R)-2-(1-methyl-1H-pyrazol-5-yl)cyclohexyl]oxy}-N-(pyrimidin-4-yl)benzenesulfonamide To a solution of the 5-chloro-N-(2,4-dimethoxybenzyl)-2-fluoro-4-{[(1S,2R)-2-(1-methyl-1H-pyrazol-5-yl)cyclohexyl]oxy}-N-(pyrimidin-4-yl)benzenesulfonamide (0.371 g, 0.602 mmol) prepared in Example 34b and triethylsilane (0.48 mL, 3.01 mmol) in dichloromethane (6.0 mL), trifluoroacetic acid (0.60 mL) was added at room temperature, and the reaction solution was stirred for 1 hour. The reaction solution was concentrated, and the residue was purified with silica gel chromatography (ethyl acetate/methanol=6:1) to yield the title compound (0.28 g, 99%) as a colorless solid.

$[\alpha]_D^{25}$=2.28 (c 1.05, DMSO).

Example 35

(1S,2R)-2-(1-Methyl-1H-pyrazol-5-yl)cyclohexanol

[Formula 57]

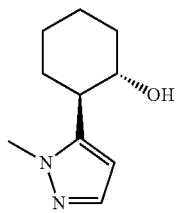

(35a) 1-(1-Methyl-1H-pyrazol-5-yl)cyclohexanol

To a solution of 1-methylpyrazole (6.0 g, 73.1 mmol) and N,N,N',N'-tetramethylethylenediamine (10.96 mL, 73.1 mmol) in THF (125 mL), butyl lithium (2.69 M solution in hexane; 31.8 mL, 85.5 mmol) was added at −78° C. The reaction solution was stirred at −78° C. for 30 minutes. Then, cyclohexanone (9.06 mL, 87.7 mmol) was added thereto, and the mixture was stirred at room temperature for 15 hours. To the reaction solution, water (500 mL) was added, followed by extraction with ethyl acetate (250 mL). The thus obtained organic layer was dried over anhydrous sodium sulfate. After concentration under reduced pressure, the residue was purified with silica gel chromatography (hexane/ethyl acetate=3:2) to yield the title compound (11.32 g, 86%) as a colorless oil.

$^1$H-NMR (500 MHz, CDCl$_3$) δ ppm: 1.60-1.84 (8H, m), 1.99-2.01 (2H, m), 4.05 (3H, s), 6.08 (1H, d, J=2.0 Hz), 7.32 (1H, d, J=1.5 Hz).

(35b) 5-(Cyclohex-1-en-1-yl)-1-methyl-1H-pyrazole

A solution of the 1-(1-methyl-1H-pyrazol-5-yl)cyclohexanol (11.32 g, 62.8 mmol) prepared in Example 35a and p-toluenesulfonic acid monohydrate (17.9 g, 94.1 mmol) in toluene (100 mL) was heated under reflux with stirring for 8 hours, and the solvent was subjected to azeotropic distillation with water. After allowing to cool, water (100 mL) was added to the reaction solution, and an organic layer was extracted. The thus obtained organic layer was dried over anhydrous sodium sulfate. After concentration under reduced pressure, the residue was purified with silica gel chromatography (hexane/ethyl acetate=3:1) to yield the title compound (8.89 g, 87%) as a colorless oil.

$^1$H-NMR (500 MHz, CDCl$_3$) δ ppm: 1.66-1.78 (4H, m), 2.19-2.28 (4H, m), 3.85 (3H, s), 5.86-5.88 (1H, m), 6.08 (1H, d, J=1.5 Hz), 7.40 (1H, d, J=2.0 Hz).

(35c) (1S,2S)-1-(1-Methyl-1H-pyrazol-5-yl)cyclohexane-1,2-diol

The reaction and aftertreatment were conducted in the same manner as in Example 30a by using the 5-(cyclohex-1-en-1-yl)-1-methyl-1H-pyrazole (2.66 g, 16.4 mmol) prepared in Example 35b, methanesulfonamide (1.56 g, 16.4 mmol), t-butanol (20 mL), water (20 mL) and AD-mixα (Sigma-Aldrich Corp.; 23.0 g), to yield the title compound (3.22 g, 99%) as a colorless solid.

¹H-NMR (400 MHz, CDCl₃) δ ppm: 1.29-1.89 (6H, m), 2.09-2.09 (1H, m), 2.16-2.22 (1H, m), 4.05-4.10 (1H, m), 4.07 (3H, s), 4.80 (1H, brs), 6.08 (1H, d, J=2.0 Hz), 7.39 (1H, d, J=2.0 Hz).

(35d) 1-Methyl-5-[(1S,6S)-7-oxabicyclo[4.1.0]hept-1-yl]-1H-pyrazole

The reaction and aftertreatment were conducted in the same manner as in Example 30b by using the (1S,2S)-1-(1-methyl-1H-pyrazol-5-yl)cyclohexane-1,2-diol (423 mg, 2.15 mmol) prepared in Example 35c, trimethyl orthoacetate (0.688 mL, 5.38 mmol), p-toluenesulfonic acid (20.5 mg, 0.11 mmol), dichloromethane (6.0 mL), acetonitrile (6.0 mL), lithium bromide (466 mg, 5.38 mmol), acetyl bromide (0.398 mL, 5.38 mmol), methanol (6.0 mL) and potassium carbonate (743 mg, 5.38 mmol), to yield the title compound (180 mg, 47%).

¹H-NMR (400 MHz, CDCl₃) δ ppm: 1.29-1.61 (4H, m), 1.96-2.24 (1H, m), 3.27-3.29 (1H, m), 3.92 (3H, s), 4.80 (1H, brs), 6.13 (1H, d, J=1.6 Hz), 7.36 (1H, d, J=1.6 Hz).

(35e) (1S,2R)-2-(1-Methyl-1H-pyrazol-5-yl)cyclohexanol

The reaction and aftertreatment were conducted in the same manner as in Example 30c by using the 1-methyl-5-[(1S,6S)-7-oxabicyclo[4.1.0]hept-1-yl]-1H-pyrazole (0.21 g, 1.17 mmol) prepared in Example 35d, Raney nickel (2.0 g) and isopropanol (5.9 mL), to yield the title compound (0.060 g, 28%).

Example 36

2-Fluoro-4-{[(1S,2R)-2-(1-methyl-1H-pyrazol-5-yl)cyclopentyl]oxy}-N-(pyrimidin-4-yl)benzenesulfonamide

[Formula 58]

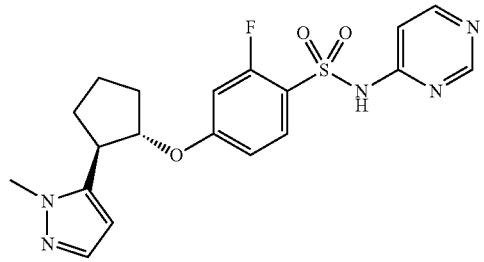

(36a) (1S,2R)-2-(1-Methyl-1H-pyrazol-5-yl)cyclopentanol

The (1S*,2R*)-2-(1-methyl-1H-pyrazol-5-yl)cyclopentanol prepared in Example 1c was optically resolved with CHIRALPAK IC (Daicel Corp.; hexane/ethanol=8:2) to yield the title compound as a colorless oil.

$[\alpha]_D^{25}$=59.0 (c 0.30, MeOH).

(36b) N-(2,4-Dimethoxybenzyl)-2-fluoro-4-{[(1S,2R)-2-(1-methyl-1H-pyrazol-5-yl)cyclopentyl]oxy}-N-(pyrimidin-4-yl)benzenesulfonamide The reaction and aftertreatment were conducted in the same manner as in Example 1d by using the N-(2,4-dimethoxybenzyl)-2,4-difluoro-N-(pyrimidin-4-yl)benzenesulfonamide (191 mg, 0.45 mmol) prepared in Example 6a, the (1S,2R)-2-(1-methyl-1H-pyrazol-5-yl)cyclopentanol (68 mg, 0.38 mmol) prepared in Example 36a, sodium hydride (63%; 28.7 mg, 0.75 mmol) and DMF (2.0 mL), to yield the title compound (198 mg, 93%) as a colorless oil.

(36c) 2-Fluoro-4-{[(1S,2R)-2-(1-methyl-1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2-fluoro-4-{[(1S,2R)-2-(1-methyl-1H-pyrazol-5-yl)cyclopentyl]oxy}-N-(pyrimidin-4-yl)benzenesulfonamide (8.35 g, 14.7 mmol) prepared in Example 36b, triethylsilane (11.75 mL, 73.6 mmol), trifluoroacetic acid (14.7 mL), and dichloromethane (147 mL), to yield the title compound (5.95 g, 97%) as a colorless solid.

$[\alpha]_D^{25}$=59.7 (c 1.01, DMSO).

Example 37

4-{[(1S*,2R*)-4,4-Difluoro-2-(1-methyl-1H-pyrazol-5-yl)cyclohexyl]oxy}-2-fluoro-5-methyl-N-(pyrimidin-4-yl)benzenesulfonamide

[Formula 59]

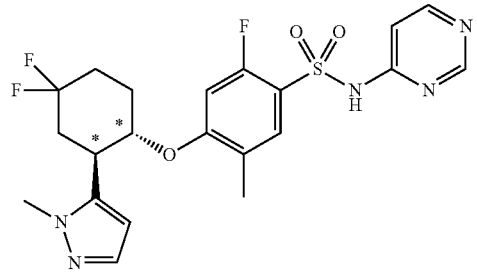

(37a) [(4,4-Difluorocyclohex-1-en-1-yl)oxy](trimethyl)silane

To a solution of N,N-diisopropylamine (3.30 g, 32.6 mmol) in THF (50 mL), n-butyl lithium (1.65 M solution in hexane; 18.0 mL, 29.7 mmol) was added dropwise with cooling on ice. The reaction solution was stirred at 0° C. for 30 minutes. Then, 4,4-difluorocyclohexanone (3.60 g, 26.8 mmol) was added thereto at −78° C., and the reaction solution was stirred at −78° C. for 1 hour. Chlorotrimethylsilane (4.4 mL, 34.8 mmol) and triethylamine (8.0 mL, 57.4 mmol) were added to the reaction solution, and the mixture was stirred at −78° C. for 2 hours. To the reaction solution, a saturated aqueous solution of sodium hydrogencarbonate (20 mL) was added, followed by extraction with ethyl acetate (20 mL). The thus obtained organic layer was dried over anhydrous sodium sulfate. After concentration under reduced pressure, the residue was purified with silica gel chromatography (hexane/ethyl acetate=98:2) to yield the title compound (2.10 g, 56%) as a colorless oil.

¹H-NMR (500 MHz, CDCl₃) δ ppm: 0.20 (9H, s), 2.04-2.12 (2H, m), 16.28 (2H, m), 2.50-2.56 (2H, m), 4.68-4.71 (1H, m).

(37b) 4,4-Difluorocyclohex-2-en-1-one

To a solution of the [(4,4-difluorocyclohex-1-en-1-yl)oxy](trimethyl)silane (3.1 g, 15.0 mmol) prepared in Example 37a in acetonitrile (25 mL), palladium acetate (4.0 g, 17.8 mmol) was added, and the mixture was stirred at room temperature for 45 minutes. The reaction solution was filtered, the filtrate was concentrated under reduced pressure, and the residue was then purified with silica gel chromatography (hexane/ethyl acetate=9:1) to yield the title compound (1.0 g, 50%) as a yellow oil.

$^1$H-NMR (400 MHz, CDCl$_3$) δ ppm: 2.47-2.56 (2H, m), 2.68 (2H, t, J=6.7 Hz), 6.19 (1H, d, J=10.6 Hz), 6.76-6.82 (1H, m).

(37c) 4,4-Difluoro-2-iodocyclohex-2-en-1-one

To the 4,4-difluorocyclohex-2-en-1-one (1.0 g, 7.57 mmol) prepared in Example 37b in a mixed solvent of THF and water (1:1; 20 mL), potassium carbonate (1.30 g, 9.41 mmol), iodine (2.9 g, 11.4 mmol), and DMAP (dimethylaminopyridine; 0.56 g, 4.58 mmol) were added, and the reaction solution was stirred at room temperature for 30 minutes. The reaction solution was subjected to extraction with ethyl acetate (20 mL). The thus obtained organic layer was washed with an aqueous sodium thiosulfate solution (20 mL) and dried over anhydrous sodium sulfate. After concentration under reduced pressure, the residue was purified with silica gel chromatography (hexane/ethyl acetate=9:1) to yield the title compound (1.46 g, 75%) as a light brown oil.

$^1$H-NMR (500 MHz, CDCl$_3$) δ ppm: 2.51-2.59 (2H, m), 2.87 (2H, t, J=6.8 Hz), 7.56-7.58 (1H, m).

(37d) 8,8-Difluoro-6-iodo-1,4-dioxaspiro[4.5]dec-6-ene

The reaction and aftertreatment were conducted in the same manner as in Example 22a by using the 4,4-difluoro-2-iodocyclohex-2-en-1-one (1.46 g, 5.66 mmol) prepared in Example 37c, ethylene glycol (750 mg, 12.1 mmol), p-toluenesulfonic acid hydrate (60 mg, 0.31 mmol), and benzene (30 mL), to yield a mixture of the title compound and a by-product.

(37e) 5-(8,8-Difluoro-1,4-dioxaspiro[4.5]dec-6-en-6-yl)-1-methyl-1H-pyrazole The reaction and aftertreatment were conducted in the same manner as in Example 12a by using the 8,8-difluoro-6-iodo-1,4-dioxaspiro[4.5]dec-6-ene (1.34 g, 4.44 mmol) prepared in Example 37d, 1-methyl-5-(4,4,5,5-tetramethyl-1,3,2-dioxaboran-2-yl)-1H-pyrazole (1.40 g, 6.73 mmol), tetrakis(triphenylphosphine)palladium(0) (250 mg, 0.216 mmol), cesium carbonate (3.40 g, 10.4 mmol), 1,4-dioxane (10 mL), and water (5.0 mL), to yield a mixture of the title compound and a by-product.

(37f) 4,4-Difluoro-2-(1-methyl-1H-pyrazol-5-yl)cyclohex-2-en-1-one

The reaction and aftertreatment were conducted in the same manner as in Example 22c by using the 5-(8,8-difluoro-1,4-dioxaspiro[4.5]dec-6-en-6-yl)-1-methyl-1H-pyrazole (758 mg, 2.96 mmol) prepared in Example 37e, 5 M hydrochloric acid (10 mL), and THF (10 mL), to yield the title compound (170 mg, 14%, 3 steps) as a colorless oil.

$^1$H-NMR (500 MHz, CDCl$_3$) δ ppm: 2.59-2.57 (2H, m), 2.85 (2H, t, J=6.8 Hz), 3.74 (3H, s), 6.29 (1H, d, J=2.0 Hz), 6.84 (1H, t, J=5.9 Hz), 7.48 (1H, d, J=2.0 Hz).

(37g) (1S*,2R*)-4,4-Difluoro-2-(1-methyl-1H-pyrazol-5-yl)cyclohexanol

The reaction and aftertreatment were conducted in the same manner as in Example 22d by using the 4,4-difluoro-2-(1-methyl-1H-pyrazol-5-yl)cyclohex-2-en-1-one (170 mg, 0.80 mmol) prepared in Example 37f, sodium borohydride (60 mg, 1.59 mmol), methanol (3.0 mL), palladium hydroxide carbon (10%; 150 mg), and ethanol (4.0 mL), to yield the title compound (50 mg, 29%) as a colorless solid.

$^1$H-NMR (500 MHz, CDCl$_3$) δ ppm: 1.80-2.00 (3H, m), 2.10-2.13 (1H, m), 12.31 (2H, m), 2.98-3.03 (1H, m), 3.73 (1H, dt, J=4.4, 10.3 Hz), 3.86 (3H, s), 6.08 (1H, d, J=2.0 Hz), 7.41 (1H, d, J=2.0 Hz).

(37h) 4-{[(1S*,2R*)-4,4-Difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (193 mg, 0.44 mmol) prepared in Example 10a, the (1S*,2R*)-4,4-difluoro-2-(1-methyl-1H-pyrazol-5-yl)cyclohexanol (80.0 mg, 0.37 mmol) prepared in Example 37g, sodium hydride (63%; 28.2 mg, 0.74 mmol) and DMF (1.0 mL), to yield the title compound (80.0 mg, 34%) as a colorless solid.

$^1$H-NMR (400 MHz, CDCl$_3$) δ ppm: 1.87-2.48 (6H, m), 2.04 (3H, s), 3.38-3.45 (1H, m), 3.76 (3H, s), 3.78 (3H, s), 3.90 (3H, s), 4.23 (1H, dt, J=3.1, 10.6 Hz), 5.23 (2H, s), 6.03 (1H, d, J=2.0 Hz), 6.34 (1H, d, J=11.7 Hz), 6.38-6.41 (2H, m), 7.19 (1H, d, J=8.6 Hz), 7.24-7.26 (1H, m), 7.38 (1H, d, J=2.0 Hz), 7.69 (1H, d, J=8.2 Hz), 8.43 (1H, d, J=6.3 Hz), 8.76 (1H, d, J=0.8 Hz).

(37i) 4-{[(1S*,2R*)-4,4-Difluoro-2-(1-methyl-1H-pyrazol-5-yl)cyclohexyl]oxy}-2-fluoro-5-methyl-N-(pyrimidin-4-yl)benzenesulfonamide The reaction and aftertreatment were conducted in the same manner as in Example 1e by using the 4-{[(1S*,2R*)-4,4-difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide (80.0 mg, 0.13 mmol) prepared in Example 37h, triethylsilane (0.10 mL), trifluoroacetic acid (1.0 mL) and dichloromethane (1.0 mL), to yield the title compound (61.0 mg, 99%) as a colorless solid.

$^1$H-NMR (400 MHz, CDCl$_3$) δ ppm: 1.83-2.45 (6H, m), 2.06 (3H, s), 3.38-3.45 (1H, m), 3.89 (3H, s), 4.24 (1H, dt, J=3.5, 9.4 Hz), 6.04 (1H, d, J=2.0 Hz), 6.39 (1H, d, J=12.1 Hz), 7.19-7.21 (1H, m), 7.38 (1H, d, J=2.0 Hz), 7.70 (1H, d, J=8.2 Hz), 8.41 (1H, d, J=5.9 Hz), 8.80 (1H, s).

MS (ESI) m/z: 482 [M+H]$^+$.

Example 38

4-{[(1S*,2R*)-5,5-Difluoro-2-(1H-pyrazol-4-yl)cyclohexyl]oxy}-2-fluoro-5-methyl-N-(pyrimidin-4-yl)benzenesulfonamide

[Formula 60]

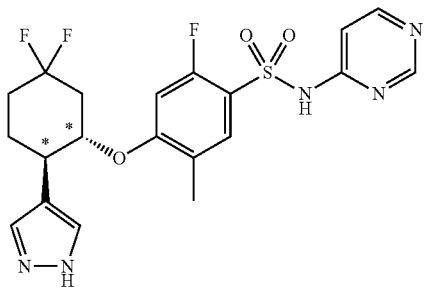

(38a) 4,4-Difluoro-1-[1-(tetrahydro-2H-pyran-2-yl)-1H-pyrazol-4-yl]cyclohexanol The reaction and aftertreatment were conducted in the same manner as in Example 3a by using 4-iodo-1-(tetrahydro-2H-pyran-2-yl)-1H-pyrazole (J. Org. Chem., 2007, 72 (9), 3589-3591; 10.0 g, 35.9 mmol), N,N,N',N'-tetramethylethylenediamine (5.38 mL, 35.9 mmol), t-butyl lithium (1.60 M solution in pentane; 26.2 mL, 43.2 mmol), 4,4-difluorocyclohexanone (4.82 g, 35.9 mmol), and THF (100 mL), to yield the title compound (1.10 g, 11%) as a colorless oil.

$^1$H-NMR (500 MHz, CDCl$_3$) δ ppm: 1.61-1.75 (4H, m), 1.95-2.29 (10H, m), 3.70 (1H, dt, J=2.9, 11.2 Hz), 4.06-4.09 (1H, m), 5.35 (1H, dd, J=3.4, 8.8 Hz), 7.54 (1H, s), 7.59 (1H, s).

(38b) 4-(4,4-Difluorocyclohex-1-en-1-yl)-1-(tetrahydro-2H-pyran-2-yl)-1H-pyrazole A solution of the 4,4-difluoro-1-[1-(tetrahydro-2H-pyran-2-yl)-1H-pyrazol-4-yl]cyclohexanol (1.10 g, 3.84 mmol) prepared in Example 38a and p-toluenesulfonic acid (0.33 g, 1.92 mmol) in toluene (20 mL) was heated under reflux with stirring for 8 hours, and the solvent was subjected to azeotropic distillation with water. After allowing to cool, water (50 mL) was added to the reaction solution, and an organic layer was extracted. The thus obtained organic layer was dried over anhydrous sodium sulfate. After concentration under reduced pressure, the residue was purified with silica gel chromatography to yield the title compound (0.55 g, 70%) as a colorless oil.

$^1$H-NMR (500 MHz, CDCl$_3$) δ ppm: 1.61-1.72 (2H, m), 2.02-2.18 (6H, m), 2.56-2.57 (2H, m), 2.65 (2H, t, J=14.7 Hz), 3.70 (1H, dt, J=2.4, 11.2 Hz), 4.04-4.07 (1H, m), 5.35 (1H, dd, J=2.9, 9.3 Hz), 5.80-5.83 (1H, m), 7.57 (1H, s), 7.61 (1H, s).

(38c) (1S*,2R*)-5,5-Difluoro-2-[1-(tetrahydro-2H-pyran-2-yl)-1H-pyrazol-4-yl]cyclohexanol The reaction and aftertreatment were conducted in the same manner as in Example 29b by using the 4-(4,4-difluorocyclohex-1-en-1-yl)-1-(tetrahydro-2H-pyran-2-yl)-1H-pyrazole (0.54 g, 2.01 mmol) prepared in Example 38b, a borane-THF complex (0.95 M solution in THF; 4.70 mL, 4.42 mmol), sodium perborate tetrahydrate (0.61 g, 4.02 mmol), THF (20 mL), and water (20 mL), to yield the title compound (0.40 g, 70%) as a colorless oil.

$^1$H-NMR (500 MHz, CDCl$_3$) δ ppm: 1.57-2.20 (11H, m), 2.46-2.58 (2H, m), 3.64-3.73 (2H, m), 4.06-4.09 (1H, m), 5.35 (1H, dd, J=2.9, 9.3 Hz), 7.49 (1H, s), 7.53 (1H, s).

(38d) 4-({(1S*,2R*)-5,5-Difluoro-2-[1-(tetrahydro-2H-pyran-2-yl)-1H-pyrazol-4-yl]cyclohexyl}oxy)-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (0.22 g, 0.50 mmol) prepared in Example 10a, the (1S*,2R*)-5,5-difluoro-2-[1-(tetrahydro-2H-pyran-2-yl)-1H-pyrazol-4-yl]cyclohexanol (0.12 g, 0.42 mmol) prepared in Example 38c, sodium hydride (63%; 25 mg, 0.63 mmol), DMF (6.0 mL) and water (0.0075 mL), to yield the title compound (0.22 g, 76%) as a colorless solid.

$^1$H-NMR (500 MHz, CDCl$_3$) δ ppm: 1.58-1.67 (3H, m), 1.88-2.03 (6H, m), 2.15 (3H, s), 2.15-2.17 (1H, m), 2.23-2.27 (1H, m), 2.63-2.68 (1H, m), 2.93-2.98 (1H, m), 3.62-3.67 (1H, m), 3.76 (3H, s), 3.79 (3H, s), 3.97-4.00 (1H, m), 4.21-4.26 (1H, m), 5.25 (2H, s), 5.25-5.29 (1H, m), 6.38-6.41 (3H, m), 7.19 (1H, d, J=8.3 Hz), 7.26-7.27 (1H, m), 7.41-7.42 (2H, m), 7.71 (1H, d, J=8.3 Hz), 8.43 (1H, d, J=5.9 Hz), 8.77 (1H, s).

(38e) 4-{[(1S*,2R*)-5,5-Difluoro-2-(1H-pyrazol-4-yl)cyclohexyl]oxy}-2-fluoro-5-methyl-N-(pyrimidin-4-yl)benzenesulfonamide The reaction and aftertreatment were conducted in the same manner as in Example 29d by using the 4-({(1S*,2R*)-5,5-difluoro-2-[1-(tetrahydro-2H-pyran-2-yl)-1H-pyrazol-4-yl]cyclohexyl}oxy)-N-(2,4-dimethoxybenzyl)-2-fluoro-5-methyl-N-(pyrimidin-4-yl)benzenesulfonamide (0.20 g, 0.28 mmol) prepared in Example 38d, triethylsilane (0.20 mL), trifluoroacetic acid (2.0 mL), dichloromethane (2.0 mL) and methanol (2.0 mL), to yield the title compound (0.11 g, 85%) as a colorless solid.

$^1$H-NMR (500 MHz, DMSO-d$_6$) δ ppm: 1.74-1.83 (1H, m), 1.99-2.18 (4H, m), 2.07 (3H, s), 2.50-2.55 (1H, m), 2.98-3.03 (1H, m), 4.60 (1H, dt, J=4.4, 9.8 Hz), 6.90 (1H, d, J=12.7 Hz), 7.00 (1H, brs), 7.51 (2H, s), 7.64 (1H, d, J=8.8 Hz), 8.31 (1H, brs), 8.58 (1H, s).

MS (ESI) m/z: 468 [M+H]$^+$.

Example 39

4-{[(1S*,2R*)-4,4-Difluoro-2-(1-methyl-1H-pyrazol-5-yl)cyclohexyl]oxy}-2,6-difluoro-N-(pyrimidin-4-yl)benzenesulfonamide

[Formula 61]

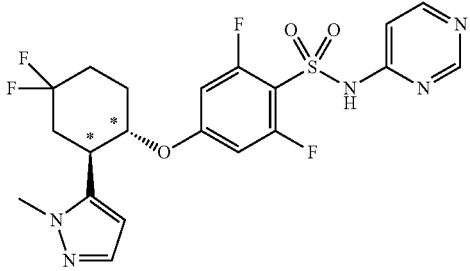

(39a) [(4,4-Difluorocyclohex-1-en-1-yl)oxy](trimethyl)silane

To a solution of N,N-diisopropylamine (3.30 g, 32.6 mmol) in THF (50 mL), n-butyl lithium (1.65 M solution in hexane; 18.0 mL, 29.7 mmol) was added dropwise with cooling on ice. The reaction solution was stirred at 0° C. for 30 minutes. Then, 4,4-difluorocyclohexanone (3.60 g, 26.8 mmol) was added thereto at −78° C., and the reaction solution was stirred at −78° C. for 1 hour. Chlorotrimethylsilane (4.4 mL, 34.8 mmol) and triethylamine (8.0 mL, 57.4 mmol) were added to the reaction solution, and the mixture was stirred at −78° C. for 2 hours. To the reaction solution, a saturated aqueous solution of sodium hydrogencarbonate (20 mL) was added, followed by extraction with ethyl acetate (20 mL). The thus obtained organic layer was dried over anhydrous sodium sulfate. After concentration under reduced pressure, the residue was purified with silica gel chromatography (hexane/ethyl acetate=98:2) to yield the title compound (2.10 g, 56%) as a colorless oil.

$^1$H-NMR (500 MHz, CDCl$_3$) δ ppm: 0.20 (9H, s), 2.04-2.12 (2H, m), 16.28 (2H, m), 2.50-2.56 (2H, m), 4.68-4.71 (1H, m).

(39b) 4,4-Difluorocyclohex-2-en-1-one

To a solution of the [(4,4-difluorocyclohex-1-en-1-yl)oxy](trimethyl)silane (3.1 g, 15.0 mmol) prepared in Example 39a in acetonitrile (25 mL), palladium acetate (4.0 g, 17.8 mmol) was added, and the mixture was stirred at room temperature for 45 minutes. The reaction solution was filtered, the filtrate was concentrated under reduced pressure, and the residue was then purified with silica gel chromatography (hexane/ethyl acetate=9:1) to yield the title compound (1.0 g, 50%) as a yellow oil.

$^1$H-NMR (400 MHz, CDCl$_3$) δ ppm: 2.47-2.56 (2H, m), 2.68 (2H, t, J=6.7 Hz), 6.19 (1H, d, J=10.6 Hz), 6.76-6.82 (1H, m).

(39c) 4,4-Difluoro-2-iodocyclohex-2-en-1-one

To the 4,4-difluorocyclohex-2-en-1-one (1.0 g, 7.57 mmol) prepared in Example 39b in a mixed solvent of THF and water (1:1; 20 mL), potassium carbonate (1.30 g, 9.41 mmol), iodine (2.9 g, 11.4 mmol), and DMAP (0.56 g, 4.58 mmol) were added, and the reaction solution was stirred at room temperature for 30 minutes. The reaction solution was subjected to extraction with ethyl acetate (20 mL). The thus obtained organic layer was washed with an aqueous sodium thiosulfate solution (20 mL) and dried over anhydrous sodium sulfate. After concentration under reduced pressure, the residue was purified with silica gel chromatography (hexane/ethyl acetate=9:1) to yield the title compound (1.46 g, 75%) as a light brown oil.

$^1$H-NMR (500 MHz, CDCl$_3$) δ ppm: 2.51-2.59 (2H, m), 2.87 (2H, t, J=6.8 Hz), 7.56-7.58 (1H, m).

(39d) 8,8-Difluoro-6-iodo-1,4-dioxaspiro[4.5]dec-6-ene

The reaction and aftertreatment were conducted in the same manner as in Example 22a by using the 4,4-difluoro-2-iodocyclohex-2-en-1-one (1.46 g, 5.66 mmol) prepared in Example 39c, ethylene glycol (750 mg, 12.1 mmol), p-toluenesulfonic acid hydrate (60 mg, 0.31 mmol), and benzene (30 mL), to yield a mixture of the title compound and a by-product.

(39e) 5-(8,8-Difluoro-1,4-dioxaspiro[4.5]dec-6-en-6-yl)-1-methyl-1H-pyrazole The reaction and aftertreatment were conducted in the same manner as in Example 12a by using the 8,8-difluoro-6-iodo-1,4-dioxaspiro[4.5]dec-6-ene (1.34 g, 4.44 mmol) prepared in Example 39d, 1-methyl-5-(4,4,5,5-tetramethyl-1,3,2-dioxaboran-2-yl)-1H-pyrazole (1.40 g, 6.73 mmol), tetrakis(triphenylphosphine)palladium(0) (250 mg, 0.216 mmol), cesium carbonate (3.40 g, 10.4 mmol), 1,4-dioxane (10 mL), and water (5.0 mL), to yield a mixture of the title compound and a by-product.

(39f) 4,4-Difluoro-2-(1-methyl-1H-pyrazol-5-yl)cyclohex-2-en-1-one

The reaction and aftertreatment were conducted in the same manner as in Example 22c by using the 5-(8,8-difluoro-1,4-dioxaspiro[4.5]dec-6-en-6-yl)-1-methyl-1H-pyrazole (758 mg, 2.96 mmol) prepared in Example 39e, 5 M hydrochloric acid (10 mL), and THF (10 mL), to yield the title compound (170 mg, 14%, 3 steps) as a colorless oil.

$^1$H-NMR (500 MHz, CDCl$_3$) δ ppm: 2.59-2.57 (2H, m), 2.85 (2H, t, J=6.8 Hz), 3.74 (3H, s), 6.29 (1H, d, J=2.0 Hz), 6.84 (1H, t, J=5.9 Hz), 7.48 (1H, d, J=2.0 Hz).

(39g) (1S*,2R*)-4,4-Difluoro-2-(1-methyl-1H-pyrazol-5-yl)cyclohexanol

The reaction and aftertreatment were conducted in the same manner as in Example 22d by using the 4,4-difluoro-2-(1-methyl-1H-pyrazol-5-yl)cyclohex-2-en-1-one (170 mg, 0.80 mmol) prepared in Example 39f, sodium borohydride (60 mg, 1.59 mmol), methanol (3.0 mL), palladium hydroxide carbon (10%; 150 mg), and ethanol (4.0 mL), to yield the title compound (50 mg, 29%) as a colorless solid.

$^1$H-NMR (500 MHz, CDCl$_3$) δ ppm: 1.80-2.00 (3H, m), 2.10-2.13 (1H, m), 12.31 (2H, m), 2.98-3.03 (1H, m), 3.73 (1H, dt, J=4.4, 10.3 Hz), 3.86 (3H, s), 6.08 (1H, d, J=2.0 Hz), 7.41 (1H, d, J=2.0 Hz).

(39h) 4-{[(1S*,2R*)-4,4-Difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (150 mg, 0.34 mmol) prepared in Example 4a, the (1S*,2R*)-4,4-difluoro-2-(1-methyl-1H-pyrazol-5-yl)cyclohexanol (61.6 mg, 0.28 mmol) prepared in Example 39g, sodium hydride (63%; 21.7 mg, 0.57 mmol) and DMF (2.0 mL), to yield the title compound (85.9 mg, 47%) as a colorless oil.

$^1$H-NMR (500 MHz, CDCl$_3$) δ ppm: 1.86-2.47 (6H, m), 3.33-3.38 (1H, m), 3.77 (3H, s), 3.81 (3H, s), 3.87 (3H, s), 4.24 (1H, dt, J=3.9, 10.3 Hz), 5.23 (2H, s), 6.04 (1H, d, J=2.0 Hz), 6.30 (2H, d, J=10.3 Hz), 6.40-6.44 (2H, m), 7.12 (1H, dd, J=1.5, 6.4 Hz), 7.21 (1H, d, J=8.3 Hz), 7.38 (1H, d, J=2.0 Hz), 8.44 (1H, d, J=5.9 Hz), 8.78 (1H, d, J=1.0 Hz).

(39i) 4-{[(1S*,2R*)-4,4-Difluoro-2-(1-methyl-1H-pyrazol-5-yl)cyclohexyl]oxy}-2,6-difluoro-N-(pyrimidin-4-yl)benzenesulfonamide The reaction and aftertreatment were conducted in the same manner as in Example 1e by using the 4-{[(1S*,2R*)-4,4-difluoro-2-(1-methyl-1H-pyrazol-5-yl)cyclohexyl]oxy}-N-(2,4-dimethoxybenzyl)-2,6-difluoro-N-(pyrimidin-4-yl)benzenesulfonamide (85.9 mg, 0.14 mmol) prepared in Example 39h, triethylsilane (0.10 mL), trifluoroacetic acid (1.0 mL) and dichloromethane (1.0 mL), to yield the title compound (58.0 mg, 88%) as a colorless solid.

$^1$H-NMR (500 MHz, CDCl$_3$) δ ppm: 1.88-2.45 (6H, m), 3.33-3.38 (1H, m), 3.88 (3H, s), 4.25 (1H, dt, J=3.9, 10.3 Hz), 6.06 (1H, d, J=2.0 Hz), 6.33 (2H, d, J=10.7 Hz), 7.38-7.40 (2H, m), 8.41 (1H, d, J=6.4 Hz), 8.85 (1H, s).
MS (ESI) m/z: 486 [M+H]$^+$.

Example 40

5-Chloro-4-{[(1S*,2R*)-4,4-difluoro-2-(1-methyl-1H-pyrazol-5-yl)cyclohexyl]oxy}-2-fluoro-N-(pyrimidin-4-yl)benzenesulfonamide

[Formula 62]

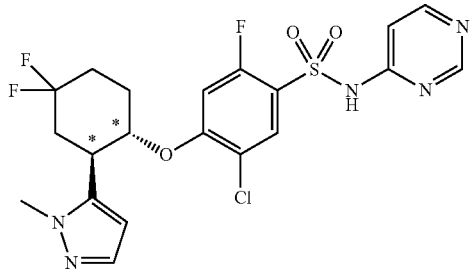

(40a) 5-Chloro-4-{[(1S*,2R*)-4,4-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (167 mg, 0.37 mmol) prepared in Example 2a, the (1S*,2R*)-4,4-difluoro-2-(1-methyl-1H-pyrazol-5-yl)cyclohexanol (65.9 mg, 0.30 mmol) prepared in Example 39g, sodium hydride (63%; 23.2 mg, 0.61 mmol) and DMF (2.0 mL), to yield the title compound (104 mg, 52%) as a colorless oil.

$^1$H-NMR (500 MHz, CDCl$_3$) δ ppm: 1.94-2.47 (6H, m), 3.44-3.50 (1H, m), 3.76 (6H, s), 3.94 (3H, s), 4.25 (1H, dt, J=4.4, 10.3 Hz), 5.19 (1H, d, J=17.6 Hz), 5.23 (1H, d, J=17.1 Hz), 6.07 (1H, d, J=2.0 Hz), 6.39-6.42 (3H, m), 7.17-7.20 (2H, m), 7.38 (1H, d, J=1.5 Hz), 7.96 (1H, d, J=7.3 Hz), 8.47 (1H, d, J=5.9 Hz), 8.79 (1H, s).

(40b) 5-Chloro-4-{[(1S*,2R*)-4,4-difluoro-2-(1-methyl-1H-pyrazol-5-yl)cyclohexyl]oxy}-2-fluoro-N-(pyrimidin-4-yl)benzenesulfonamide The reaction and aftertreatment were conducted in the same manner as in Example 1e by using the 5-chloro-4-{[(1S*,2R*)-4,4-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide (104 mg, 0.16 mmol) prepared in Example 40a, triethylsilane (0.10 mL), trifluoroacetic acid (1.0 mL) and dichloromethane (1.0 mL), to yield the title compound (72.2 mg, 90%) as a colorless solid.

$^1$H-NMR (500 MHz, CDCl$_3$) δ ppm: 1.94-2.49 (6H, m), 3.44-3.49 (1H, m), 3.94 (3H, s), 4.26 (1H, dt, J=4.4, 10.3 Hz), 6.09 (1H, d, J=2.4 Hz), 6.46 (1H, d, J=11.2 Hz), 7.26-7.27 (1H, m), 7.38 (1H, d, J=1.5 Hz), 7.97 (1H, d, J=7.3 Hz), 8.39 (1H, d, J=6.4 Hz), 8.79 (1H, s).
MS (ESI) m/z: 502 [M+H]$^+$.

Example 41

4-{[(1S*,2R*)-4,4-Difluoro-2-(1-methyl-1H-pyrazol-5-yl)cyclopentyl]oxy}-2-fluoro-5-methyl-N-(pyrimidin-4-yl)benzenesulfonamide

[Formula 63]

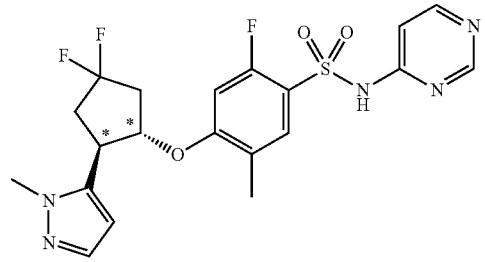

(41a) 4-{[(1S*,2R*)-4,4-Difluoro-2-(1-methyl-1H-pyrazol-5-yl)cyclopentyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (231 mg, 0.530 mmol) prepared in Example 10a, the (1S*,2R*)-4,4-difluoro-2-(1-methyl-1H-pyrazol-5-yl)cyclopentanol (101 mg, 0.500 mmol) prepared in Example 31f, sodium hydride (63%; 29 mg, 0.750 mmol), DMF (2.0 mL) and water (0.780 mL), to yield the title compound (175 mg, 57%) as a colorless amorphous solid.

$^1$H-NMR (500 MHz, CDCl$_3$) δ ppm: 2.21 (3H, s), 2.29-2.43 (2H, m), 2.76-2.89 (2H, m), 3.69-3.81 (1H, m), 3.77 (3H, s), 3.79 (3H, s), 3.87 (3H, s), 4.70 (1H, q, J=6.8 Hz), 5.24 (2H, s), 6.14 (1H, d, J=2.0 Hz), 6.30 (1H, d, J=11.2 Hz), 6.39-6.42 (2H, m), 7.16-7.26 (2H, m), 7.44 (1H, d, J=2.0 Hz), 7.79 (1H, d, J=8.8 Hz), 8.43 (1H, d, J=6.4 Hz), 8.76 (1H, s).

(41b) 4-{[(1S*,2R*)-4,4-Difluoro-2-(1-methyl-1H-pyrazol-5-yl)cyclopentyl]oxy}-2-fluoro-5-methyl-N-(pyrimidin-4-yl)benzenesulfonamide The reaction and aftertreatment were conducted in the same manner as in Example 1e by using the 4-{[(1S*,2R*)-4,4-difluoro-2-(1-methyl-1H-pyrazol-5-yl)cyclopentyl]oxy}-N-(2,4-dimethoxybenzyl)-2-fluoro-5-methyl-N-(pyrimidin-4-yl)benzenesulfonamide (171 mg, 0.277 mmol) prepared in Example 41a, triethylsilane (0.30 mL), trifluoroacetic acid (2.0 mL) and dichloromethane (3.0 mL), to yield the title compound (106 mg, 82%) as a colorless solid.

$^1$H-NMR (500 MHz, CDCl$_3$) δ ppm: 2.22 (3H, s), 2.27-2.43 (2H, m), 2.75-2.89 (2H, m), 3.70-3.75 (1H, m), 3.87 (3H, s), 4.70 (1H, q, J=6.4 Hz), 6.13 (1H, d, J=2.0 Hz), 6.36 (1H, d, J=11.7 Hz), 7.22 (1H, brs), 7.43 (1H, d, J=2.0 Hz), 7.78 (1H, d, J=8.3 Hz), 8.40 (1H, d, J=6.4 Hz), 8.81 (1H, brs).

MS (ESI) m/z: 468 [M+H]$^+$.

Example 42

4-{[(1S*,2R*)-4,4-Difluoro-2-(1-methyl-1H-pyrazol-5-yl)cyclopentyl]oxy}-2,6-difluoro-N-(pyrimidin-4-yl)benzenesulfonamide

[Formula 64]

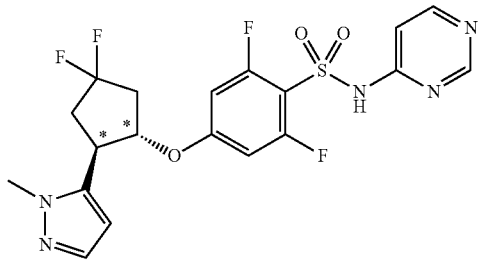

(42a) 4-{[(1S*,2R*)-4,4-Difluoro-2-(1-methyl-1H-pyrazol-5-yl)cyclopentyl]oxy}-N-(2,4-dimethoxybenzyl)-2,6-difluoro-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (233 mg, 0.530 mmol) prepared in the Example 4a, the (1S*,2R*)-4,4-difluoro-2-(1-methyl-1H-pyrazol-5-yl)cyclopentanol (101 mg, 0.500 mmol) prepared in Example 31f, sodium hydride (63%; 29 mg, 0.750 mmol), DMF (2.0 mL) and water (0.780 mL), to yield the title compound (98 mg, 32%) as a colorless solid.

$^1$H-NMR (500 MHz, CDCl$_3$) δ ppm: 2.29-2.40 (2H, m), 2.71-2.91 (2H, m), 3.65-3.70 (1H, m), 3.76 (3H, s), 3.81 (3H, s), 3.83 (3H, s), 4.71 (1H, q, J=6.8 Hz), 5.25 (2H, s), 6.14 (1H, d, J=2.0 Hz), 6.36-6.44 (4H, m), 7.12 (1H, dd, J=1.0, 5.9 Hz), 7.21 (1H, d, J=8.3 Hz), 7.42 (1H, d, J=2.0 Hz), 8.44 (1H, d, J=5.9 Hz), 8.78 (1H, d, J=1.0 Hz).

(42b) 4-{[(1S*,2R*)-4,4-Difluoro-2-(1-methyl-1H-pyrazol-5-yl)cyclopentyl]oxy}-2,6-difluoro-N-(pyrimidin-4-yl)benzenesulfonamide The reaction and aftertreatment were conducted in the same manner as in Example 1e by using the 4-{[(1S*,2R*)-4,4-difluoro-2-(1-methyl-1H-pyrazol-5-yl)cyclopentyl]oxy}-N-(2,4-dimethoxybenzyl)-2,6-difluoro-N-(pyrimidin-4-yl)benzenesulfonamide (98 mg, 0.158 mmol) prepared in Example 42a, triethylsilane (0.30 mL), trifluoroacetic acid (2.0 mL) and dichloromethane (3.0 mL), to yield the title compound (54 mg, 73%) as a colorless solid.

$^1$H-NMR (500 MHz, CDCl$_3$) δ ppm: 2.29-2.41 (2H, m), 2.73-2.89 (2H, m), 3.65-3.70 (1H, m), 3.84 (3H, s), 4.68 (1H, q, J=6.8 Hz), 6.13 (1H, d, J=2.0 Hz), 6.39 (2H, d, J=10.7 Hz), 7.30 (1H, brs), 7.43 (1H, d, J=2.0 Hz), 8.43 (1H, d, J=5.9 Hz), 8.78 (1H, brs).

MS (ESI) m/z: 472 [M+H]$^+$.

Example 43

4-{[(1S,2R)-5,5-Difluoro-2-(1-methyl-1H-pyrazol-5-yl)cyclohexyl]oxy}-2-fluoro-5-methyl-N-(pyrimidin-4-yl)benzenesulfonamide

[Formula 65]

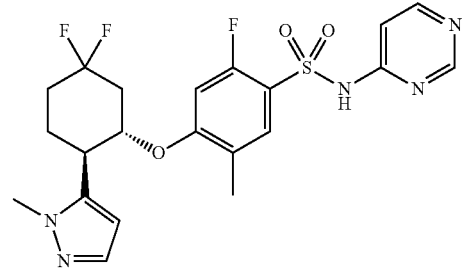

(43a) 4-{[(1S,2R)-5,5-Difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl) benzenesulfonamide (175 mg, 0.401 mmol) prepared in Example 10a, the (1S,2R)-5,5-difluoro-2-(1-methyl-1H-pyrazol-5-yl)cyclohexanol (72.3 mg, 0.334 mmol) prepared in Example 30c, sodium hydride (63%; 25.5 mg, 0.668 mmol) and DMF (2.0 mL), to yield the title compound (198 mg, 94%) as a colorless oil.

(43b) 4-{[(1S,2R)-5,5-Difluoro-2-(1-methyl-1H-pyrazol-5-yl)cyclohexyl]oxy}-2-fluoro-5-methyl-N-(pyrimidin-4-yl)benzenesulfonamide The reaction and aftertreatment were conducted in the same manner as in Example 1e by using the 4-{[(1S,2R)-

5,5-difluoro-2-(1-methyl-1H-pyrazol-5-yl)cyclohexyl]oxy}-N-(2,4-dimethoxybenzyl)-2-fluoro-5-methyl-N-(pyrimidin-4-yl)benzenesulfonamide (198 mg, 0.313 mmol) prepared in Example 43a, triethylsilane (0.10 mL), trifluoroacetic acid (1.0 mL) and dichloromethane (1.0 mL), to yield the title compound (80 mg, 53%) as a colorless solid. $[\alpha]_D^{25}$=−12.4 (c 1.01, DMSO).

Example 44

2-Fluoro-5-methyl-4-{[(1S*,2R*)-2-(1H-pyrazol-5-yl)cyclopentyl]oxy}-N-(pyrimidin-4-yl)benzenesulfonamide

[Formula 66]

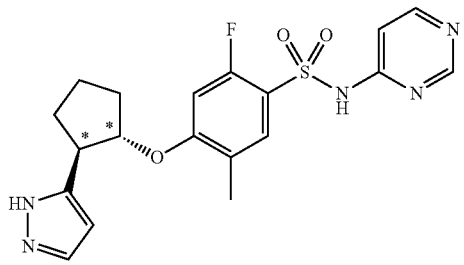

(44a) (1S*,2R*)-2-[1-(Tetrahydro-2H-pyran-2-yl)-1H-pyrazol-5-yl]cyclopentanol

To a solution of 1-(tetrahydro-2H-pyran-2-yl)-1H-pyrazole (3.04 g, 20.0 mmol) in THF (30 mL), n-butyl lithium (1.63 M solution in hexane; 12.7 mL, 20.7 mmol) was added dropwise at −78° C. for 7 minutes. The reaction solution was stirred for 30 minutes, and boron trifluoride-ethyl ether (3.14 mL, 25.0 mmol) was then added thereto. The reaction solution was further stirred for 10 minutes. Then, cyclopentene oxide (2.08 mL, 24.0 mmol) was added thereto, and the reaction solution was stirred at −78° C. for 3 hours. To the reaction solution, a saturated aqueous solution of sodium hydrogencarbonate (15 mL) was added, followed by extraction four times with ethyl acetate (20 mL). The thus obtained organic layer was dried over anhydrous sodium sulfate. After concentration under reduced pressure, the residue was purified with silica gel chromatography (hexane/ethyl acetate=1:4) to yield the title compound (1.54 g, 33%) in the form of a diastereomeric mixture as a colorless oil.

(44b) N-(2,4-Dimethoxybenzyl)-2-fluoro-5-methyl-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (218 mg, 0.50 mmol) prepared in Example 10a, the (1S*,2R*)-2-[1-(tetrahydro-2H-pyran-2-yl)-1H-pyrazol-5-yl]cyclopentanol (154 mg, 0.65 mmol) prepared in Example 44a, sodium hydride (63%; 38 mg, 1.0 mmol), DMF (3.0 mL) and water (1.1 mL), to yield the title compound (165 mg, 51%) in the form of a diastereomeric mixture as a colorless amorphous solid.

(44c) 2-Fluoro-5-methyl-4-{[(1S*,2R*)-2-(1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2-fluoro-5-methyl-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide (155 mg, 0.238 mmol) prepared in Example 44b, triethylsilane (0.30 mL), trifluoroacetic acid (2.0 mL) and dichloromethane (3.0 mL), to yield the title compound (108 mg, 99%) as a colorless solid.

$^1$H-NMR (500 MHz, CD$_3$OD) δ ppm: 1.80-1.94 (4H, m), 2.20 (3H, s), 2.22-2.28 (2H, m), 3.38-3.42 (1H, m), 4.84-4.92 (1H, m), 6.19 (1H, d, J=2.4 Hz), 6.71 (1H, d, J=12.7 Hz), 7.97 (1H, d, J=5.9 Hz), 7.52 (1H, d, J=2.0 Hz), 7.75 (1H, d, J=8.3 Hz), 8.32 (1H, d, J=6.4 Hz), 8.57 (1H, s).

MS (ESI) m/z: 418 [M+H]$^+$.

Example 45

2,6-Difluoro-4-{[(1S*,2R*)-2-(1H-pyrazol-5-yl)cyclopentyl]oxy}-N-(pyrimidin-4-yl)benzenesulfonamide

[Formula 67]

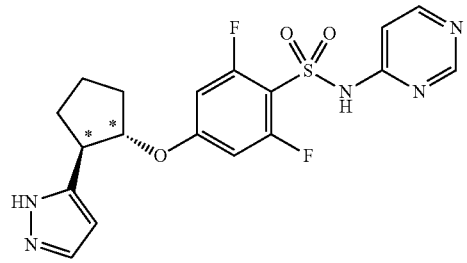

(45a) N-(2,4-Dimethoxybenzyl)-2,6-difluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (220 mg, 0.50 mmol) prepared in Example 4a, the (1S*,2R*)-2-[1-(tetrahydro-2H-pyran-2-yl)-1H-pyrazol-5-yl]cyclopentanol (154 mg, 0.65 mmol) prepared in Example 44a, sodium hydride (63%; 38 mg, 1.0 mmol), DMF (3.0 mL) and water (1.1 mL), to yield the title compound (122 mg, 37%) in the form of a diastereomeric mixture as colorless amorphous solid.

(45b) 2,6-Difluoro-4-{[(1S*,2R*)-2-(1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2,6-difluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide (121 mg, 0.185 mmol) prepared in Example 45a, triethylsilane (0.30 mL), trifluoroacetic acid (2.0 mL) and dichloromethane (3.0 mL), to yield the title compound (67 mg, 86%) as a colorless solid.

$^1$H-NMR (500 MHz, CDCl$_3$) δ ppm: 1.83-1.94 (4H, m), 2.17-2.29 (2H, m), 3.42-3.46 (1H, m), 4.842 (1H, m), 6.20 (1H, d, J=2.4 Hz), 6.47 (2H, d, J=13.2 Hz), 7.45 (1H, d, J=7.3 Hz), 7.57 (1H, d, J=2.0 Hz), 8.41 (1H, d, J=6.4 Hz), 8.87 (1H, d, J=1.0 Hz), 10.06 (2H, brs).

MS (ESI) m/z: 422 [M+H]$^+$.

Example 46

5-Chloro-2-fluoro-4-{[(1S*,2R*)-2-(1H-pyrazol-5-yl)cyclopentyl]oxy}-N-(pyrimidin-4-yl)benzenesulfonamide

[Formula 68]

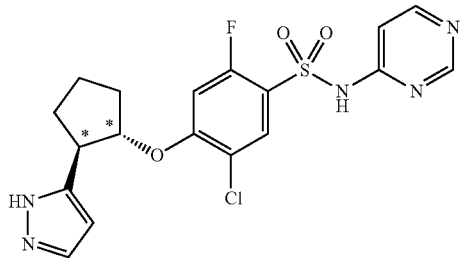

(46a) 5-Chloro-N-(2,4-dimethoxybenzyl)-2-fluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (228 mg, 0.50 mmol) prepared in Example 2a, the (1S*,2R*)-2-[1-(tetrahydro-2H-pyran-2-yl)-1H-pyrazol-5-yl]cyclopentanol (154 mg, 0.65 mmol) prepared in Example 44a, sodium hydride (63%; 38 mg, 1.0 mmol), DMF (3.0 mL) and water (1.1 mL), to yield the title compound (128 mg, 38%) in the form of a diastereomeric mixture as a colorless amorphous solid.

(46b) 5-Chloro-2-fluoro-4-{[(1S*,2R*)-2-(1H-pyrazol-5-yl)cyclopentyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-N-(pyrimidin-4-yl)-4-({(1S*,2R*)-2-[1-(tetrahydro-2H-pyran-2-yl)-1H-pyrazol-5-yl]cyclopentyl}oxy)benzenesulfonamide (126 mg, 0.187 mmol) prepared in Example 46a, triethylsilane (0.30 mL), trifluoroacetic acid (2.0 mL) and dichloromethane (3.0 mL), to yield the title compound (63 mg, 77%) as a colorless solid.

$^1$H-NMR (500 MHz, CDCl$_3$) δ ppm: 1.89-2.01 (4H, m), 2.18-2.34 (2H, m), 3.49-3.52 (1H, m), 5.03-5.04 (1H, m), 6.23 (1H, d, J=2.4 Hz), 6.72 (1H, d, J=11.7 Hz), 7.32 (1H, d, J=5.4 Hz), 7.56 (1H, d, J=2.0 Hz), 7.99 (1H, d, J=7.3 Hz), 8.40 (1H, d, J=6.4 Hz), 8.81 (1H, d, J=1.0 Hz).

MS (ESI) m/z: 438 [M+H]$^+$.

Example 47

5-Chloro-4-{[(1S*,2R*)-5,5-difluoro-2-(1-methyl-1H-pyrazol-5-yl)cyclohexyl]oxy}-2-fluoro-N-(pyrimidin-4-yl)benzenesulfonamide

[Formula 69]

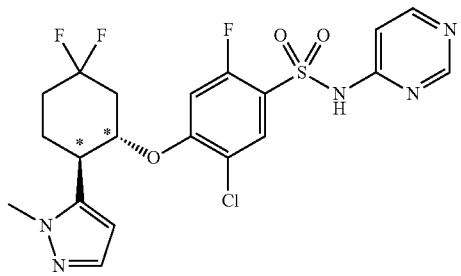

(47a) 5-Chloro-4-{[(1S*,2R*)-5,5-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (202 mg, 0.444 mmol) prepared in Example 2a, the (1S*,2R*)-5,5-difluoro-2-(1-methyl-1H-pyrazol-5-yl)cyclohexanol (80.0 mg, 0.370 mmol) prepared in Example 12b, sodium hydride (63%; 21.1 mg, 0.555 mmol) and DMF (2.0 mL), to yield the title compound (212 mg, 88%) as a colorless oil.

$^1$H-NMR (500 MHz, CDCl$_3$) δ ppm: 1.84-2.14 (4H, m), 2.29-2.33 (1H, m), 2.66-2.71 (1H, m), 3.12-3.17 (1H, m), 3.78 (3H, s), 3.78 (3H, s), 3.93 (3H, s), 4.35 (1H, dt, J=5.9, 10.7 Hz), 5.20 (2H, s), 6.08 (1H, d, J=2.4 Hz), 6.39-6.43 (3H, m), 7.17-7.19 (2H, m), 7.37 (1H, d, J=2.0 Hz), 7.96 (1H, d, J=7.3 Hz), 8.47 (1H, d, J=5.9 Hz), 8.79 (1H, s).

(47b) 5-Chloro-4-{[(1S*,2R*)-5,5-difluoro-2-(1-methyl-1H-pyrazol-5-yl)cyclohexyl]oxy}-2-fluoro-N-(pyrimidin-4-yl)benzenesulfonamide The reaction and aftertreatment were conducted in the same manner as in Example 1e by using the 5-chloro-4-{[(1S*,2R*)-5,5-difluoro-2-(1-methyl-1H-pyrazol-5-yl)cyclohexyl]oxy}-N-(2,4-dimethoxybenzyl)-2-fluoro-N-(pyrimidin-4-yl)benzenesulfonamide (212 mg, 0.325 mmol) prepared in Example 47a, triethylsilane (0.10 mL), trifluoroacetic acid (1.0 mL) and dichloromethane (1.0 mL), to yield the title compound (135 mg, 83%) as a colorless solid.

$^1$H-NMR (500 MHz, CDCl$_3$) δ ppm: 1.91-2.14 (4H, m), 2.29-2.34 (1H, m), 2.66-2.71 (1H, m), 3.12-3.17 (1H, m), 3.92 (3H, s), 4.37 (1H, dt, J=4.4, 10.7 Hz), 6.09 (1H, d, J=2.0 Hz), 6.48 (1H, d, J=11.2 Hz), 7.19 (1H, d, J=6.4 Hz), 7.36 (1H, d, J=2.0 Hz), 7.97 (1H, d, J=7.3 Hz), 8.37 (1H, d, J=6.4 Hz), 8.70 (1H, s).

MS (ESI) m/z: 502 [M+H]$^+$.

Example 48

4-{[(1S,2R)-5,5-Difluoro-2-(1H-pyrazol-4-yl)cyclohexyl]oxy}-2-fluoro-5-methyl-N-(pyrimidin-4-yl)benzenesulfonamide

[Formula 70]

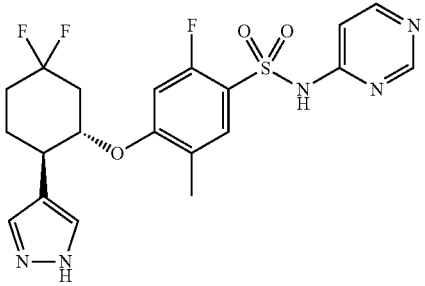

(48a) 4,4-Difluoro-1-(1H-pyrazol-4-yl)cyclohexanol

The reaction and aftertreatment were conducted in the same manner as in Example 1c by using 4-iodo-1H-pyrazole (5.82 g, 30.0 mmol), butyl lithium (2.69 M solution in hexane; 22.3 mL, 60.0 mmol), 4,4-difluorocyclohexanone (4.43 g, 33.0 mmol) and THF (120 mL), to yield the title compound (2.32 g, 55%) as a pale yellow solid.

$^1$H-NMR (500 MHz, CDCl$_3$) δ ppm: 1.95-2.05 (6H, m), 2.18-2.35 (2H, m), 2.55 (1H, t, J=7.3 Hz), 7.55 (2H, s).

(48b) 4-(4,4-Difluorocyclohex-1-en-1-yl)-1H-pyrazole

The reaction and aftertreatment were conducted in the same manner as in Example 38b by using the 4,4-difluoro-1-(1H-pyrazol-4-yl)cyclohexanol (0.25 g, 1.24 mmol) prepared in Example 48a, p-toluenesulfonic acid monohydrate (120 mg, 0.62 mmol) and toluene (3.0 mL), to yield the title compound (189 mg, 83%) as a colorless solid.

$^1$H-NMR (500 MHz, CDCl$_3$) δ ppm: 2.11-2.19 (2H, m), 2.57-2.69 (4H, m), 5.82-5.84 (1H, m), 7.61 (2H, s).

(48c) (1S*,2R*)-5,5-Difluoro-2-(1H-pyrazol-4-yl)cyclohexanol

The reaction and aftertreatment were conducted in the same manner as in Example 29b by using the 4-(4,4-difluorocyclohex-1-en-1-yl)-1H-pyrazole (0.30 g, 1.63 mmol) prepared in Example 48b, a borane-THF complex (0.95 M solution in THF; 3.77 mL, 3.59 mmol), sodium perborate tetrahydrate (0.55 g, 3.59 mmol), THF (1.6 mL) and water (2.4 mL), to yield the title compound (0.31 g, 94%) as a colorless solid.

$^1$H-NMR (500 MHz, CDCl$_3$) δ ppm: 1.74-1.99 (4H, m), 2.15-2.22 (1H, m), 2.52-2.59 (2H, m), 3.69 (1H, dt, J=4.4, 10.7 Hz), 7.52 (2H, s).

(48d) (1S*,2R*)-5,5-Difluoro-2-[1-(4-methoxybenzyl)-1H-pyrazol-4-yl]cyclohexanol A solution of the (1S*,2R*)-5,5-difluoro-2-(1H-pyrazol-4-yl)cyclohexanol (0.24 g, 1.17 mmol) prepared in Example 48c, potassium carbonate (0.32 g, 2.34 mmol) and 4-methoxybenzyl chloride (0.16 mL, 1.17 mmol) in acetonitrile (5.9 mL) was stirred at 80° C. for 12 hours. After allowing to cool, water (20 mL) was added to the reaction solution, and an organic layer was extracted with ethyl acetate (20 mL). The thus obtained organic layer was dried over anhydrous sodium sulfate. After concentration under reduced pressure, the residue was purified with silica gel chromatography to yield the title compound (92.9 mg, 25%) as a colorless solid.

$^1$H-NMR (500 MHz, CDCl$_3$) δ ppm: 1.63-1.98 (4H, m), 2.11-2.18 (1H, m), 2.41-2.54 (2H, m), 3.61 (1H, dt, J=4.4, 10.7 Hz), 3.80 (3H, s), 5.15 (2H, s), 6.88 (2H, d, J=8.8 Hz), 7.19 (2H, d, J=8.3 Hz), 7.24 (1H, s), 7.39 (1H, s).

(48e) (1S,2R)-5,5-Difluoro-2-[1-(4-methoxybenzyl)-1H-pyrazol-4-yl]cyclohexanol The (1S*,2R*)-5,5-difluoro-2-[1-(4-methoxybenzyl)-1H-pyrazol-4-yl]cyclohexanol prepared in Example 48d was optically resolved with CHIRALPAK IA (Daicel Corp.; hexane/isopropanol=8:2) to yield the title compound as a colorless solid.

(48f) 4-({(1S,2R)-5,5-Difluoro-2-[1-(4-methoxybenzyl)-1H-pyrazol-4-yl]cyclohexyl}oxy)-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (0.16 g, 0.37 mmol) prepared in Example 10a, the (1S,2R)-5,5-difluoro-2-[1-(4-methoxybenzyl)-1H-pyrazol-4-yl]cyclohexanol (0.09 g, 0.29 mmol) prepared in Example 48e, sodium hydride (63%; 10 mg, 0.37 mmol), DMF (1.8 mL) and water (0.010 mL), to yield the title compound (177.7 mg, 66%) as a colorless amorphous solid.

$^1$H-NMR (500 MHz, CDCl$_3$) δ ppm: 1.86-2.00 (3H, m), 2.07 (3H, s), 2.18 (2H, m), 2.64-2.66 (1H, m), 2.90-2.94 (1H, m), 3.78 (3H, s), 3.80 (3H, s), 3.81 (3H, s), 4.22 (1H, dt, J=4.4, 10.3 Hz), 5.13 (2H, s), 5.26 (1H, d, J=16.6 Hz), 5.30 (1H, d, J=17.1 Hz), 6.38-6.43 (3H, m), 6.85 (2H, d, J=6.4 Hz), 7.07 (2H, d, J=8.8 Hz), 7.12 (1H, s), 7.19-7.22 (2H, m), 7.40 (1H, s), 7.72 (1H, d, J=7.8 Hz), 8.44 (1H, d, J=5.9 Hz), 8.78 (1H, d, J=1.0 Hz).

(48g) 4-{[(1S,2R)-5,5-Difluoro-2-(1H-pyrazol-4-yl)cyclohexyl]oxy}-2-fluoro-5-methyl-N-(pyrimidin-4-yl)benzenesulfonamide A solution of the 4-({(1S,2R)-5,5-difluoro-2-[1-(4-methoxybenzyl)-1H-pyrazol-4-yl]cyclohexyl}oxy)-N-(2,4-dimethoxybenzyl)-2-fluoro-5-methyl-N-(pyrimidin-4-yl)benzenesulfonamide (0.15 g, 0.20 mmol) prepared in Example 48f, triethylsilane (0.16 mL) and trifluoroacetic acid (0.20 mL) in dichloromethane (2.0 mL) was stirred at 140° C. for 1 hour under microwave irradiation. The reaction solution was concentrated, and the residue was purified with silica gel chromatography (ethyl acetate) to yield the title compound (90 mg, 94%) as a colorless solid.

Example 49

5-Chloro-4-{[(1S*,2R*)-4,4-difluoro-2-(1-methyl-1H-pyrazol-5-yl)cyclopentyl]oxy}-2-fluoro-N-(pyrimidin-4-yl)benzenesulfonamide

[Formula 71]

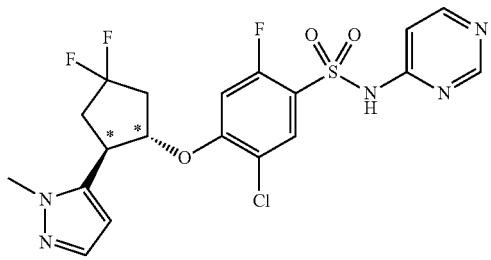

(49a) 5-Chloro-4-{[(1S*,2R*)-4,4-difluoro-2-(1-methyl-1H-pyrazol-5-yl)cyclopentyl]oxy}-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (274 mg, 0.600 mmol) prepared in Example 2a, the (1S*,2R*)-4,4-difluoro-2-(1-methyl-1H-pyrazol-5-yl)cyclopentanol (101 mg, 0.500 mmol) prepared in Example 31f, sodium hydride (63%; 29 mg, 0.750 mmol), DMF (2.0 mL) and water (0.016 mL), to yield the title compound (316 mg, 99%) as a colorless amorphous solid.

$^1$H-NMR (500 MHz, CDCl$_3$) δ ppm: 2.29-2.46 (2H, m), 2.72-2.93 (2H, m), 3.75 (3H, s), 3.78 (3H, s), 3.79-3.87 (1H, m), 3.93 (3H, s), 4.71 (1H, q, J=6.8 Hz), 5.20 (1H, d, J=16.6 Hz), 5.24 (1H, d, J=16.6 Hz), 6.15 (1H, d, J=2.0 Hz), 6.37-6.40 (2H, m), 6.47 (1H, d, J=10.7 Hz), 7.17-7.18 (2H, m), 7.42 (1H, d, J=2.0 Hz), 8.03 (1H, d, J=7.3 Hz), 8.46 (1H, d, J=5.9 Hz), 8.78 (1H, d, J=1.0 Hz).

(49b) 5-Chloro-4-{[(1S*,2R*)-4,4-difluoro-2-(1-methyl-1H-pyrazol-5-yl)cyclopentyl]oxy}-2-fluoro-N-(pyrimidin-4-yl)benzenesulfonamide The reaction and aftertreatment were conducted in the same manner as in Example 1e by using the 5-chloro-4-{[(1S*,2R*)-4,4-difluoro-2-(1-methyl-1H-pyrazol-5-yl)cyclopentyl]oxy}-N-(2,4-dimethoxybenzyl)-2-fluoro-N-(pyrimidin-4-yl)benzenesulfonamide (316 mg, 0.495 mmol) prepared in Example 49a, triethylsilane (0.30 mL), trifluoroacetic acid (2.0 mL) and dichloromethane (3.0 mL), to yield the title compound (237 mg, 98%) as a colorless solid.

$^1$H-NMR (500 MHz, CD$_3$OD) δ ppm: 2.28-2.51 (2H, m), 2.72-2.79 (1H, m), 2.95-3.06 (1H, m), 3.81-3.90 (1H, m), 3.87 (3H, s), 5.00 (1H, q, J=6.8 Hz), 6.31 (1H, d, J=2.0 Hz), 6.93 (1H, d, J=11.2 Hz), 7.00 (1H, brs), 7.39 (1H, d, J=2.0 Hz), 8.01 (1H, d, J=7.3 Hz), 8.24 (1H, brs), 8.52 (1H, s).

MS (ESI) m/z: 488 [M+H]$^+$.

Example 50

2-Fluoro-5-methyl-4-{[(1S,2R)-2-(1H-pyrazol-5-yl)cyclopentyl]oxy}-N-(pyrimidin-4-yl)benzenesulfonamide

[Formula 72]

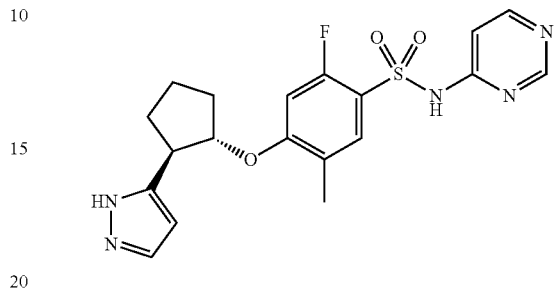

(50a) 5-[(1R*,2S*)-2-(Benzyloxy)cyclopentyl]-1-(tetrahydro-2H-pyran-2-yl)-1H-pyrazole To a solution of the (1S*,2R*)-2-[1-(tetrahydro-2H-pyran-2-yl)-1H-pyrazol-5-yl]cyclopentanol (975 mg, 4.13 mmol) prepared in Example 44a in DMF (20 m), sodium hydride (63%; 236 mg, 6.19 mmol) and benzyl bromide (0.735 mL, 6.19 mmol) were added, and the reaction solution was stirred at room temperature for 7 hours. To the reaction solution, water (50 mL) was added, followed by extraction with ethyl acetate (50 mL). The thus obtained organic layer was washed twice with water (50 mL) and dried over anhydrous sodium sulfate. After concentration under reduced pressure, the residue was purified with silica gel chromatography (hexane/ethyl acetate=7:3) to yield the title compound (1.15 g, 57%) in the form of a diastereomeric mixture as a colorless oil.

(50b) 5-[(1R*,2S*)-2-(Benzyloxy)cyclopentyl]-1H-pyrazole

To a solution of the 5-[(1R*,2S*)-2-(benzyloxy)cyclopentyl]-1-(tetrahydro-2H-pyran-2-yl)-1H-pyrazole (1.15 g, 3.52 mmol) prepared in Example 50a in dichloromethane (10 mL), trifluoroacetic acid (5.0 mL) was added at room temperature, and the reaction solution was stirred for 12 hours. The reaction solution was concentrated, and a saturated aqueous solution of sodium hydrogencarbonate (50 mL) was added to the residue, followed by extraction with ethyl acetate (50 mL). The thus obtained organic layer was washed with saturated saline (50 mL) and dried over anhydrous sodium sulfate. After concentration under reduced pressure, the residue was purified with silica gel chromatography (hexane/ethyl acetate=1:1) to yield the title compound (840 mg, 98%) as a pale yellow oil.

$^1$H-NMR (500 MHz, CDCl$_3$) δ ppm: 1.73-1.92 (4H, m), 2.02-2.10 (1H, m), 2.16-2.23 (1H, m), 3.16-3.21 (1H, m), 3.95 (1H, q, J=6.4 Hz), 4.47 (1H, d, J=11.2 Hz), 4.57 (1H, d, J=11.7 Hz), 6.08 (1H, d, J=2.9 Hz), 7.26-7.34 (5H, m), 7.48 (1H, d, J=2.0 Hz).

(50c) 5-[(1R,2S)-2-(Benzyloxy)cyclopentyl]-1H-pyrazole

The 5-[(1R*,2S*)-2-(benzyloxy)cyclopentyl]-1H-pyrazole prepared in Example 50b was optically resolved with CHIRALPAK AD-H (Daicel Corp.; hexane/isopropanol=9:1) to yield the title compound as a pale yellow oil.

(50d) 3-[(1R,2S)-2-(Benzyloxy)cyclopentyl]-1-(tetrahydro-2H-pyran-2-yl)-1H-pyrazole A solution of the 5-[(1R,2S)-2-(benzyloxy)cyclopentyl]-1H-pyrazole (322 mg, 1.33 mmol) prepared in Example 50c, 3,4-dihydro-2H-pyran (0.728 mL, 7.98 mmol) and p-toluenesulfonic acid hydrate (50 mg, 0.266 mmol) in dichloromethane (5.0 mL) was heated under reflux with stirring for 3 hours. After allowing to cool, the reaction solution was concentrated under reduced pressure, and the residue was purified with silica gel chromatography (hexane/ethyl acetate=7:3) to yield the title compound (402 mg, 93%) in the form of a diastereomeric mixture as a colorless oil.

(50e) (1S,2R)-2-[1-(Tetrahydro-2H-pyran-2-yl)-1H-pyrazol-3-yl]cyclopentanol

The reaction and aftertreatment were conducted in the same manner as in Example 28b by using the 3-[(1R,2S)-2-(benzyloxy)cyclopentyl]-1-(tetrahydro-2H-pyran-2-yl)-1H-pyrazole (403 mg, 1.23 mmol) prepared in Example 50d, palladium carbon (5%; 400 mg) and ethanol (20 mL) to yield the title compound (265 mg, 91%) in the form of a diastereomeric mixture as a colorless oil.

(50f) N-(2,4-Dimethoxybenzyl)-2-fluoro-5-methyl-N-(pyrimidin-4-yl)-4-({(1S,2R)-2-[1-(tetrahydro-2H-pyran-2-yl)-1H-pyrazol-3-yl]cyclopentyl}oxy)benzenesulfonamide The reaction and aftertreatment were conducted in the same manner as in Example 1d by using the N-(2,4-dimethoxybenzyl)-2-fluoro-5-methyl-N-(pyrimidin-4-yl)benzenesulfonamide (239 mg, 0.55 mmol) prepared in Example 10a, the (1S,2R)-2-[1-(tetrahydro-2H-pyran-2-yl)-1H-pyrazol-3-yl]cyclopentanol (118 mg, 0.50 mmol) prepared in Example 50e, sodium hydride (63%; 29 mg, 0.75 mmol), DMF (3.0 mL) and water (0.016 mL), to yield the title compound (267 mg, 82%) in the form of a diastereomeric mixture as a colorless amorphous solid.

(50g) 2-Fluoro-5-methyl-4-{[(1S,2R)-2-(1H-pyrazol-5-yl)cyclopentyl]oxy}-N-(pyrimidin-4-yl)benzenesulfonamide The reaction and aftertreatment were conducted in the same manner as in Example 1e by using the N-(2,4-dimethoxybenzyl)-2-fluoro-5-methyl-N-(pyrimidin-4-yl)-4-({(1S,2R)-2-[1-(tetrahydro-2H-pyran-2-yl)-1H-pyrazol-5-yl]cyclopentyl}oxy)benzenesulfonamide (265 mg, 0.407 mmol) prepared in Example 50f, triethylsilane (0.60 mL), trifluoroacetic acid (4.0 mL) and dichloromethane (6.0 mL), to yield the title compound (168 mg, 99%) as a colorless solid.

$[\alpha]_D^{25}$=60.5 (c 1.02, DMSO).

Example 51

5-Chloro-2-fluoro-4-{[(1S,2R)-2-(1H-pyrazol-5-yl)cyclopentyl]oxy}-N-(pyrimidin-4-yl)benzenesulfonamide

[Formula 73]

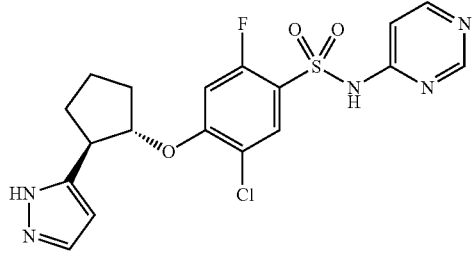

(51a) 5-Chloro-N-(2,4-dimethoxybenzyl)-2-fluoro-N-(pyrimidin-4-yl)-4-({(1S,2R)-2-[1-(tetrahydro-2H-pyran-2-yl)-1H-pyrazol-3-yl]cyclopentyl}oxy)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (251 mg, 0.55 mmol) prepared in Example 2a, the (1S,2R)-2-[1-(tetrahydro-2H-pyran-2-yl)-1H-pyrazol-3-yl]cyclopentanol (118 mg, 0.50 mmol) prepared in Example 50e, sodium hydride (63%; 29 mg, 0.75 mmol), DMF (3.0 mL) and water (0.016 mL), to yield the title compound (281 mg, 84%) in the form of a diastereomeric mixture as a colorless amorphous solid.

(51b) 5-Chloro-2-fluoro-4-{[(1S,2R)-2-(1H-pyrazol-5-yl)cyclopentyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-N-(pyrimidin-4-yl)-4-({(1S,2R)-2-[1-(tetrahydro-2H-pyran-2-yl)-1H-pyrazol-3-yl]cyclopentyl}oxy)benzenesulfonamide (281 mg, 0.418 mmol) prepared in Example 51a, triethylsilane (0.60 mL), trifluoroacetic acid (4.0 mL) and dichloromethane (6.0 mL), to yield the title compound (182 mg, 99%) as a colorless solid.

$[\alpha]_D^{25}$=65.0 (c 1.05, DMSO).

Example 52

5-Chloro-4-{[(1S*,2R*)-5,5-difluoro-2-(1H-pyrazol-4-yl)cyclohexyl]oxy}-2-fluoro-N-(pyrimidin-4-yl)benzenesulfonamide

[Formula 74]

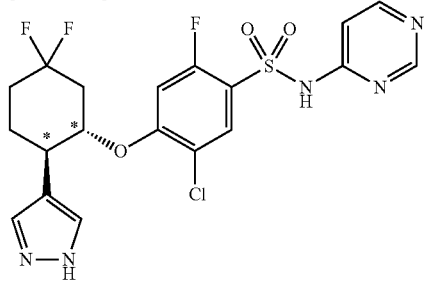

(52a) 5-Chloro-4-({(1S*,2R*)-5,5-difluoro-2-[1-(methoxymethyl)-1H-pyrazol-4-yl]cyclohexyl}oxy)-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (0.22 g, 0.48 mmol) prepared in Example 2a, the (1S*,2R*)-5,5-difluoro-2-[1-(methoxymethyl)-1H-pyrazol-4-yl]cyclohexanol (0.10 g, 0.40 mmol) prepared in Example 48d, sodium hydride (63%; 24 mg, 0.60 mmol) and DMF (5.0 mL), to yield the title compound (0.24 g, 87%) as a colorless oil.

$^1$H-NMR (500 MHz, CDCl$_3$) δ ppm: 1.88-2.10 (3H, m), 2.17-2.31 (2H, m), 2.65-2.69 (1H, m), 3.01-3.06 (1H, m), 3.22 (3H, s), 3.77 (3H, s), 3.78 (3H, s), 4.21 (1H, dt, J=4.4, 10.3 Hz), 5.21 (2H, s), 5.27 (1H, d, J=10.7 Hz), 5.29 (1H, d, J=10.7 Hz), 6.39-6.41 (2H, m), 6.47 (1H, d, J=11.7 Hz), 7.18-7.20 (2H, m), 7.47 (1H, s), 7.50 (1H, s), 7.99 (1H, d, J=7.3 Hz), 8.46 (1H, d, J=5.9 Hz), 8.79 (1H, d, J=1.0 Hz).

(52b) 5-Chloro-4-{[(1S*,2R*)-5,5-difluoro-2-(1H-pyrazol-4-yl)cyclohexyl]oxy}-2-fluoro-N-(pyrimidin-4-yl)benzenesulfonamide To a solution of the 5-chloro-4-({(1S*,2R*)-5,5-difluoro-2-[1-(methoxymethyl)-1H-pyrazol-4-yl]cyclohexyl}oxy)-N-(2,4-dimethoxybenzyl)-2-fluoro-N-(pyrimidin-4-yl)benzenesulfonamide (0.20 g, 0.29 mmol) prepared in Example 52a and triethylsilane (0.20 mL) in dichloromethane (2.0 mL), trifluoroacetic acid (2.0 mL) was added at room temperature, and the reaction solution was stirred at room temperature for 2 hours. The reaction solution was concentrated, then ethanol (1.0 mL) and 2 M hydrochloric acid (5.0 mL) were added to the residue, and the mixture was stirred at 100° C. for 3 hours.

After allowing to cool, the reaction solution was neutralized with sodium hydrogencarbonate, and the resulting solid was collected by filtration. The solid thus collected by filtration was purified with silica gel chromatography to yield the title compound (0.060 g, 42%) as a colorless solid.

$^1$H-NMR (500 MHz, DMSO-d$_6$) δ ppm: 1.76-1.84 (1H, m), 2.00-2.19 (4H, m), 2.55-2.59 (1H, m), 3.01-3.05 (1H, m), 4.67 (1H, dt, J=3.9, 9.3 Hz), 6.94 (1H, brs), 7.15 (1H, d, J=12.2 Hz), 7.51 (2H, s), 7.81 (1H, d, J=7.8 Hz), 8.23 (1H, brs), 8.56 (1H, s), 12.88 (1H, brs).

MS (ESI) m/z: 488 [M+H]$^+$.

Example 53

5-Chloro-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide

[Formula 75]

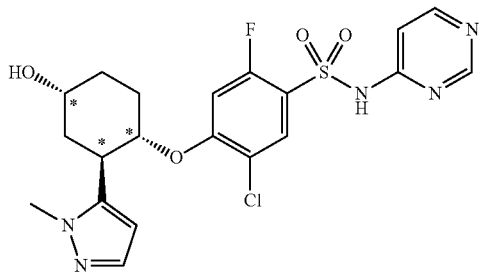

(53a) (1S*,2R*,4R*)-4-{[tert-Butyl(dimethyl)silyl]oxy}-2-(1-methyl-1H-pyrazol-5-yl)cyclohexanol The reaction and aftertreatment were conducted in the same manner as in Example 3a by using 1-methylpyrazole (500 mg, 6.09 mmol), n-butyl lithium (2.69 M solution in hexane; 2.37 mL, 6.37 mmol), tert-butyl(dimethyl)[(1R*,3R*,6S*)-7-oxabicyclo[4.1.0]hept-3-yloxy]silane (J. Pharm. Pharmacol., 49, 835-842, 1997; 1.32 g, 5.78 mmol), and THF (30 mL), to yield the title compound (1.23 g, 69%) as a colorless solid.

$^1$H-NMR (500 MHz, CDCl$_3$) δ ppm: 0.06 (3H, s), 0.07 (3H, s), 0.93 (9H, s), 1.49-1.61 (3H, m), 1.78-1.97 (3H, m), 3.18-3.23 (1H, m), 3.64-3.68 (1H, m), 3.85 (3H, s), 4.05-4.07 (1H, m), 6.07 (1H, d, J=2.0 Hz), 7.44 (1H, d, J=1.5 Hz).

(53b) 4-{[(1S*,2R*,4R*)-4-{[tert-Butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (91.6 mg, 0.201 mmol) prepared in Example 2a, the (1S*,2R*,4R*)-4-{[tert-butyl(dimethyl)silyl]oxy}-2-(1-methyl-1H-pyrazol-5-yl)cyclohexanol (52.0 mg, 0.167 mmol) prepared in Example 53a, sodium hydride (63%; 9.6 mg, 0.252 mmol), and DMF (1.0 mL), to yield the title compound (90.0 mg, 72%) as a colorless oil.

$^1$H-NMR (500 MHz, CDCl$_3$) δ ppm: 0.08 (3H, s), 0.09 (3H, s), 0.94 (9H, s), 1.60-2.09 (6H, m), 3.58-3.63 (1H, m), 3.76 (6H, s), 3.93 (3H, s), 4.13-4.17 (2H, m), 5.21 (2H, s), 5.98 (1H, d, J=2.0 Hz), 6.38-6.41 (2H, m), 6.45 (1H, d, J=11.7 Hz), 7.21 (1H, d, J=9.3 Hz), 7.23 (1H, dd, J=1.0, 5.9 Hz), 7.34 (1H, d, J=1.5 Hz), 7.92 (1H, d, J=7.8 Hz), 8.46 (1H, d, J=5.9 Hz), 8.79 (1H, d, J=1.0 Hz).

(53c) 5-Chloro-N-(2,4-dimethoxybenzyl)-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide A solution of the 4-{[(1S*,2R*,4R*)-4-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (90.0 mg, 0.120 mmol) prepared in Example 53b and tetrabutyl ammonium fluoride (1.0 M solution in THF; 0.241 mL, 0.241 mmol) in THF (5.0 mL) was stirred at room temperature for 3 hours. To the reaction solution, 1 M hydrochloric acid (10 mL) was added, followed by extraction with ethyl acetate (100 mL). The thus obtained organic layer was dried over anhydrous sodium sulfate. After concentration under reduced pressure, the residue was purified with silica gel chromatography to yield the title compound (65.3 mg, 86%) as a colorless solid.

$^1$H-NMR (500 MHz, CDCl$_3$) δ ppm: 1.83-2.17 (6H, m), 3.59-3.65 (1H, m), 3.76 (6H, s), 3.95 (3H, s), 4.14-4.19 (1H, m), 4.23-4.26 (1H, m), 5.21 (2H, s), 6.02 (1H, d, J=2.0 Hz), 6.38-6.40 (2H, m), 6.43 (1H, d, J=11.7 Hz), 7.18 (1H, d, J=9.3 Hz), 7.22 (1H, dd, J=1.0, 5.9 Hz), 7.35 (1H, d, J=2.0 Hz), 7.93 (1H, d, J=7.8 Hz), 8.46 (1H, d, J=5.9 Hz), 8.79 (1H, s).

(53d) 5-Chloro-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the 5-chloro-N-(2, 4-dimethoxybenzyl)-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide (65.3 mg, 0.103 mmol) prepared in Example 53c, triethylsilane (0.050 mL), trifluoroacetic acid (0.50 mL), and dichloromethane (1.0 mL), to yield the title compound (32.6 mg, 71%) as a colorless solid.

$^1$H-NMR (500 MHz, CD$_3$OD) δ ppm: 1.77-2.04 (6H, m), 3.56-3.61 (1H, m), 3.90 (3H, s), 4.10-4.13 (1H, m), 4.51-4.56 (1H, m), 6.15 (1H, d, J=2.0 Hz), 6.97 (1H, d, J=12.2 Hz), 7.00 (1H, d, J=6.4 Hz), 7.26 (1H, d, J=2.0 Hz), 7.90 (1H, d, J=7.3 Hz), 8.25 (1H, d, J=6.4 Hz), 8.53 (1H, s).

MS (ESI) m/z: 482 [M+H]$^+$.

Example 54

4-{[(1S*,2R*)-5,5-Difluoro-2-(1H-pyrazol-5-yl)cyclohexyl]oxy}-2-fluoro-5-methyl-N-(pyrimidin-4-yl)benzenesulfonamide

[Formula 76]

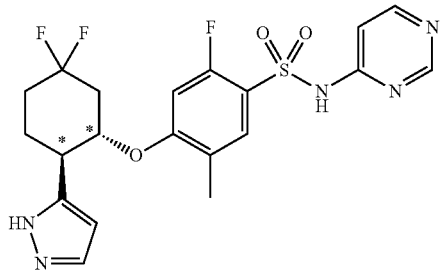

(54a) 1-[(2-Methoxyethoxy)methyl]-1H-pyrazole

To a solution of 1H-pyrazole (13.6 g, 200 mmol) and N,N-diisopropylethylamine (68 mL, 400 mmol) in dichloromethane (150 mL), 2-methoxyethoxymethyl chloride (24.9 mL, 220 mmol) was added with cooling on ice. The reaction solution was stirred at room temperature for 2 hours, and an aqueous sodium hydrogencarbonate solution (500 mL) was then added to the reaction solution, followed by extraction three times with dichloromethane (500 mL). The organic layer was dried over anhydrous sodium sulfate. After concentration under reduced pressure, the residue was purified with silica gel chromatography (hexane/ethyl acetate=1:1) to yield the title compound (29.9 g, 96%) as a colorless oil.

$^1$H-NMR (500 MHz, CDCl$_3$) δ ppm: 3.36 (3H, s), 3.48-3.50 (2H, m), 3.63-3.64 (2H, m), 5.52 (2H, s), 6.35 (1H, t, J=2.0 Hz), 7.56 (1H, d, J=1.0 Hz), 7.60 (1H, d, J=2.4 Hz).

(54b) (1S*,2R*,5R*)-5-(Benzyloxy)-2-{1-[(2-methoxyethoxy)methyl]-1H-pyrazol-5-yl}cyclohexanol To a solution of the 1-[(2-methoxyethoxy)methyl]-1H-pyrazole (3.13 g, 20.1 mmol) prepared in Example 54a in THF (30 mL), butyl lithium (2.69 M solution in hexane; 7.46 mL, 20.1 mmol) and a boron trifluoride-diethyl ether complex (6.30 mL, 50.1 mmol) were added in this order at −78° C. The reaction solution was stirred at −78° C. for 10 minutes. Then, (1S*,3R*,6R*)-3-(benzyloxy)-7-oxabicyclo[4.1.0]heptane (J. Chem. Soc. Perkin Trans. 1 1997, 657; 3.41 g, 16.7 mmol) was added thereto, and the mixture was stirred at −78° C. for 5 hours. To the reaction solution, an aqueous sodium hydrogencarbonate solution (100 mL) was added, followed by extraction three times with ethyl acetate (100 mL). The thus obtained organic layer was dried over anhydrous sodium sulfate. After concentration under reduced pressure, the residue was purified with silica gel chromatography (ethyl acetate) to yield the title compound (3.00 g, 55%) as a mixture (3.00 g, 55%) with (1S*,2R*,4S*)-4-(benzyloxy)-2-{1-[(2-methoxyethoxy)methyl]-1H-pyrazol-5-yl}cyclohexanol.

(54c) (1S*,2R*,5R*)-5-(Benzyloxy)-2-{1-[(2-methoxyethoxy)methyl]-1H-pyrazol-5-yl}cyclohexyl benzoate To a solution of the mixture (2.99 g, 8.30 mmol) of (1S*,2R*,5R*)-5-(benzyloxy)-2-{1-[(2-methoxyethoxy)methyl]-1H-pyrazol-5-yl}cyclohexanol and (1S*,2R*,4S*)-4-(benzyloxy)-2-{1-[(2-methoxyethoxy)methyl]-1H-pyrazol-5-yl}cyclohexanol prepared in Example 54b, triethylamine (4.62 mL, 33.2 mmol) and 4-(N,N-dimethylamino)pyridine (203 mg, 1.66 mmol) in dichloroethane (30 mL), benzoyl chloride (1.93 mL, 16.6 mmol) was added, and the reaction solution was stirred for 5 hours under heated reflux. To the reaction solution, water (100 mL) was added, and an organic layer was extracted and then dried over anhydrous sodium sulfate. After concentration under reduced pressure, the residue was purified with column chromatography (hexane/ethyl acetate=1:9) to yield the title compound (2.72 g, 71%) as a mixture (2.72 g, 71%) with (1R*,2R*,4S*)-4-(benzyloxy)-2-{1-[(2-methoxyethoxy)methyl]-1H-pyrazol-5-yl}cyclohexyl benzoate.

(54d) (1S*,2R*,5R*)-5-Hydroxy-2-{1-[(2-methoxyethoxy)methyl]-1H-pyrazol-5-yl}cyclohexyl benzoate A solution of the mixture (2.72 g, 5.84 mmol) of (1S*,2R*,5R*)-5-(benzyloxy)-2-{1-[(2-methoxyethoxy)methyl]-1H-pyrazol-5-yl}cyclohexyl benzoate and (1R*,2R*,4S*)-4-(benzyloxy)-2-{1-[(2-methoxyethoxy)methyl]-1H-pyrazol-5-yl}cyclohexyl benzoate prepared in Example 54c and palladium carbon (5%; 3.00 g) in ethanol (20 mL) was stirred under a hydrogen atmosphere at 50° C. for 11 hours. The reaction solution was filtered using Celite, and the residue was purified with silica gel chromatography (ethyl acetate) to yield the title compound (1.06 g, 48%) as a colorless oil.

$^1$H-NMR (500 MHz, CDCl$_3$) δ ppm: 1.69-1.80 (2H, m), 1.90-1.97 (2H, m), 2.06-2.13 (1H, m), 2.34-2.39 (1H, m), 3.26-3.31 (1H, m), 3.37 (3H, s), 3.42-3.51 (2H, m), 3.55-3.65 (2H, m), 4.36 (1H, s), 5.45 (1H, d, J=11.7 Hz), 5.59 (1H, dt, J=4.4, 10.7 Hz), 5.77 (1H, d, J=11.2 Hz), 6.24 (1H, d, J=2.0 Hz), 7.35-7.38 (3H, m), 7.51 (1H, t, J=7.3 Hz), 7.82-7.84 (2H, m).

Also, a by-product (1S*,2R*,4S*)-4-hydroxy-2-{1-[(2-methoxyethoxy)methyl]-1H-pyrazol-5-yl}cyclohexyl benzoate (825 mg, 38%) was obtained as a colorless oil.

$^1$H-NMR (500 MHz, CDCl$_3$) δ ppm: 1.56-1.68 (3H, m), 2.12-2.35 (3H, m), 3.34-3.38 (1H, m), 3.38 (3H, s), 3.42-3.51 (2H, m), 3.53-3.64 (2H, m), 3.86-3.92 (1H, m), 5.16 (1H, dt, J=4.4, 10.3 Hz), 5.42 (1H, d, J=11.2 Hz), 5.76 (1H, d, J=11.2 Hz), 6.20 (1H, d, J=2.0 Hz), 7.35-7.38 (3H, m), 7.51 (1H, t, J=7.3 Hz), 7.81-7.82 (2H, m).

(54e) (1S*,2R*)-2-{1-[(2-Methoxyethoxy)methyl]-1H-pyrazol-5-yl}-5-oxocyclohexyl benzoate The reaction and aftertreatment were conducted in the same manner as in Example 31d by using the (1S*,2R*,5R*)-5-hydroxy-2-{1-[(2-methoxyethoxy)methyl]-1H-pyrazol-5-yl}cyclohexyl benzoate (1.06 g, 2.83 mmol) prepared in Example 54d, Dess-Martin reagent (1.80 g, 4.25 mmol) and dichloromethane (40 mL), to yield the title compound (945 mg, 90%) as a colorless oil.

$^1$H-NMR (500 MHz, CDCl$_3$) δ ppm: 1.89-1.98 (1H, m), 2.36-2.67 (4H, m), 3.04 (1H, ddd, J=1.5, 4.9, 14.6 Hz), 3.36 (3H, s), 3.43-3.53 (2H, m), 3.57-3.71 (3H, m), 5.48-5.53 (1H, m), 5.52 (1H, d, J=11.2 Hz), 5.82 (1H, d, J=11.2 Hz), 6.24 (1H, d, J=1.5 Hz), 7.38-7.43 (3H, m), 7.54 (1H, t, J=7.3 Hz), 7.85-7.87 (2H, m).

(54f) (1S*,2R*)-5,5-Difluoro-2-{1-[(2-methoxyethoxy)methyl]-1H-pyrazol-5-yl}cyclohexyl benzoate The reaction and aftertreatment were conducted in the same manner as in Example 31e by using the (1S*,2R*)-2-{1-[(2-methoxyethoxy)methyl]-1H-pyrazol-5-yl}-5-oxocyclohexyl benzoate (940 mg, 2.52 mmol) prepared in Example 54e, bis(2-methoxyethyl)amino sulfur trifluoride (2.66 mL, 15.1 mmol) and dichloromethane (10 mL), to yield the title compound (465 mg, 43%) as a colorless oil.

$^1$H-NMR (500 MHz, CDCl$_3$) δ ppm: 1.80-2.29 (5H, m), 2.74-2.81 (1H, m), 3.31-3.34 (1H, m), 3.36 (3H, s), 3.40-3.51 (2H, m), 3.53-3.65 (2H, m), 5.41 (1H, dt, J=4.4, 10.7 Hz), 5.44 (1H, d, J=11.7 Hz), 5.76 (1H, d, J=11.2 Hz), 6.21 (1H, d, J=2.0 Hz), 7.36-7.39 (3H, m), 7.53 (1H, t, J=7.8 Hz), 7.81-7.83 (2H, m).

(54g) (1S*,2R*)-5,5-Difluoro-2-{1-[(2-methoxyethoxy)methyl]-1H-pyrazol-5-yl}cyclohexanol The reaction and aftertreatment were conducted in the same manner as in Example 31f by using the (1S*,2R*)-5,5-difluoro-2-{1-[(2-methoxyethoxy)methyl]-1H-pyrazol-5-yl}cyclohexyl benzoate (463 mg, 1.17 mmol) prepared in Example 54f, potassium carbonate (16 mg, 0.117 mmol) and methanol (10 mL), to yield the title compound (307 mg, 90%) as a colorless oil.

$^1$H-NMR (500 MHz, CDCl$_3$) δ ppm: 1.71-1.99 (4H, m), 2.15-2.21 (1H, m), 2.56-2.63 (1H, m), 2.73-2.79 (1H, m), 2.87-2.92 (1H, m), 3.30 (3H, s), 3.44-3.46 (2H, m), 3.59-3.68 (2H, m), 3.85-3.91 (1H, m), 5.53 (1H, d, J=11.2 Hz), 5.65 (1H, d, J=11.2 Hz), 6.22 (1H, d, J=2.0 Hz), 7.50 (1H, d, J=1.5 Hz).

(54h) 4-{[(1S*,2R*)-5,5-Difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (261 mg, 0.60 mmol) prepared in Example 10a, the (1S*,2R*)-5,5-difluoro-2-{1-[(2-methoxyethoxy)methyl]-1H-pyrazol-5-yl}cyclohexanol (145 mg, 0.50 mmol) prepared in Example 54g, sodium hydride (63%; 29.0 mg, 0.75 mmol), DMF (8.0 mL) and water (0.016 mL), to yield the title compound (280 mg, 79%) as a colorless amorphous solid.

$^1$H-NMR (500 MHz, CDCl$_3$) δ ppm: 1.84-2.04 (3H, m), 1.98 (3H, s), 2.12-2.18 (1H, m), 16.31 (1H, m), 2.68-2.74 (1H, m), 3.35 (3H, s), 3.39-3.45 (2H, m), 3.47-3.55 (2H, m), 3.65-3.69 (1H, m), 3.76 (3H, s), 3.78 (3H, s), 4.41 (1H, dt, J=3.9, 10.3 Hz), 5.23 (2H, s), 5.44 (1H, d, J=11.2 Hz), 5.83 (1H, d, J=11.7 Hz), 6.10 (1H, d, J=1.5 Hz), 6.38-6.44 (3H, m), 7.19 (1H, d, J=8.8 Hz), 7.25 (1H, dd, J=1.5, 5.9 Hz), 7.41 (1H, d, J=2.0 Hz), 7.68 (1H, d, J=7.3 Hz), 8.43 (1H, d, J=5.9 Hz), 8.76 (1H, s).

(54i) 4-{[(1S*,2R*)-5,5-Difluoro-2-(1H-pyrazol-5-yl)cyclohexyl]oxy}-2-fluoro-5-methyl-N-(pyrimidin-4-yl)benzenesulfonamide To a solution of the 4-{[(1S*,2R*)-5,5-difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide (265 mg, 0.376 mmol) prepared in Example 54h and triethylsilane (0.50 mL) in dichloroethane (5.0 mL), trifluoroacetic acid (5.0 mL) was added at room temperature, and the reaction solution was stirred for 4 hours. The reaction solution was concentrated, then methanol (15 mL) and 6 M hydrochloric acid (5.0 mL) were added to the residue, and the reaction solution was stirred for 5 hours under heated reflux. To the reaction solution, an aqueous sodium hydrogencarbonate solution (50 mL) was added, followed by extraction five times with a dichloromethane/methanol; 10:1 mixed solvent (50 mL). The thus obtained organic layer was dried over anhydrous sodium sulfate. After concentration under reduced pressure, the residue was purified with silica gel chromatography (dichloromethane/methanol=10:1) to yield the title compound (125 mg, 71%) as a colorless solid.

$^1$H-NMR (500 MHz, DMSO-d$_6$) δ ppm: 1.78-1.86 (1H, m), 2.00-2.23 (4H, m), 2.00 (3H, s), 2.55-2.63 (1H, m), 3.15-3.20 (1H, m), 3.74-3.78 (1H, m), 6.15 (1H, d, J=2.0 Hz), 6.88 (1H, d, J=12.2 Hz), 7.00 (1H, brs), 7.47 (1H, brs), 7.62 (1H, d, J=8.3 Hz), 8.31 (1H, brs), 8.57 (1H, brs), 12.60 (1H, brs).

MS (ESI) m/z: 468 [M+H]$^+$.

Example 55

5-Chloro-4-{[(1S*,2R*)-5,5-difluoro-2-(1H-pyrazol-5-yl)cyclohexyl]oxy}-2-fluoro-N-(pyrimidin-4-yl)benzenesulfonamide

[Formula 77]

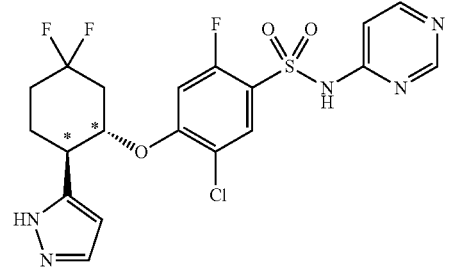

(55a) 5-Chloro-4-{[(1S*,2R*)-5,5-difluoro-2-{1-[(2-methoxyethoxy)methyl]-1H-pyrazol-5-yl}cyclohexyl]oxy}-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (129 mg, 0.283 mmol) prepared in Example 2a, the (1S*,2R*)-5,5-difluoro-2-{1-[(2-methoxyethoxy)methyl]-1H-pyrazol-5-yl}cyclohexanol (68 mg, 0.236 mmol) prepared in Example 54g, sodium hydride (63%; 13.0 mg, 0.354 mmol), DMF (5.0 mL) and water (0.008 mL), to yield the title compound (105 mg, 61%) as a colorless amorphous solid.

$^1$H-NMR (500 MHz, CDCl$_3$) δ ppm: 1.87-2.16 (4H, m), 2.26-2.32 (1H, m), 2.66-2.70 (1H, m), 3.35 (3H, s), 3.40-3.53 (4H, m), 3.65-3.69 (1H, m), 3.76 (6H, s), 4.39 (1H, dt, J=4.4, 10.7 Hz), 5.20 (2H, s), 5.41 (1H, d, J=11.2 Hz), 6.02 (1H, d, J=11.2 Hz), 6.14 (1H, d, J=2.0 Hz), 6.38-6.40 (2H, m), 6.49 (1H, d, J=11.2 Hz), 7.19 (2H, d, J=8.3 Hz), 7.40 (1H, d, J=2.0 Hz), 7.94 (1H, d, J=7.3 Hz), 8.47 (1H, d, J=5.4 Hz), 8.79 (1H, s).

(55b) 5-Chloro-4-{[(1S*,2R*)-5,5-difluoro-2-(1H-pyrazol-5-yl)cyclohexyl]oxy}-2-fluoro-N-(pyrimidin-4-yl)benzenesulfonamide The reaction and aftertreatment were conducted in the same manner as in Example 54i by using the 5-chloro-4-{[(1S*,2R*)-5,5-difluoro-2-{1-[(2-methoxyethoxy)methyl]-1H-pyrazol-5-yl}cyclohexyl]oxy}-N-(2,4-dimethoxybenzyl)-2-fluoro-N-(pyrimidin-4-yl)benzenesulfonamide (105 mg, 0.145 mmol) prepared in Example 55a, triethylsilane (0.30 mL), trifluoroacetic acid (3.0 mL), dichloromethane (3.0 mL), 6 M hydrochloric acid (5.0 mL) and methanol (15 mL), to yield the title compound (29 mg, 41%) as a colorless solid.

$^1$H-NMR (500 MHz, DMSO-d$_6$) δ ppm: 1.80-1.87 (1H, m), 1.99-2.28 (4H, m), 2.55-2.64 (1H, m), 3.18-3.22 (1H, m), 4.86-4.91 (1H, m), 6.18 (1H, d, J=2.0 Hz), 6.95 (1H, brs), 7.13 (1H, d, J=11.7 Hz), 7.47 (1H, brs), 7.79 (1H, d, J=7.3 Hz), 8.24 (1H, brs), 8.56 (1H, brs), 12.51 (1H, brs).
MS (ESI) m/z: 488 [M+H]$^+$.

Example 56

4-{[(1S*,2R*)-4,4-Difluoro-2-(1H-pyrazol-5-yl)cyclohexyl]oxy}-2-fluoro-5-methyl-N-(pyrimidin-4-yl)benzenesulfonamide

[Formula 78]

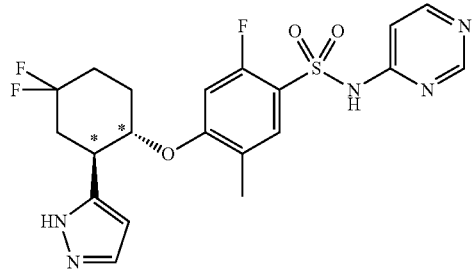

(56a) (1S*,2R*)-2-{1-[(2-Methoxyethoxy)methyl]-1H-pyrazol-5-yl}-4-oxocyclohexyl benzoate The reaction and aftertreatment were conducted in the same manner as in Example 31d by using the by-product (1S*,2R*,4S*)-4-hydroxy-2-{1-[(2-methoxyethoxy)methyl]-1H-pyrazol-5-yl}cyclohexyl benzoate (825 mg, 2.20 mmol) of Example 54d, Dess-Martin reagent (1.40 g, 3.31 mmol) and dichloromethane (10 mL), to yield the title compound (688 mg, 83%) as a colorless oil.

$^1$H-NMR (500 MHz, CDCl$_3$) δ ppm: 2.09-2.17 (1H, m), 16.32 (1H, m), 2.54-2.66 (2H, m), 2.71-2.77 (1H, m), 2.94 (1H, dd, J=5.9, 15.1 Hz), 3.33 (3H, s), 3.43-3.50 (2H, m), 3.58-3.69 (2H, m), 3.95 (1H, q, J=6.4 Hz), 5.54 (1H, d, J=11.2 Hz), 5.55-5.58 (1H, m), 5.79 (1H, d, J=11.2 Hz), 6.20 (1H, d, J=1.5 Hz), 7.44-7.47 (3H, m), 7.59 (1H, t, J=7.3 Hz), 7.97-7.99 (2H, m).

(56b) (1S*,2R*)-4,4-Difluoro-2-{1-[(2-methoxyethoxy)methyl]-1H-pyrazol-5-yl}cyclohexyl benzoate The reaction and aftertreatment were conducted in the same manner as in Example 31e by using the (1S*,2R*)-2-{1-[(2-methoxyethoxy)methyl]-1H-pyrazol-5-yl}-4-oxocyclohexyl benzoate (686 mg, 1.84 mmol) prepared in Example 56a, bis(2-methoxyethyl)amino sulfur trifluoride (1.94 mL, 11.1 mmol) and dichloromethane (10 mL), to yield the title compound (547 mg, 75%) as a colorless oil.

$^1$H-NMR (500 MHz, CDCl$_3$) δ ppm: 1.87-2.13 (3H, m), 16.32 (2H, m), 2.51-2.57 (1H, m), 3.37 (3H, s), 3.47-3.56 (3H, m), 3.60-3.68 (2H, m), 5.26 (1H, dt, J=3.4, 10.7 Hz), 5.44 (1H, d, J=11.2 Hz), 5.75 (1H, d, J=11.2 Hz), 6.21 (1H, d, J=2.0 Hz), 7.36-7.39 (3H, m), 7.53 (1H, t, J=7.3 Hz), 7.82-7.84 (2H, m).

(56c) (1S*,2R*)-4,4-Difluoro-2-{1-[(2-methoxyethoxy)methyl]-1H-pyrazol-5-yl}cyclohexanol The reaction and aftertreatment were conducted in the same manner as in Example 31f by using the (1S*,2R*)-4,4-difluoro-2-{1-[(2-methoxyethoxy)methyl]-1H-pyrazol-5-yl}cyclohexyl benzoate (547 mg, 1.39 mmol) prepared in Example 56b, potassium carbonate (19 mg, 0.139 mmol) and methanol (10 mL), to yield the title compound (404 mg, 99%) as a yellow oil.

$^1$H-NMR (500 MHz, CDCl$_3$) δ ppm: 1.75-1.81 (1H, m), 1.85-2.03 (2H, m), 2.12-2.26 (2H, m), 2.31-2.38 (1H, m), 3.18-3.24 (1H, m), 3.31 (3H, s), 3.43-3.51 (2H, m), 3.60-3.73 (3H, m), 5.53 (1H, d, J=10.7 Hz), 5.61 (1H, d, J=11.2 Hz), 6.22 (1H, s), 7.51 (1H, s).

(56d) 4-{[(1S*,2R*)-4,4-Difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (785 mg, 1.81 mmol) prepared in Example 10a, the (1S*,2R*)-4,4-difluoro-2-{1-[(2-methoxyethoxy)methyl]-1H-pyrazol-5-yl}cyclohexanol (404 mg, 1.39 mmol) prepared in Example 56c, sodium hydride (63%; 79.0 mg, 2.08 mmol), DMF (6.0 mL) and water (0.045 mL), to yield the title compound (358 mg, 36%) as a colorless amorphous solid.

$^1$H-NMR (500 MHz, CDCl$_3$) δ ppm: 1.82-2.14 (3H, m), 2.00 (3H, s), 2.29 (2H, m), 2.47-2.56 (1H, m), 3.36 (3H, s), 3.44-3.54 (2H, m), 3.64-3.73 (3H, m), 3.75 (3H, s), 3.78 (3H, s), 4.32 (1H, dt, J=3.4, 10.3 Hz), 5.24 (2H, s), 5.44 (1H, d, J=11.2 Hz), 5.81 (1H, d, J=11.2 Hz), 6.13 (1H, d, J=2.0 Hz), 6.38-6.44 (3H, m), 7.18 (1H, d, J=7.8 Hz), 7.27 (1H, d, J=6.4 Hz), 7.42 (1H, d, J=2.0 Hz), 7.68 (1H, d, J=7.8 Hz), 8.43 (1H, d, J=5.9 Hz), 8.76 (1H, s).

(56e) 4-{[(1S*,2R*)-4,4-Difluoro-2-(1H-pyrazol-5-yl)cyclohexyl]oxy}-2-fluoro-5-methyl-N-(pyrimidin-4-yl)benzenesulfonamide The reaction and aftertreatment were conducted in the same manner as in Example 54i by using the 4-{[(1S*,2R*)-4,4-difluoro-2-{1-[(2-methoxyethoxy)methyl]-1H-pyrazol-5-yl}cyclohexyl]oxy}-N-(2,4-dimethoxybenzyl)-2-fluoro-5-methyl-N-(pyrimidin-4-yl)benzenesulfonamide (356 mg, 0.504 mmol) prepared in Example 56d, triethylsilane (0.50 mL), trifluoroacetic acid (5.0 mL), dichloromethane (5.0 mL), 6 M hydrochloric acid (5.0 mL) and methanol (15 mL), to yield the title compound (155 mg, 66%) as a colorless solid.

$^1$H-NMR (500 MHz, DMSO-d$_6$) δ ppm: 1.60-1.67 (1H, m), 1.98 (3H, s), 2.10-2.36 (5H, m), 3.20-3.26 (1H, m), 4.69-4.74 (1H, m), 6.11 (1H, d, J=2.0 Hz), 7.00-7.02 (2H, m), 7.45 (1H, brs), 7.59 (1H, d, J=7.8 Hz), 8.35 (1H, brs), 8.58 (1H, brs), 12.59 (1H, brs).

MS (ESI) m/z: 468 [M+H]$^+$.

Example 57

5-Chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide

[Formula 79]

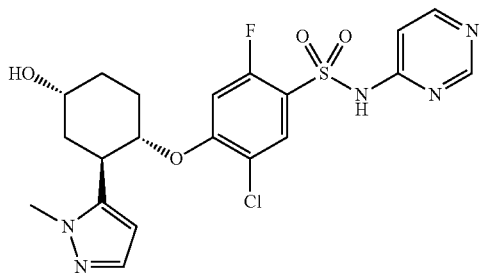

(57a) (1S,2R,4R)-4-{[Tert-butyl(dimethyl)silyl]oxy}-2-(1-methyl-1H-pyrazol-5-yl)cyclohexanol The (1S*,2R*,4R*)-4-{[tert-butyl(dimethyl)silyl]oxy}-2-(1-methyl-1H-pyrazol-5-yl)cyclohexanol prepared in Example 53a was optically resolved with CHIRALFLASH IC (Daicel Corp.; hexane/isopropanol=6:4) to yield the title compound as a colorless oil.

(57b) 4-{[(1S,2R,4R)-4-{[Tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (238 mg, 0.522 mmol) prepared in Example 2a, the (1S,2R,4R)-4-{[tert-butyl(dimethyl)silyl]oxy}-2-(1-methyl-1H-pyrazol-5-yl)cyclohexanol (135 mg, 0.434 mmol) prepared in Example 57a, sodium hydride (63%; 24.8 mg, 0.651 mmol) and DMF (2.0 mL), to yield the title compound (262 mg, 81%) as a colorless oil.

(57c) 5-Chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 53c by using the 4-{[(1S,2R,4R)-4-{[tert-butyl(dimethyl)silyl]oxy}-2-(1-methyl-1H-pyrazol-5-yl)cyclohexyl]oxy}-5-chloro-N-(2,4-dimethoxybenzyl)-2-fluoro-N-(pyrimidin-4-yl)benzenesulfonamide (262 mg, 0.351 mmol) prepared in Example 57b, tetrabutyl ammonium fluoride (1.0 M solution in THF; 0.702 mL, 0.702 mmol) and THF (5.0 mL), to yield the title compound (153 mg, 69%) as a colorless amorphous solid.

(57d) 5-Chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide (153 mg, 0.242 mmol) prepared in Example 57c, triethylsilane (0.050 mL), trifluoroacetic acid (0.50 mL) and dichloromethane (1.0 mL), to yield the title compound (92.0 mg, 79%) as a colorless solid.

[α]$_D^{25}$=9.62 (c 0.915, DMSO).

Example 58

(1R,3R,4S)-4-[2-Chloro-5-fluoro-4-(pyrimidin-4-ylsulfamoyl)phenoxy]-3-(1-methyl-1H-pyrazol-5-yl)cyclohexyl acetate

[Formula 80]

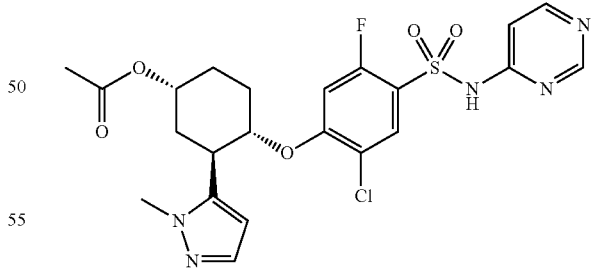

A solution of the 5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide (22.0 mg, 0.046 mmol) prepared in Example 57d, acetic anhydride (0.50 mL) and 4-(N,N-dimethylamino)pyridine (0.6 mg, 0.0046 mmol) in pyridine (1.0 mL) was stirred at room temperature for 3 hours. The reaction solution was concentrated, and 1 M HCl (10 mL) was then added to the residue, followed by extraction with dichloromethane (50 mL). The thus obtained organic layer was dried over anhydrous sodium sulfate. After concentration under reduced pressure, the residue was purified with silica gel chromatography (dichloromethane/methanol=10:1) to yield the title compound (22.0 mg, 91%) as a colorless solid.

$^1$H-NMR (500 MHz, CDCl$_3$) δ ppm: 1.68-1.75 (1H, m), 1.88-1.97 (2H, m), 2.05-2.15 (2H, m), 2.15 (3H, s), 2.22-2.27 (1H, m), 3.40-3.45 (1H, m), 3.94 (3H, s), 4.19 (1H, dt, J=3.9, 10.3 Hz), 5.18-5.19 (1H, m), 6.04 (1H, d, J=2.0 Hz), 6.45 (1H, d, J=11.2 Hz), 7.26-7.27 (1H, m), 7.35 (1H, d, J=2.0 Hz), 7.96 (1H, d, J=7.3 Hz), 8.39 (1H, d, J=6.4 Hz), 8.82 (1H, s).

MS (ESI) m/z: 524 [M+H]$^+$.

Example 59

5-Chloro-2-fluoro-4-{[(1S,2R)-2-(1H-pyrazol-5-yl)cyclohexyl]oxy}-N-(pyrimidin-4-yl)benzenesulfonamide

[Formula 81]

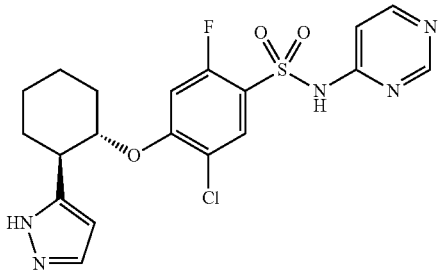

(59a) (1S*,2R*)-2-{1-[(2-Methoxyethoxy)methyl]-1H-pyrazol-5-yl}cyclohexanol

The reaction and aftertreatment were conducted in the same manner as in Example 54b by using the 1-[(2-methoxyethoxy)methyl]-1H-pyrazole (2.00 g, 12.8 mmol) prepared in Example 54a, butyl lithium (2.69 M solution in hexane; 4.76 mL, 12.8 mmol), a boron trifluoride-diethyl ether complex (2.68 mL, 21.3 mmol), cyclohexene oxide (1.05 g, 10.7 mmol) and THF (100 mL), to yield the title compound (1.64 g, 60%) as a colorless oil.

$^1$H-NMR (500 MHz, CDCl$_3$) δ ppm: 1.30-1.48 (4H, m), 1.73-2.13 (3H, m), 2.11-2.13 (1H, m), 2.77-2.82 (1H, m), 3.32 (3H, s), 3.45-3.47 (2H, m), 3.57-3.68 (4H, m), 5.52 (1H, d, J=12.2 Hz), 5.64 (1H, d, J=11.2 Hz), 6.18 (1H, d, J=2.0 Hz), 7.48 (1H, d, J=1.0 Hz).

(59b) (1S,2R)-2-{1-[(2-Methoxyethoxy)methyl]-1H-pyrazol-5-yl}cyclohexanol

The (1S*,2R*)-2-{1-[(2-methoxyethoxy)methyl]-1H-pyrazol-5-yl}cyclohexanol prepared in Example 59a was optically resolved with CHIRALFLASH IC (Daicel Corp.; hexane/isopropanol=1:1) to yield the title compound as a colorless oil.

(59c) 5-Chloro-N-(2,4-dimethoxybenzyl)-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide The reaction and aftertreatment were conducted in the same manner as in Example 1d by using the 5-chloro-N-(2,4-dimethoxybenzyl)-2,4-difluoro-N-(pyrimidin-4-yl)benzenesulfonamide (280 mg, 0.614 mmol) prepared in Example 2a, the (1S,2R)-2-{1-[(2-methoxyethoxy)methyl]-1H-pyrazol-5-yl}cyclohexanol (104 mg, 0.409 mmol) prepared in Example 59b, sodium hydride (63%; 18.7 mg, 0.491 mmol) and DMF (2.0 mL), to yield the title compound (242 mg, 86%) as a colorless amorphous solid.

$^1$H-NMR (400 MHz, CDCl$_3$) δ ppm: 1.43-1.69 (4H, m), 1.84-1.95 (2H, m), 2.08-2.21 (2H, m), 3.36 (3H, s), 3.43-3.55 (4H, m), 3.65-3.70 (1H, m), 3.76 (6H, s), 4.17 (1H, dt, J=3.9, 10.2 Hz), 5.21 (2H, s), 5.40 (1H, d, J=11.3 Hz), 6.05 (1H, d, J=11.3 Hz), 6.10 (1H, d, J=2.0 Hz), 6.37-6.40 (2H, m), 6.49 (1H, d, J=11.7 Hz), 7.16-7.19 (1H, m), 7.22 (1H, dd, J=1.6, 6.3 Hz), 7.38 (1H, d, J=1.6 Hz), 7.91 (1H, d, J=7.4 Hz), 8.46 (1H, d, J=5.9 Hz), 8.79 (1H, d, J=0.8 Hz).

(59d) 5-Chloro-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide The reaction and aftertreatment were conducted in the same manner as in Example 1e by using the 5-chloro-N-(2,4-dimethoxybenzyl)-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide (154 mg, 0.223 mmol) prepared in Example 59c, triethylsilane (0.20 mL), trifluoroacetic acid (1.0 mL) and dichloromethane (2.0 mL), to yield the title compound (120 mg, 99%) as a colorless oil.

$^1$H-NMR (500 MHz, CDCl$_3$) δ ppm: 1.43-1.67 (4H, m), 1.85-1.94 (2H, m), 2.08-2.21 (2H, m), 3.36 (3H, s), 3.42-3.45 (4H, m), 3.64-3.69 (1H, m), 4.17 (1H, dt, J=3.9, 10.3 Hz), 5.38 (1H, d, J=11.2 Hz), 6.04 (1H, d, J=11.7 Hz), 6.11 (1H, s), 6.54 (1H, d, J=11.2 Hz), 7.25 (1H, d, J=6.4 Hz), 7.37 (1H, s), 7.93 (1H, dd, J=2.0, 7.3 Hz), 8.37-8.39 (1H, m), 8.80 (1H, s).

(59e) 5-Chloro-2-fluoro-4-{[(1S,2R)-2-(1H-pyrazol-5-yl)cyclohexyl]oxy}-N-(pyrimidin-4-yl)benzenesulfonamide A solution of the 5-chloro-2-fluoro-4-{[(1S,2R)-2-{1-[(2-methoxyethoxy)methyl]-1H-pyrazol-5-yl}cyclohexyl]oxy}-N-(pyrimidin-4-yl)benzenesulfonamide (120 mg, 0.222 mmol) prepared in Example 59d in 6 M HCl (5.0 mL) and methanol (4.0 mL) was heated under reflux with stirring for 5 hours. The reaction solution was concentrated, and the residue was purified with silica gel chromatography (dichloromethane/methanol=85:15) to yield the title compound (80.0 mg, 80%) as a pale yellow solid.

$^1$H-NMR (500 MHz, CD$_3$OD) δ ppm: 1.43-1.65 (3H, m), 1.74-1.93 (3H, m), 2.07-2.09 (1H, m), 2.27-2.29 (1H, m), 3.14-3.19 (1H, m), 4.61 (1H, dt, J=3.9, 10.3 Hz), 6.52 (1H, d, J=2.4 Hz), 7.06 (1H, d, J=12.2 Hz), 7.13 (1H, d, J=6.4 Hz), 7.85 (1H, d, J=2.4 Hz), 7.94 (1H, d, J=7.3 Hz), 8.38 (1H, d, J=6.8 Hz), 8.68 (1H, s).

MS (ESI) m/z: 452 [M+H]$^+$.

$[α]_D^{25}$=2.61 (c 0.998, DMSO).

Example 60

2,6-Difluoro-4-{[(1S,2R)-2-(1H-pyrazol-4-yl)cyclohexyl]oxy}-N-(pyrimidin-4-yl)benzenesulfonamide

[Formula 82]

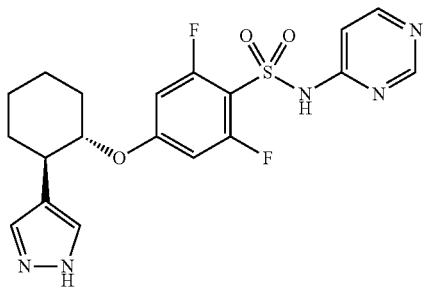

(60a) (1R*,2S*)-2-(1H-Pyrazol-4-yl)cyclohexanol

The reaction and aftertreatment were conducted in the same manner as in Example 54b by using 4-iodo-1H-pyrazole (5.82 g, 30.0 mmol), butyl lithium (2.69 M solution in hexane; 22.3 mL, 60.0 mmol), a boron trifluoride-diethyl ether complex (7.54 mL, 60.0 mmol), cyclohexene oxide (3.24 g, 33.0 mmol) and THF (120 mL), to yield the title compound (0.48 g, 10%) as a colorless solid.
$^1$H-NMR (500 MHz, CDCl$_3$) δ ppm: 1.26-1.51 (4H, m), 1.73-2.11 (4H, m), 2.43-2.48 (1H, m), 3.41-3.46 (1H, m), 7.51 (2H, s).

(60b) (1S,2R)-2-(1H-Pyrazol-4-yl)cyclohexanol

The (1R*,2S*)-2-(1H-pyrazol-4-yl)cyclohexanol prepared in Example 60a was optically resolved with CHIRALPAK AD-H (Daicel Corp.; hexane/ethanol=8:2) to yield the title compound as a colorless solid.

(60c) (1S,2R)-2-[1-(Methoxymethyl)-1H-pyrazol-4-yl]cyclohexanol

To a solution of the (1S,2R)-2-(1H-pyrazol-4-yl)cyclohexanol (144 mg, 0.866 mmol) prepared in Example 60b in DMF (4.0 mL), chloromethyl methyl ether (0.069 mL, 0.908 mmol) was added, and the reaction solution was stirred at room temperature for 2 hours. The reaction solution was concentrated under reduced pressure, and the residue was then purified with silica gel chromatography (hexane/ethyl acetate=7:3) to yield the title compound (132.2 mg, 73%) as a colorless oil.

(60d) N-(2,4-Dimethoxybenzyl)-2,6-difluoro-4-({(1S,2R)-2-[1-(methoxymethyl)-1H-pyrazol-4-yl]cyclohexyl}oxy)-N-(pyrimidin-4-yl)benzenesulfonamide The reaction and aftertreatment were conducted in the same manner as in Example 1d by using the N-(2,4-dimethoxybenzyl)-2,4,6-trifluoro-N-(pyrimidin-4-yl)benzenesulfonamide (156 mg, 0.355 mmol) prepared in Example 4a, the (1S,2R)-2-[1-(methoxymethyl)-1H-pyrazol-4-yl]cyclohexanol (62.2 mg, 0.296 mmol) prepared in Example 60c, sodium hydride (63%; 16.9 mg, 0.444 mmol) and DMF (2.0 mL), to yield the title compound (40.5 mg, 22%) as a colorless oil.

(60e) 2,6-Difluoro-4-{[(1S,2R)-2-(1H-pyrazol-4-yl)cyclohexyl]oxy}-N-(pyrimidin-4-yl)benzenesulfonamide The reaction and aftertreatment were conducted in the same manner as in Example 52b by using the N-(2,4-dimethoxybenzyl)-2,6-difluoro-4-({(1S,2R)-2-[1-(methoxymethyl)-1H-pyrazol-4-yl]cyclohexyl}oxy)-N-(pyrimidin-4-yl)benzenesulfonamide (40.5 mg, 0.0643 mmol) prepared in Example 60d, triethylsilane (0.055 mL), dichloromethane (1.0 mL), trifluoroacetic acid (1.0 mL), methanol (6.0 mL) and 6 M hydrochloric acid (2.0 mL), to yield the title compound (28.0 mg, 99%) as a colorless solid.

Example 61

2-Fluoro-5-methyl-4-{[(1S,2R)-2-(1H-pyrazol-4-yl)cyclohexyl]oxy}-N-(pyrimidin-4-yl)benzenesulfonamide

[Formula 83]

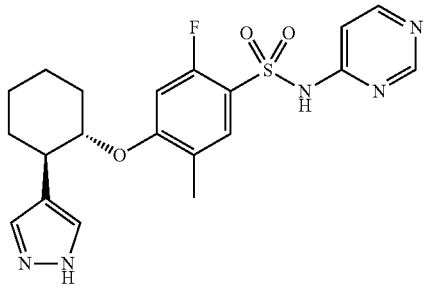

(61a) N-(2,4-Dimethoxybenzyl)-2-fluoro-4-({(1S,2R)-2-[1-(methoxymethyl)-1H-pyrazol-4-yl]cyclohexyl}oxy)-5-methyl-N-(pyrimidin-4-yl)benzenesulfonamide The reaction and aftertreatment were conducted in the same manner as in Example 1d by using the N-(2,4-dimethoxybenzyl)-2,4-difluoro-5-methyl-N-(pyrimidin-4-yl)benzenesulfonamide (174 mg, 0.400 mmol) prepared in Example 10a, the (1S,2R)-2-[1-(methoxymethyl)-1H-pyrazol-4-yl]cyclohexanol (70.0 mg, 0.333 mmol) prepared in Example 60b, sodium hydride (63%; 19.0 mg, 0.499 mmol) and DMF (2.0 mL), to yield the title compound (61.5 mg, 30%) as a colorless oil.

(61b) 2-Fluoro-5-methyl-4-{[(1S,2R)-2-(1H-pyrazol-4-yl)cyclohexyl]oxy}-N-(pyrimidin-4-yl)benzenesulfonamide The reaction and aftertreatment were conducted in the same manner as in Example 52b by using the N-(2,4-dimethoxybenzyl)-2-fluoro-4-({(1S,2R)-2-[1-(methoxymethyl)-1H-pyrazol-4-yl]cyclohexyl}oxy)-5-methyl-N-(pyrimidin-4-yl)benzenesulfonamide (61.5 mg, 0.0983 mmol) prepared in Example 61a, triethylsilane (0.079 mL), dichloromethane (1.0 mL), trifluoroacetic acid (1.0 mL), methanol (15 mL) and 6 M hydrochloric acid (5.0 mL), to yield the title compound (42.0 mg, 99%) as a colorless solid.
$[α]_D^{25}$=16.1 (c 0.943, DMSO).

Formulation Example 1

Tablets can be obtained by mixing 5 g of the compound of Example 33, 90 g of lactose, 34 g of corn starch, 20 g of crystalline cellulose and 1 g of magnesium stearate with a blender and subjecting the thus obtained mixture to tablet compression by using a tableting machine.

Formulation Example 2

Tablets can be obtained by mixing 5 g of the compound of Example 34, 90 g of lactose, 34 g of corn starch, 20 g of crystalline cellulose and 1 g of magnesium stearate with a blender and subjecting the thus obtained mixture to tablet compression by using a tableting machine.

Formulation Example 3

Tablets can be obtained by mixing 5 g of the compound of Example 36, 90 g of lactose, 34 g of corn starch, 20 g of crystalline cellulose and 1 g of magnesium stearate with a blender and subjecting the thus obtained mixture to tablet compression by using a tableting machine.

Formulation Example 4

Tablets can be obtained by mixing 5 g of the compound of Example 48, 90 g of lactose, 34 g of corn starch, 20 g of crystalline cellulose and 1 g of magnesium stearate with a blender and subjecting the thus obtained mixture to tablet compression by using a tableting machine.

Formulation Example 5

Tablets can be obtained by mixing 5 g of the compound of Example 60, 90 g of lactose, 34 g of corn starch, 20 g of crystalline cellulose and 1 g of magnesium stearate with a blender and subjecting the thus obtained mixture to tablet compression by using a tableting machine.

Test Example 1

Construction and Cultivation of Cell Lines

HNav 1.7 and hNav β1 and β2 subunits cloned from human brain were stably expressed by using Lipofectamine (Invitrogen Corp.) in HEK293A cells, and stably expressing cell lines of hNav 1.7/β1/β2 were selected by taking the amount of expression as an indicator. As the culture medium, DMEM (Invitrogen Corp.) containing 20% fetal bovine serum (Hyclone Laboratories, Inc.), 100 U/ml penicillin (Invitrogen Corp.), 100 μg/ml streptomycin (Invitrogen Corp.), 200 μg/ml hygromycin B (Invitrogen Corp.), 200 μg/ml Zeocin (Invitrogen Corp.) and 1 μg/ml puromycin (Clontech Laboratories, Inc.) was used.

Test Example 2

Electrophysiological Evaluation (J. Biomol. Screen., 2006 Aug. 11(5), 488-96

Current recording was obtained by an automated patch clamp system "IonWorks Quattro (Molecular Devices Corporation)" in Population Patch Clamp mode. The operation was conducted in accordance with the operating procedure of the system. A Dulbecco's phosphate buffer containing calcium and magnesium (Sigma) was used as extracellular fluid, and a low Cl-buffer (100 mM K-gluconate, 40 mM KCl, 3.2 mM $MgCl_2$, 5 mM EGTA, 5 mM Hepes, pH 7.3) was used as intracellular fluid. A test compound was dissolved in dimethylsulfoxide (DMSO) to prepare a 30 mM stock solution, so as to produce 4-fold serial dilutions with the extracellular fluid for attaining a DMSO concentration of 0.3% in measurement.

The hNav 1.7/β1/β2 cells cultured to a 70-80% confluent state in a T150 flask (Sumilon) were washed with PBS and subsequently with versene (Invitrogen Corp.), and collected by allowing to react with 0.05% trypsin (Invitrogen Corp.) at 37° C. for 3 minutes. After washing with culture medium, the resultant cells were suspended in extracellular fluid at a concentration of $2 \times 10^{-6}$ cells/ml so as to be used for the measurement. The cell membrane was perforated by using intracellular fluid including 100 μg/ml amphotericin B (Sigma).

Current response was obtained at a sampling frequency of 10 kHz. Leakage current correction was performed by applying a step pulse of −110 mV before a test pulse. The membrane potential was fixed at −100 mV for 5 seconds immediately before applying the test pulse.

In order to check the state-dependency of the inhibiting activity of a test compound, the test pulse was applied as follows: After applying a depolarization pulse of −10 mV for 5 msec., the potential was fixed at −100 mV for 200 msec., a potential (V1/2) at which approximately 50% of channels are inactivated was held for 2 seconds, and a depolarization pulse of −10 mV was applied for 50 msec. Such a test pulse was applied before adding the test compound and after cultivation for 5 minutes and 30 seconds with a solution of the test compound gradually added by 3.5 μl at each time. Since Ion Works Quattro has a measuring electrode head (E-head) and an agent supplying head (F-head) separated from each other, the membrane potential was not clamped during the addition and the cultivation of the test compound.

The inhibiting activity of the test compound was analyzed with respect to the responses to the two depolarization pulses. Data to be analyzed was selected under the conditions that the ratio of the resistance value attained before adding the test compound to the resistance value attained after the addition fell in the range of 0.5 to 1.6, that the seal resistance value was 30 MΩ or more, and that the current response obtained before adding the test compound was ⅓ or more of the average of all wells. Inhibiting activity values were determined on the basis of currents generated in response to the depolarization pulses applied before and after adding the test compound, and the 50% inhibition concentration ($IC_{50}$) was calculated by regression analyzing a 6-point concentration response curve in accordance with the following sigmoidal dose-response function:

$$y = \text{Bottom} + (\text{Top} - \text{Bottom})(1 + 10^{[(\log EC_{50} - x) \times \text{Hill slope}]})$$

The $IC_{50}$ values of the inhibiting activities of test compounds corresponding to the response caused by the second depolarization pulse (with the pre-pulse potential set to V1/2) are shown in Tables 2.

TABLE 2

| Compound | hNav1.7 $IC_{50}$ (μM) |
|---|---|
| 1 | 0.15 |
| 2 | 0.045 |
| 3 | 0.095 |
| 4 | 0.043 |
| 5 | 0.046 |
| 6 | 1.8 |
| 7 | 0.058 |

TABLE 2-continued

| Compound | hNav1.7 IC$_{50}$ (μM) |
|---|---|
| 8 | 0.24 |
| 9 | 0.091 |
| 10 | 0.024 |
| 11 | 0.030 |
| 12 | 0.12 |
| 13 | 0.016 |
| 14 | 0.047 |
| 15 | 0.083 |
| 16 | 0.039 |
| 17 | 0.075 |
| 18 | 0.031 |
| 19 | 0.037 |
| 20 | 0.028 |
| 21 | 0.031 |
| 22 | 0.043 |
| 23 | 0.036 |
| 24 | 0.070 |
| 25 | 0.086 |
| 26 | 0.036 |
| 27 | 0.089 |
| 28 | 0.065 |
| 29 | 0.12 |
| 30 | 0.036 |
| 31 | 0.042 |
| 32 | 0.05 |
| 33 | 0.10 |
| 34 | 0.02 |
| 35 | — |
| 36 | 2.4 |
| 37 | 0.014 |
| 38 | 0.12 |
| 39 | 0.1 |
| 40 | 0.059 |
| 41 | 0.057 |
| 42 | 0.051 |
| 43 | 0.03 |
| 44 | 0.024 |
| 45 | 0.035 |
| 46 | 0.034 |
| 47 | 0.058 |
| 48 | 0.021 |
| 49 | 0.024 |
| 50 | 0.018 |
| 51 | 0.021 |
| 52 | 0.017 |
| 53 | 0.13 |
| 54 | 0.028 |
| 55 | 0.041 |
| 56 | 0.05 |
| 57 | 0.04 |
| 58 | 0.059 |
| 59 | 0.028 |
| 60 | 0.043 |
| 61 | 0.034 |

Test Example 3

Antitussive Assay

In the present invention, normal mice were used for evaluation.

A test compound was orally administered at a dose of 100 mg/kg to an animal, and cough was evaluated at each measurement time determined by the study director. Specifically, citric acid atomized with a nebulizer was inhaled to the animal, and the number of cough episodes was measured.

The test compound was evaluated by calculating the rate of suppressing the number of cough episodes (%) at a constant dose against a vehicle treatment group. Rates of suppressing the number of cough episodes (%) at a constant dose are shown in Table 3 as "C" when the rate was 0 to 30%, as "B" when the rate was 31 to 60%, and as "A" when the rate was 61 to 100%.

TABLE 3

| Compound | Rate of suppressing the number of cough episodes (%) |
|---|---|
| 1 | — |
| 2 | — |
| 3 | — |
| 4 | — |
| 5 | — |
| 6 | — |
| 7 | — |
| 8 | — |
| 9 | — |
| 10 | — |
| 11 | — |
| 12 | — |
| 13 | — |
| 14 | — |
| 15 | — |
| 16 | — |
| 17 | — |
| 18 | — |
| 19 | — |
| 20 | — |
| 21 | — |
| 22 | — |
| 23 | — |
| 24 | — |
| 25 | — |
| 26 | — |
| 27 | — |
| 28 | — |
| 29 | A |
| 30 | — |
| 31 | — |
| 32 | — |
| 33 | A |
| 34 | A |
| 35 | — |
| 36 | B |
| 37 | — |
| 38 | A |
| 39 | — |
| 40 | — |
| 41 | — |
| 42 | — |
| 43 | — |
| 44 | — |
| 45 | — |
| 46 | — |
| 47 | — |
| 48 | — |
| 49 | — |
| 50 | — |
| 51 | — |
| 52 | — |
| 53 | — |
| 54 | — |
| 55 | — |
| 56 | — |
| 57 | — |
| 58 | — |
| 59 | — |
| 60 | — |
| 61 | — |

INDUSTRIAL APPLICABILITY

The compound represented by formula (I) or a pharmacologically acceptable salt thereof is useful because it can be used as an active ingredient of a pharmaceutical composition for treating and/or preventing respiratory diseases, sodium channel associated diseases or disorders such as central nervous system disorders.

What is claimed is:

1. A method of suppressing a cough, comprising administering a pharmacologically effective amount of a compound of formula (I):

[Formula 1]

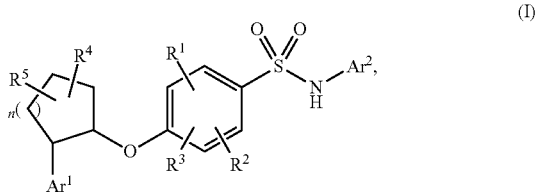

or a pharmacologically acceptable salt thereof,
to a mammal, wherein
$Ar^1$ and $Ar^2$ are each independently a heteroaryl group or an aryl group,
$R^1$, $R^2$ and $R^3$ are each independently a hydrogen atom, a halogen atom, a C1-C6 alkyl group, a halogenated C1-C6 alkyl group, a hydroxy C1-C6 alkyl group, a C1-C6 alkoxy C1-C6 alkyl group, a C3-C7 cycloalkyl group or a cyano group,
$R^4$ and $R^5$ are each independently a hydrogen atom, a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group or a C1-C6
n is an integer of 1 to 3, and
the heteroaryl or aryl group is optionally substituted with one or two substituents independently selected from a halogen atom, a C1-C6 alkyl group, a halogenated C1-C6 alkyl group, a hydroxyl group, a hydroxy C1-C6 alkyl group, a C1-C6 alkoxy C1-C6 alkyl group, a C3-C7 cycloalkyl group, a carboxy group, a cyano group, an amino group, a C1-C3 alkylamino group and a di-C1-C3 alkylamino group, and when two such groups are present in the heteroaryl or aryl group, the two may be the same as, or different from, each other.

2. The method of claim 1, wherein the mammal is a human.

3. The method of claim 1, wherein the compound or salt of formula (I) is administered in an amount of 0.1 mg to 2000 mg per day.

4. The method of claim 3, wherein the compound or salt of formula (I) is administered in an amount of 1 mg to 100 mg per day.

5. The method of claim 3, wherein the amount is provided in one to six doses.

6. The method of claim 1, wherein the compound or salt of formula (I) is administered with a pharmacologically acceptable carrier as a pharmaceutical composition.

7. The method of claim 1, wherein the compound or salt of formula (I) is administered orally, parenterally, rectally, or as a drip infusion.

8. The method of claim 7, wherein the oral administration is by tablet, capsule, granule, emulsion, pill, powder, or syrup.

9. The method of claim 7, wherein the parenteral administration is by injection.

10. The method of claim 9, wherein the injection is intravenous, intramuscular, subcutaneous, or intraperitoneal.

11. The method of claim 1, wherein the mammal has bronchial asthma, asthmatic bronchitis, acute bronchitis, chronic bronchitis, cold, bronchiectasis, pneumonia, pulmonary tuberculosis, upper respiratory inflammation, laryngopharyngitis, nasal catarrh, bronchitis, asthmatic bronchitis, or cough associated with bronchial asthma.

12. The method of claim 1, wherein the compound of formula (I) is
2-fluoro-4-{[(1S*,2R*)-2-(1-methyl-1H-pyrazol-5-yl)cyclopentyl]oxy}-N-(pyrimidin-4-yl)benzenesulfonamide;
4-{[(1S*,2R*)-2-(1-ethyl-1H-pyrazol-5-yl)cyclopentyl]oxy}-2,3-difluoro-N-(pyrimidin-4-yl)benzenesulfonamide;
5-chloro-2-fluoro-4-{[(1S*,2R*)-2-(1-methyl-1H-pyrazol-5-yl)cyclohexyl]oxy}-N-(pyrimidin-4-yl)benzenesulfonamide;
2,6-difluoro-4-{[(1S*,2R*)-2-(1H-pyrazol-4-yl)cyclohexyl]oxy}-N-(pyrimidin-4-yl)benzenesulfonamide;
4-{[(1S,2R)-2-(1-ethyl-1H-pyrazol-5-yl)cyclopentyl]oxy}-2,3-difluoro-N-(pyrimidin-4-yl)benzenesulfonamide;
5-chloro-2-fluoro-4-{[(1S,2R)-2-(1-methyl-1H-pyrazol-5-yl)cyclohexyl]oxy}-N-(pyrimidin-4-yl)benzenesulfonamide;
2-fluoro-4-{[(1S,2R)-2-(1-methyl-1H-pyrazol-5-yl)cyclopentyl]oxy}-N-(pyrimidin-4-yl)benzenesulfonamide;
4-{[(1S*,2R*)-5,5-difluoro-2-(1H-pyrazol-4-yl)cyclohexyl]oxy}-2-fluoro-5-methyl-N-(pyrimidin-4-yl)benzenesulfonamide;
4-{[(1S,2R)-5,5-difluoro-2-(1H-pyrazol-4-yl)cyclohexyl]oxy}-2-fluoro-5-methyl-N-(pyrimidin-4-yl)benzenesulfonamide;
2,6-difluoro-4-{[(1S,2R)-2-(1H-pyrazol-4-yl)cyclohexyl]oxy}-N-(pyrimidin-4-yl)benzenesulfonamide;
5-chloro-2-fluoro-4-{[(1S*,2R*,4R*)-4-hydroxy-2-(1-methyl-1H-pyrazol-5-yl)cyclohexyl]oxy}-N-(pyrimidin-4-yl)benzenesulfonamide; or
5-chloro-2-fluoro-4-{[(1S,2R,4R)-4-hydroxy-2-(1-methyl-1H-pyrazol-5-yl)cyclohexyl]oxy}-N-(pyrimidin-4-yl)benzenesulfonamide.

13. The method of claim 1, wherein the compound of formula (I) is 4-{[(1S,2R) -2-(1-ethyl-1H-pyrazol-5-yl)cyclopentyl]oxy}-2,3-difluoro-N-(pyrimidin-4-yl)benzenesulfonamide.

14. The method of claim 1, wherein the compound of formula (I) is 5-chloro-2-fluoro-4-{[(1S,2R)-2-(1-methyl-1H-pyrazol-5-yl)cyclohexyl]oxy}-N-(pyrimidin-4-yl)benzenesulfonamide.

15. The method of claim 1, wherein the compound of formula (I) is 2-fluoro-4-{[(1S,2R)-2-(1-methyl-1H-pyrazol-5-yl)cyclopentyl]oxy}-N-(pyrimidin-4-yl)benzenesulfonamide.

* * * * *

UNITED STATES PATENT AND TRADEMARK OFFICE
CERTIFICATE OF CORRECTION

PATENT NO. : 9,597,330 B2
APPLICATION NO. : 14/776315
DATED : March 21, 2017
INVENTOR(S) : Takahashi et al.

It is certified that error appears in the above-identified patent and that said Letters Patent is hereby corrected as shown below:

In the Claims

In Claim 1, Column 119, Line 30, delete "C3-C7 cycloalkyl group or a C1-C6" and insert therefor -- C3-C7 cycloalkyl group or a C1-C6 alkoxy group --.

Signed and Sealed this
Twentieth Day of June, 2017

Joseph Matal
*Performing the Functions and Duties of the*
*Under Secretary of Commerce for Intellectual Property and*
*Director of the United States Patent and Trademark Office*